US008088823B2

(12) United States Patent
Ascher et al.

(10) Patent No.: US 8,088,823 B2

(45) Date of Patent: Jan. 3, 2012

(54) TUBERCULOSIS TREATMENT USING PLEUROMUTILIN DERIVATIVES

(75) Inventors: Gerd Ascher, Kundl (AT); Heinz Berner, Vienna (AT); Rosemarie Mang, Vienna (AT)

(73) Assignee: Nabriva Therapeutics AG, Vienna (AT)

( * ) Notice: Subject to any disclaimer, the term of this patent is extended or adjusted under 35 U.S.C. 154(b) by 1123 days.

(21) Appl. No.: 11/818,094

(22) Filed: Jun. 13, 2007

(65) Prior Publication Data

US 2007/0270404 A1 Nov. 22, 2007

Related U.S. Application Data

(62) Division of application No. 10/509,502, filed as application No. PCT/EP03/003215 on Mar. 27, 2003, now abandoned.

(30) Foreign Application Priority Data

| | | |
|---|---|---|
| Mar. 28, 2002 | (GB) | 0207495.3 |
| Jul. 24, 2002 | (GB) | 0217149.4 |
| Jul. 25, 2002 | (GB) | 0217305.2 |

(51) Int. Cl.
*A01N 37/00* (2006.01)
*A61K 31/21* (2006.01)

(52) U.S. Cl. ........................................ 514/506; 514/510

(58) Field of Classification Search .................. 514/183, 514/506, 510
See application file for complete search history.

(56) References Cited

U.S. PATENT DOCUMENTS

| | | | | |
|---|---|---|---|---|
| 4,278,674 A | | 7/1981 | Egger et al. | |
| 4,517,178 A | * | 5/1985 | Isono et al. | 424/122 |
| 7,534,814 B2 | * | 5/2009 | Ascher et al. | 514/511 |
| 2005/0159377 A1 | | 7/2005 | Ferguson et al. | |

FOREIGN PATENT DOCUMENTS

| | | |
|---|---|---|
| EP | 0013768 | 8/1980 |
| WO | WO 0071560 | 11/2000 |
| WO | WO 02/12199 | 2/2002 |
| WO | WO 02/22580 | 3/2002 |

* cited by examiner

*Primary Examiner* — Yong Chong

(74) *Attorney, Agent, or Firm* — D. Peter Hochberg; Sean F. Mellino; Daniel J. Smola

(57) ABSTRACT

A method of preventing or treating diseases caused by *Mycobacterium,* comprising administering to a subject in need of such treatment an effective amount of a pleuromutilin.

2 Claims, No Drawings

TUBERCULOSIS TREATMENT USING PLEUROMUTILIN DERIVATIVES

CROSS REFERENCE TO RELATED APPLICATIONS

This application is a divisional application of prior U.S. application Ser. No. 10/509,502, filed on Sep. 28, 2004 now abandoned, which is a U.S. national phase application of International Application No. PCT/EP03/03215, filed on Mar. 27, 2003, and which claims priority of United Kingdom application number 0207495.3, filed on Mar. 28, 2002, United Kingdom application number 0217149.4, filed on Jul. 24, 2002 and United Kingdom application number 0217305.2, filed on Jul. 25, 2002.

BACKGROUND OF THE INVENTION

1. Field of the Invention

The present invention relates to tuberculosis treatment, such as treatment of diseases mediated by *Mycobacterium,* e.g. *Mycobacterium tuberculosis,* with pleuromutilins.

2. Description of the Prior Art

Tuberculosis is a chronic infectious disease mediated by infection with *Mycobacterium tuberculosis*. Tuberculosis is a major disease in developing countries, as well as an increasing problem in developed areas of the world. Although the infection may be asymptomatic for a considerable period of time, the disease is most commonly manifested as an acute inflammation of the lungs, resulting in fever and a nonproductive cough. If untreated, serious complications and death typically result. Tuberculosis may be generally controlled by antibiotic therapy, such as by treatment with Isoniazid, see e.g. The Merck Index, 12th edition, item 5203; Rifampin (Rifampicin®), see e.g. The Merck Index, 12th edition, item 8382, Streptomycin, see e.g. The Merck Index, 12th edition, item 8983; but a major problem is the development of strain drug resistance against such antibiotics.

SUMMARY OF THE INVENTION

We have now found a compound class which shows surprisingly activity in the treatment of diseases caused by *Mycobacterium,* such as *Mycobacterium tuberculosis,* e.g. even against drug resistant strains.

In one aspect the present invention provides the use of a pleuromutilin in the preparation of a medicament for the treatment of diseases mediated by *Mycobacterium.*

In another aspect the present invention provides a method of treating diseases mediated by *Mycobacterium,* comprising administering to a subject in need of such treatment an effective, e.g. an anti-mycobacterium effective; amount of a pleuromutilin.

*Mycobacterium* includes *M. tuberculosis*. Diseases mediated by *Mycobacterium* include mycobacterium infections. A pleuromutilin for treatment includes one or more pleuromutilins, e.g. a combination of different pleuromutilins. Treatment includes treatment and prophylaxis.

DETAILED DESCRIPTION OF THE PRESENT INVENTION

A pleuromutilin for use according to the present invention or for treating diseases according to the present invention is designated hereinafter as "a pleuromutilin(s) of (according to) the present invention".

A pleuromutilin of the present invention includes a pleuromutilin in the form of a free base, and, where existing, in the form of a salt, in the form of a solvate and in the form of a salt and a solvate, e.g. and in the form of a complex, such as a cyclodextrin complex.

A pleuromutilin of the present invention may exist in the form of isomers and mixtures thereof, e.g. including diastereoisomers and mixtures thereof. Isomeric mixtures may be separated as appropriate, e.g. according to a method as conventional, to obtain pure isomers. The present invention includes a pleuromutilin according to the present invention in any isomeric form and in any isomeric mixture, such as described in patent literature cited below, which patent literature is introduced herein by reference with respect to isomeric forms of pleuromutlins. Preferably the configuration in the mutilin ring is the same as in a naturally produced mutilin.

Pleuromutilin, a compound of formula

A

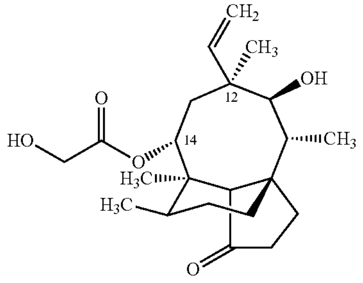

is a naturally occurring antibiotic, e.g. produced by the basidomycetes *Pleurotus mutilus* and *P. passeckerianus,* see e.g. The Merck Index, 12th edition, item 7694.

A number of further pleuromutilins having the principle ring structure of pleuromutilin and having e.g. antibacterial activity, have been developed.

A pleuromutilin of the present invention includes a pleuromutilin having the basic structural elements as set out in formula

PLEU

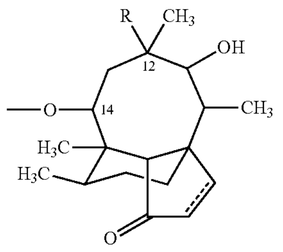

wherein R is vinyl or ethyl and the dotted line is a bond or is no bond.

The following numbering system is used in the present application:

PLEU

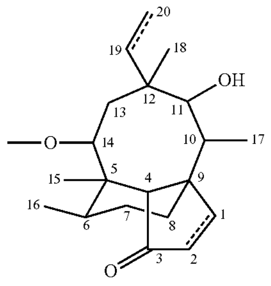

The dotted line between positions 19 and 20 (and between positions 1 and 2) is a bond or is no bond. In a compound of formula A or of formula PLEU a hydrogen atom in positions 4, 7 and/or 8 of the ring system may be replaced by deuterium, and if the dotted line between positions 1 and 2 is no bond (single bond between positions 1 and 2) the ring system may be further substituted in positions 1 and/or 2, e.g. by halogen, deuterium or hydroxy. The group —O— in position 14 is further substituted, preferably by a substituted carbonyl group.

Examples of pleuromutilins according to the present invention includes e.g.

A compound as disclosed in U.S. Pat. No. 3,716,579, e.g. of formula

I-US3716579

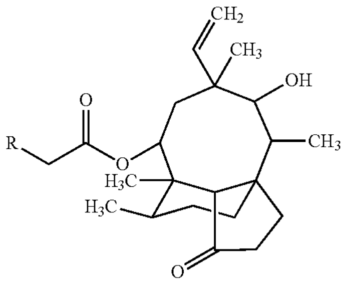

wherein R is $CH_3—(CH_2)_7—CH═CH—(CH_2)_7—COO—$, $CH_3—(CH_2)_4—CH═CH—CH_2—CH═CH—(CH_2)_7—COO—$, $CH_3—(CH_2)_9—CH═CH—(CH_2)_7—COO—$ or hydrogen;

A compound as disclosed in GB1312148, e.g. of formula

I-GB1312148

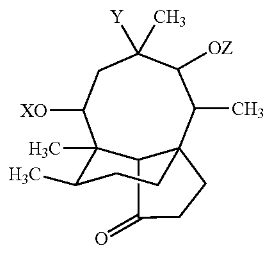

wherein X, Y and Z are as defined in any one of the following groups:

a. X is $—CO—CH_2—R_1$, wherein $R_1$ is H, Cl, Br, I, thiocyanato, azido, (N,N-tetramethylene-thiocarbamoyl)-mercapto, dithiocarbonic acid-O—$(C_{1-3})$alkyl, —S-phenyl, S-phenyl substituted by carboxyl or by one or two OH, —S-pyridyl, —S-benzyl, —S—$(C_{1-5})$alkyl, or —S—$(C_{1-5})$alkyl substituted by one or more amino, OH or carboxyl, Y is vinyl, and Z is H;

b. X is —CO—CO—OH, Y is vinyl and Z is H;

c. X is $—COCH_3$, Y is vinyl and Z is H;

d. X is $COCH_2NH_2$, Y is ethyl and Z is H;

e. X is a group of formula

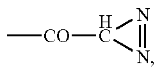

Y is ethyl and Z is H f. X is H, Y is vinyl and Z is acetyl; or g. X is $COR_2$, wherein $R_2$ is $(C_{1-5})$alkyl, Y is vinyl and Z is H, A compound as disclosed in U.S. Pat. No. 4,278,674, e.g. of formula

I-US4278674

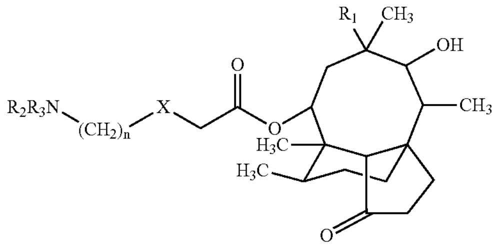

wherein $R_1$ is vinyl or ethyl, n is an integer from 2 to 5, X is sulphur or a group —Y-phenylene-Z- or a group $═NR_4$, Y and Z are both sulphur or one of Y and Z is sulphur and the other is oxygen, $R_4$ is H or a second mutilin ring of formula I-U.S. Pat. No. 4,278,674, wherein $R_1$ is as defined above and attached via a $—O—CO—CH_2—$ group in position 14; each of $R_2$ and $R_3$ are (independently of each other) $(C_{1-10})$alkyl, or $R_2$ and $R_3$ together with the nitrogen atom form pyrrolidino, piperidino, morpholino, thiomorpholino, or 1-hexahydro-1H-azepino, or $R_2$ and $R_3$ together with the nitrogen atom form piperazinyl, the second nitrogen atom of which is substituted by $(C_{1-5})$alkyl, $(C_{1-4})$hydroxyalkyl, $(C_{2-5})$alkynoyloxy$(C_{1-4})$alkyl, or benzoyloxy$(C_{1-4})$alkyl, or $R_1$ is as defined above, n=2, $R_3$ is $(C_{1-10})$alkyl, $(C_{1-4})$hydroxyalkyl, $(C_{2-5})$alkynoyloxy-$(C_{1-4})$alkyl, or benzoyloxy$(C_{1-4})$alkyl, X is $═NR'_4$ and $R_2$ together with $R'_4$ forms an ethylene bridge between both nitrogen atoms; such as 14-Desoxy-14[(2-diethylaminoethyl)mercaptoacetoxy]mutilin, e.g. also known as tiamulin of formula I-Tiamulin

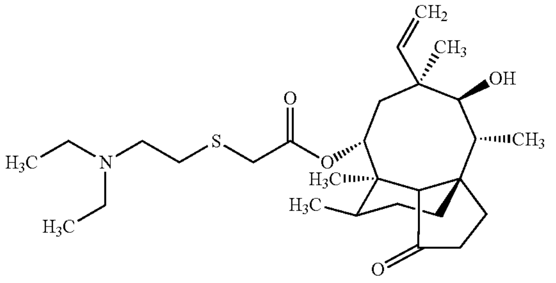

A compound as disclosed in U.S. Pat. No. 4,130,709, e.g. of formula

I-US4130709

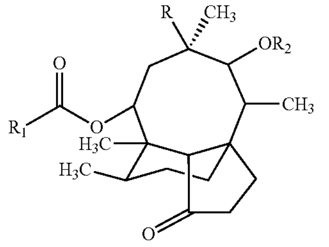

wherein R is ethyl or vinyl, $R_1$ is selected from α- or β-anomers of hexopyranoses, hexofuranoses, pentopyranoses, pentofuranoses, pyranose and furanose aminosugars, disaccharides, trisaccharides and $R_2$ is H, benzoyl or $(C_{2-4})$alkanoyl; or $R_1$ is 2-deoxy-2-(hydroxyimino)-3,4,6-tri-O-acetyl-α-D-glucopyranosyl or -galactopyranosyl, 2-deoxy-2-(hydroxyimino)-α-D-galactopyranosyl, 2-deoxy-2-amino-4,6-di-O-acetyl-α-D-glucopyranosyl, or 2-deoxy-2-acetamido-3,4,6-tri-O-acetyl-α-D-glucopyranosyl and $R_2$ is H;

A compound as disclosed in U.S. Pat. No. 4,129,721; e.g. of formula

I-US4129721

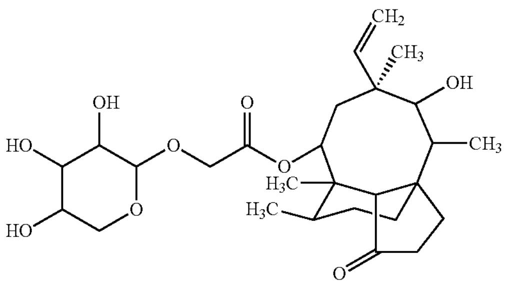

and the 19,20-dihydro derivative thereof and the tetra$(C_{2-6})$ alkanoyl derivatives thereof;

A compound as disclosed in EP0013768, e.g. of formula

I-EP0013768

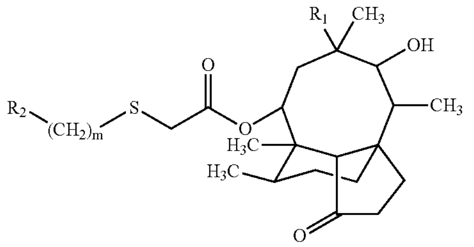

wherein $R_1$ is vinyl or ethyl, m is 0 or 1, and $R_2$ is a heterocyclic radical, in which a 5- or 6-membered, unsaturated or saturated heterocyclic ring containing one or more hetero atoms selected from O, S and N, is attached to the —S$(CH_2)_m$— group;

A compound as disclosed in EP0153277, e.g. an N-acyl-14-O-[(1-amino-2-methylpropan-2-yl)thioacetyl]-mutilin or 19,20-dihydromutilin, such as of formula

I-EP0153277

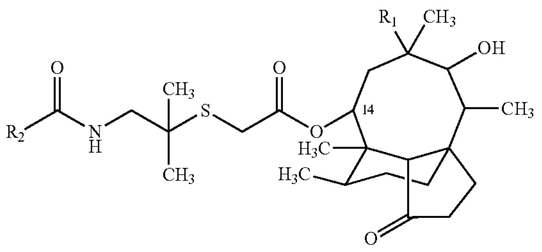

wherein $R_1$ is vinyl or ethyl positions 19 and 20), and $R_2$ is optionally hydroxy-substituted aminoalkyl or a 5-membered saturated heterocycle, e.g. including Valnemulin (Econor®) of formula I-Valnemulin

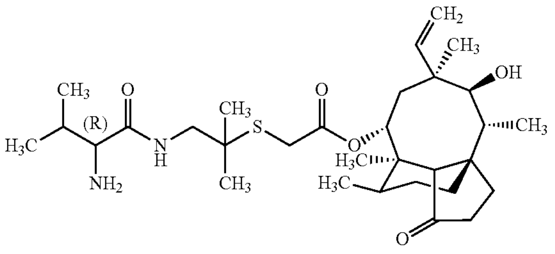

A compound as disclosed in U.S. Pat. No. 516,526, e.g. of formula

I-US5164526

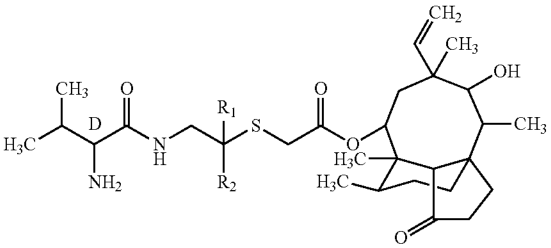

wherein $R_1$ and $R_2$ independently of each other are H, alkyl, alkenyl, cycloalkyl, aryl or aralkyl;

A compound as disclosed in WO9322288, e.g. of formula

I-WO9322288

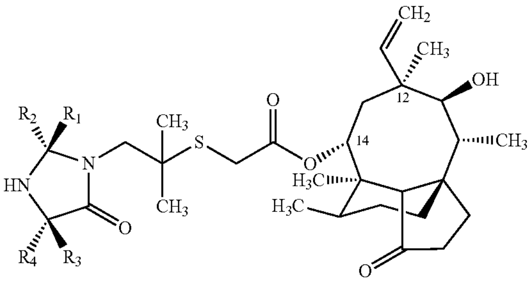

wherein $R_1$ and $R_2$ are independently of each other H, alkyl, or, $R_1$ and $R_2$ together with the carbon atom to which they are attached are cycloalkyl; and $R_3$ and $R_4$ independently of each other are H, alkyl or substituted alkyl;

A compound as disclosed in WO9725309, e.g. of formula

I-WO9725309

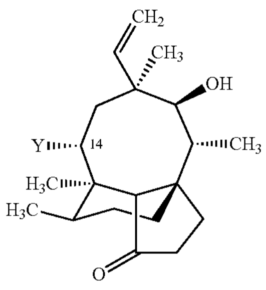

wherein Y is carbamoyloxy, wherein the N-atom is unsubstituted or mono- or disubstituted, such as a compound of formula

II-WO9725309

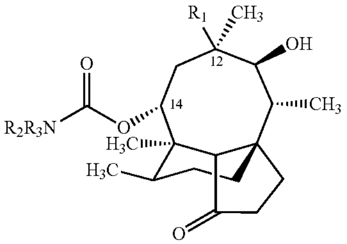

wherein $R_1$ is vinyl or ethyl, $R_2$ and $R_3$ independently of each other are H, or optionally substituted saturated or unsaturated $(C_{1-6})$ hydrocarbon or $(C_{3-8})$cyclic hydrocarbon, heterocyclyl or aryl, or $R_2$ and $R_3$ together form an optionally substituted cyclic group of 3 to 8 ring atoms, optionally containing one additional heteroatom selected from N, O and S, and optionally fused to a hydrocarbon ring, a heterocyclic group or an aromatic group; or $R_2$ is one of the above monovalent groups and $R_3$ is a group selected form $SO_2R_4$, $COR_5$, $OR_5$ and $NR_6R_7$; wherein $R_4$ is optionally substituted, saturated or unsaturated $(C_{1-6})$hydrocarbon or $(C_{3-8})$cyclic hydrocarbon, heterocyclyl, aryl, $(C_{1-6})$alkylamino or arylamino;

$R_5$ is optionally substituted saturated or unsaturated $(C_{1-6})$ hydrocarbon or $(C_{3-8})$cyclic hydrocarbon, heterocyclyl or aryl, $R_6$ and $R_7$ independently of each other are H, or optionally substituted saturated or unsaturated $(C_{1-6})$ hydrocarbon or $(C_{3-8})$cyclic hydrocarbon, heterocyclyl or aryl, or $R_6$ and $R_7$ together with the nitrogen atom to which they are attached form an optionally substituted $(C_{3-8})$cyclic group, optionally containing one additional heteroatom selected from N, O or S, and optionally fused to a hydrocarbon ring, a heterocyclic ring or an aromatic group;

A compound as disclosed in WO9805659, e.g. of formula

I-WO9805659

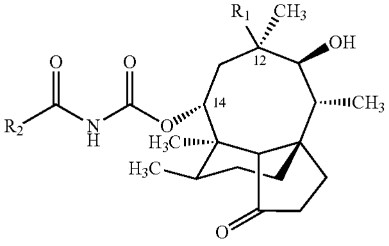

wherein $R_1$ is vinyl or ethyl, and $R_2$ is a group $R_3$, $R_4CH_2$—, or $R_5R_6CH$=CH—, wherein, each of $R_3$ and $R_4$ is an azabicyclic ring system, or $R_5$ and $R_6$ together with the carbon atom to which they are attached form an azabicyclic ring system;

A compound of WO9821855; e.g. of formula

IA-WO9821855

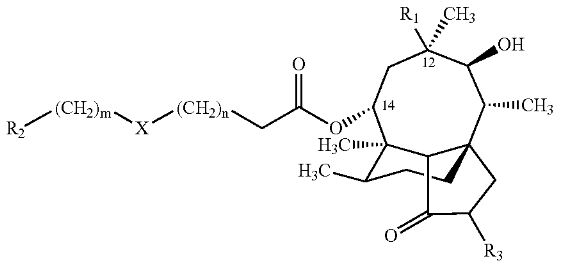

IB-WO9821855

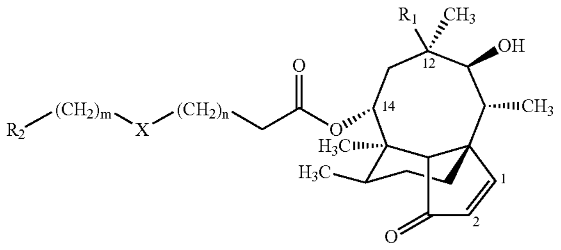

wherein n and m are independently of each other 0, 1 or 2; X is O, S, S(O), $SO_2$, —COO—, —NH—, —CONH—, —NHCONH—, or a bond; $R_1$ is vinyl or ethyl; $R_2$ is a non-aromatic monocyclic or bicyclic group containing one or two basic nitrogen atoms and attached through a ring carbon atom, e.g. $R_2$ is optionally substituted quinuclidinyl, azabicyclo[2.2.1]heptyl, azabicyclo[4.3.0]nonyl, azabicyclo[3.2.1]octyl, azabicyclo[3.3.0]octyl, azabicyclo [2.2.2]octyl, azabicyclo[3.2.1]octenyl, azabicyclo[3.3.1] nonyl or azabicyclo[4.4.0]decyl; $R_3$ is H, OH; or the moiety $R_2(CH_2)_mX(CH_2)_nCH_2COO$ at position 14 of IA or IB is replaced by $R_aR_bC$═CHCOO, wherein one of $R_a$ or $R_b$ is hydrogen and the other is $R_2$; or $R_a$ and $R_b$ together form $R_2$;

A compound as disclosed in WO0007974, e.g. a 14-acyloxy derivative of mutilin or 19,20-dihydromutilin having a 2-fluoro substituent, such as of formula

IA-WO0007974

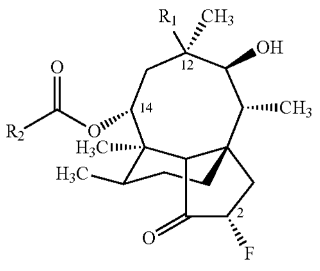

-continued

IB-WO0007974

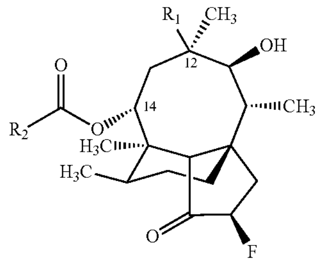

wherein $R_1$ is vinyl or ethyl (positions 19 and 20), and $R_2$COO— is acyloxy, e.g. $HOCH_2CO_2$— or R—X—$CH_2CO_2$, wherein X is O, S or NR' and R and R' are independently of each other an aliphatic or aromatic group, preferably $R_2$COO— is a carbamoyl group, such as a group $R_3R_4NCO_2$— wherein $R_3$ and $R_4$ have various meanings (e.g. $R_3$ and $R_4$ have the meaning as disclosed for the meaning of $R_2$ and $R_3$ in WO9725309);

A compound as disclosed in WO 0027790, e.g. a compound of formula

IA-WO00/27790

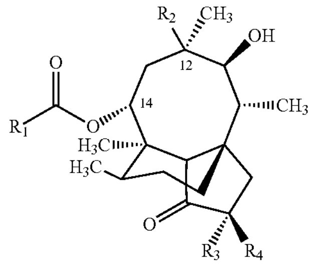

IB-WO00/27790

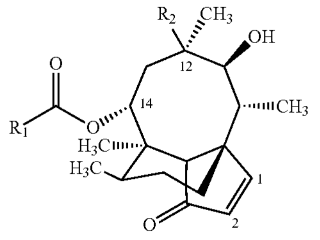

wherein $R_1$ is a $R^A(CH_2)_nO(CH_2)_m$, $R^A(CH_2)_p$, or a group of formula

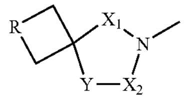

wherein R is a spiro-fused mono- or bicyclic ring containing one or two basic N-atoms; $X_1$ and $X_2$ which may be the same or different, are each —$CH_2$— or —C═O, provided that at least one of $X_1$ and $X_2$ is —C═O; and Y is —NH—, —$CH_2$— or —$CH_2$—$CH_2$—;

$R^A$ is an optionally substituted aryl group or heteroaryl group linked via a carbon atom;

e.g. $R^A$ is optionally substituted phenyl, thienyl, pyridinyl, furyl, thiazolyl, isoxazolyl, benzimidazolyl, quinolinyl, 1,2,3,4-tetrahydro-isoquinolinyl or benzthiazolyl:

m is 1, 2 or 3; n is 0, 1 or 2; p is 1 to 4; $R_2$ is vinyl or ethyl; and $R_3$ is H, OH or F, and $R_4$ is H; or $R_3$ is H and $R_4$ is F;

A compound as disclosed in WO0037074, e.g. a compound of formula

IA-WO0037074

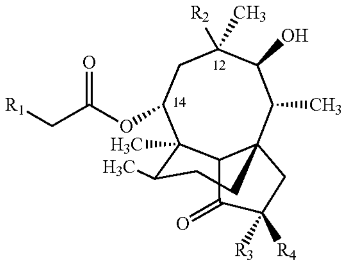

IB-WO0037074

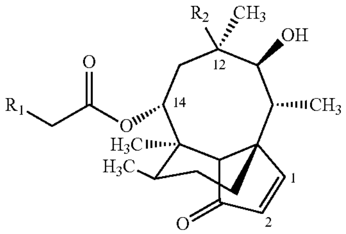

wherein $R_1$ is an optionally substituted heteroaryl group which comprises a 5-membered heteroaromatic ring which has at least one N-atom, e.g. a pyrrole, pyrazole, imidazole, 1,2,3-triazole, 1,2,4-triazole, indole, benzimidazole, benzotriazole, 2-aza-indole or 6-aza-indole; and which is linked via a N-atom; $R_2$ is vinyl or ethyl; $R_3$ is H, OH or F, and $R_4$ is H; or $R_3$ is H and $R_4$ is F;

A compound as disclosed in WO0073287, e.g. a compound of formula

IA-WO0073287

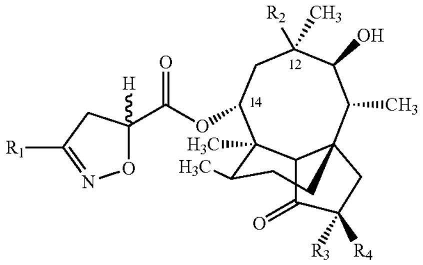

IB-WO0073287

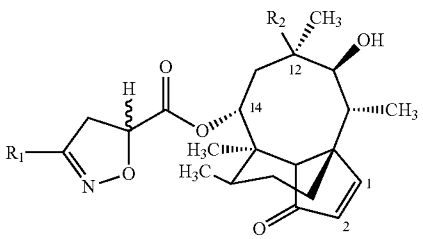

wherein $R_1$ is optionally substituted aryl, e.g. azabicyclo-octyl; or an optionally substituted nitrogen containing ring, e.g. piperidinyl; $R_2$ is vinyl or ethyl; $R_3$ is H, OH or F and $R_4$ is H; or $R_3$ is H and $R_4$ is F;

A compound as disclosed in WO0114310, e.g. a compound of formula

IA-WO0114310

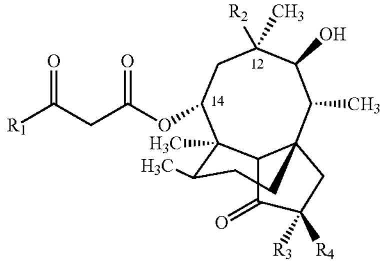

IB-WO0114310

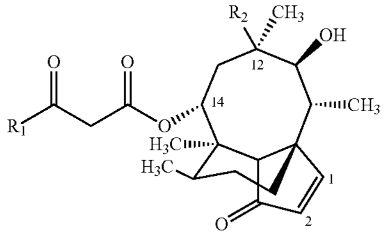

wherein $R_1$ is a nitrogen containing heterocycle, an optionally substituted aryl or optionally substituted heteroaryl, or $CH_2R_5$, e.g. $R_1$ is optionally substituted phenyl, 3-pyridyl, 4-pyridyl, pyrimidin-2-yl, 1,3,4-thiadiazol-2-yl, benzothiazol-2-yl. 2H-1,2,4-triazol-3-yl, azabicycloheptyl, azabicyclooctyl or piperidinyl;

$R_2$ is vinyl or ethyl; $R_3$ is H, OH or F and $R_4$ is H; or $R_3$ is H and $R_4$ is F; $R_5$ is halogen or $SR_6$; and $R_6$ is aminoalkyl, a nitrogen containing heterocycle, or an optionally substituted aryl or optionally substituted heteroaryl; e.g. $R_6$ is optionally substituted phenyl, 3-pyridyl, 4-pyridyl, pyrimidin-2-yl, 1,3,4-thiadiazol-2-yl, benzothiazol-2-yl. 2H-1,2,4-triazol-3-yl, azabicycloheptyl, azabicyclooctyl or piperidinyl;

A compound as disclosed in WO0109095, e.g. a compound of formula

I-WO0109095

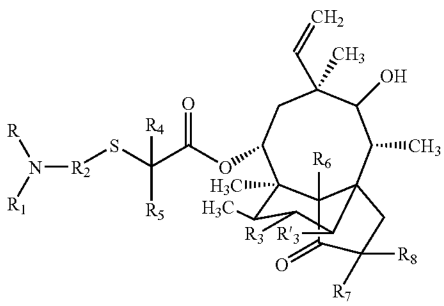

wherein R is hydrogen or alkyl; $R_1$ is hydrogen or a group of formula

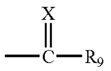

wherein X is S, O, or $NR_{10}$, wherein $R_{10}$ is H or alkyl, or $N^+(R'_{10})_2$ wherein $R'_{10}$ is alkyl in the presence of an appropriate anion; and $R_9$ is amino, alkyl, aryl, heterocyclyl or mercapto; and, if X is oxygen, $R_9$ is additionally hydrogen; $R_2$ is arylene, e.g. phenylene; or heterocyclene; $R_4$ is hydrogen or alkyl; $R_5$ is hydrogen or alkyl; $R_3$, $R_3'$, $R_6$, $R_7$ and $R_8$ independently of each other are hydrogen or deuterium; or R and $R_2$ together with the nitrogen atom to which they are attached form non-aromatic heterocyclene and $R_1$ is a group of formula

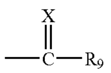

wherein X and $R_9$ are as defined above; e.g. a compound of formula $I_s$WO0109095

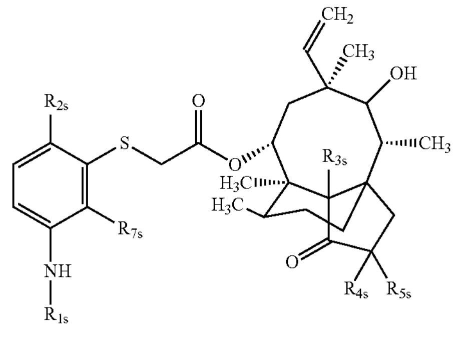

wherein $R_{1s}$ is hydrogen or a group of formula

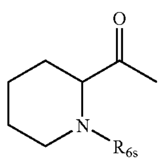

wherein $R_{6s}$ is hydrogen or deuterium; $R_{2s}$ is hydrogen, methyl or tert-butyl; $R_{7s}$ is hydrogen or methyl; and $R_{3s}$, $R_{4s}$ and $R_{5s}$ are hydrogen or deuterium;

A compound as disclosed in WO0174788, e.g. a compound of formula

I-WO0174788

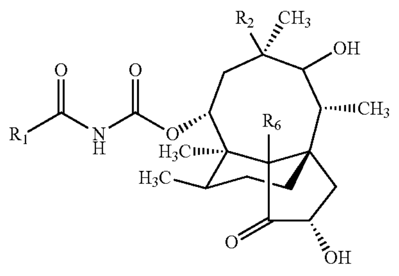

wherein $R_1$ is a 5- or 6-membered optionally substituted heteroaryl group; e.g. pyridine, pyridazine, pyrimidine, pyrazine, isoxazole, thiazole, imidazole, pyrazole, 1,2,3-triazole, 1,2,4-triazole, benzimidazole, 3-oxo-3,4-dihydropyrido[2,3-b]pyrazine, or pyrazolo[1,5-a]pyrimidine; and $R_2$ is vinyl or ethyl;

A compound as disclosed in WO0204414, e.g. a compound selected from 14-O-[(cycloalkyl-sulfanyl)acetyl]mutilins; 14-O-[(cycloalkyl-alkyl-sulfanyl)acetyl]mutilins; 14-O-[(cycloalkoxy)acetyl]mutilins; or 14-O-[(cycloalkyl-alkoxy)acetyl]mutilins, such as of formula

I-WO0204414

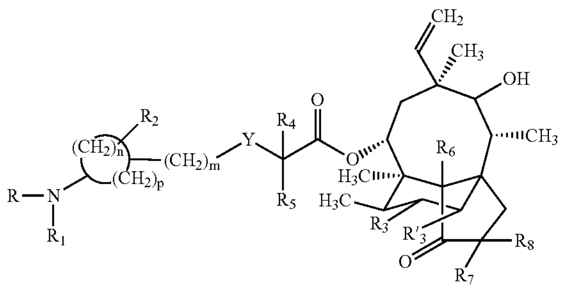

wherein R is hydrogen; $R_1$ is hydrogen or a group of formula

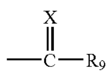

wherein X is sulphur, oxygen or $NR_{10}$, wherein $R_{10}$ is hydrogen or alkyl; and $R_9$ is amino, alkyl, aryl or heterocyclyl; and, if X is oxygen, $R_9$ is additionally hydrogen; Y is sulphur or oxygen; $R_2$ is hydrogen or one or more substituents, $R_4$ is hydrogen or alkyl; $R_5$ is hydrogen or alkyl; $R_3$ and $R_3'$ are hydrogen, deuterium, or halogen; $R_6$, $R_7$ and $R_8$ are hydrogen or deuterium; m is a number selected from 0 to 4; n is a number selected from 0 to 10; and p is a number selected from 0 to 10; with the proviso that n plus p are at least 1; e.g. a compound of formula $I_p$-WO0204414

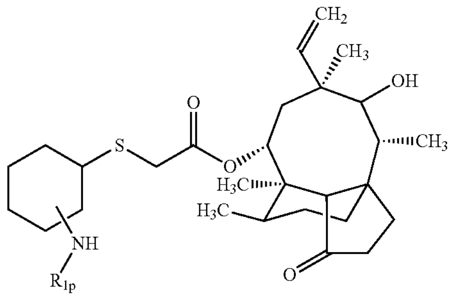

wherein $R_{1p}$ is hydrogen or the residue of an amino acid;

A compound as disclosed in WO0212199, e.g. a compound of formula

IA-WO0212199

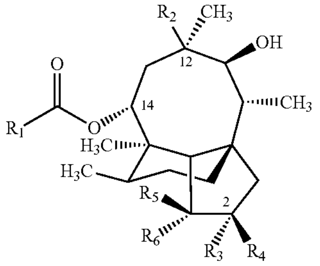

IB-WO0212199

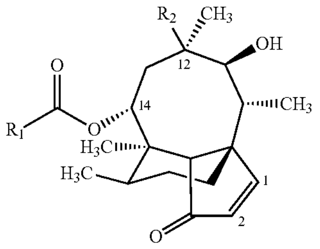

wherein $R_1$ is:

a 5- or 6-membered aromatic or heteroaromatic ring attached via a ring carbon atom, preferably pyridyl, and comprising a substituent selected from halo, $R_7O$—, $R_7S$— or $R_8R_9N$— on a ring carbon adjacent to the carbon of attachment; or a 5- or 6-membered dihydro heteroaromatic ring attached via a ring carbon atom and comprising one oxygen or one or two nitrogen atoms and optionally fused to phenyl, a 5- or 6-membered heteroaryl ring comprising one or two nitrogen atoms or a 5- or 6-membered heterocyclyl ring comprising a sulphur, oxygen or nitrogen atom and further comprising a substituent selected from oxo or thioxo on a ring carbon adjacent to the carbon of attachment;

a 6-membered tetrahydro heteroaromatic ring attached via a ring carbon atom comprising one or two nitrogen atoms and further comprising two substituents independently selected from oxo or thioxo wherein one of the substituents is on a ring carbon adjacent to the carbon of attachment; or a bicyclic heteroyaryl ring attached via a ring carbon atom and comprising nine or ten ring atoms and from one to four nitrogen atoms;

wherein the ring of $R_1$ may be optionally further substituted; $R_2$ is vinyl or ethyl; $R_3$ is H, OH or F and $R_4$ is H, or $R_3$ is H and $R_4$ is F; and $R_5$ and $R_6$ together form an oxo group; or $R_3$ and $R_4$ is each H and $R_5$ is H, or OH and $R_6$ is H, or $R_5$ is H and $R_6$ is H or OH; $R_7$ is optionally substituted $(C_{1-6})$alkyl; and $R_8$ and $R_9$ are independently selected from hydrogen or optionally substituted $(C_{1-6})$alkyl.

A compound as disclosed in WO0222580, of formula

I-WO0222580

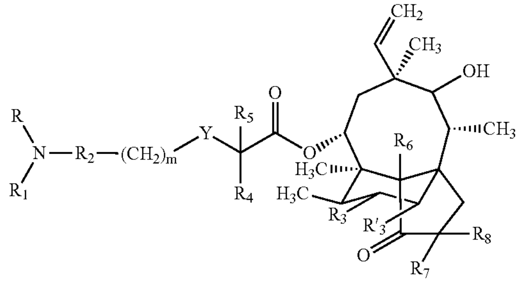

wherein R and $R_2$ together with the nitrogen atom to which they are attached form pyrrolidinyl or piperidinyl, $R_1$ is a group of formula

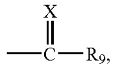

$R_3$ and $R'_3$ are hydrogen, deuterium or halogen, $R_4$ is hydrogen or alkyl, $R_5$ is hydrogen or alkyl, $R_6$, $R_7$ and $R_8$ are hydrogen or deuterium; $R_9$ is amino, alkyl, aryl, heterocyclyl or mercapto; and, if X is oxygen, $R_9$ is additionally hydrogen; $R_{10}$ is hydrogen or alkyl, $R'_{10}$ is alkyl, X is sulphur, oxygen, $NR_{10}$, or $N^+(R'_{10})_2$ in the presence of an appropriate anion, Y is sulphur or oxygen, and m is 0, 1 or 2; with the proviso that, when R and $R_2$ together with the nitrogen atom to which they are attached form piperidinyl, m is 0, Y is S and Y is attached in position 3 of said piperidine ring that group of formula I which is attached to the piperidine ring via the residue Y is either in the (S)-configuration or in the (R)-configuration, preferably in the (S)-configuration; preferably a compound of formula $I_p$-WO0222580

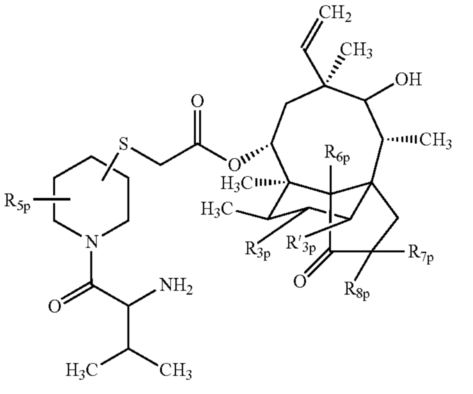

wherein $R_{3p}$, $R'_{3p}$, $R_{6p}$, $R_{7p}$ and $R_{8p}$ are, index-number correspondingly, as defined for a compound of formula I-WO0222580 for $R_3$, $R'_3$, $R_6$, $R_7$ and $R_8$; and $R_{5p}$ is hydrogen or one or more substituents, and if the group attached to the piperidine ring via the sulphur atom is in position 3 of said piperidine ring and $R_{5p}$ is hydrogen, then the group attached to the sulphur atom is either in the (S)-configuration or in the (R)-configuration;

a compound of formula $I_q$-WO0222580

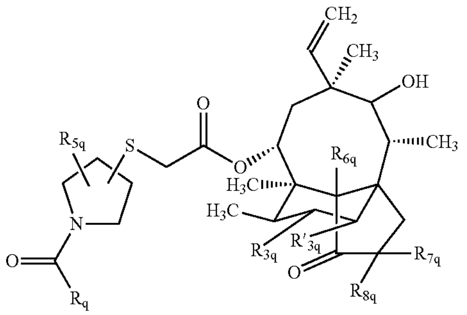

wherein $R_{3q}$, $R'_{3q}$, $R_{6q}$, $R_{7q}$ and $R_{8q}$ are, index-number correspondingly, as defined for a compound of formula I-WO0222580 for $R_3$, $R'_3$, $R_6$, $R_7$ and $R_8$; $R_{5q}$ is hydrogen or one or more substituents, preferably hydrogen; and $R_q$ is that part of an amino acid which remains if the carboxylic group is split off;

a compound of formula $I_r$-WO0222580

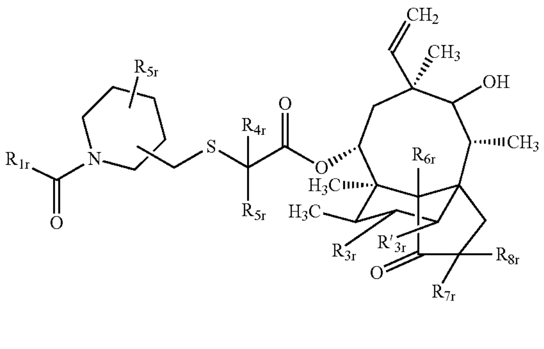

wherein $R_{3r}$, $R'_{3r}$, $R_{4r}$, $R_{6r}$, $R_{7r}$ and $R_{8r}$ are, index-number correspondingly, as defined for a compound of formula WO0222580 for $R_3$, $R'_3$, $R_4$, $R_6$, $R_7$ and $R_8$; $R_{5r}$ is hydrogen or one or more substituents, and $R_{1r}$ is that part of an amino acid which remains if the carboxylic group is split off, or a compound of formula $I_s$-WO0222580

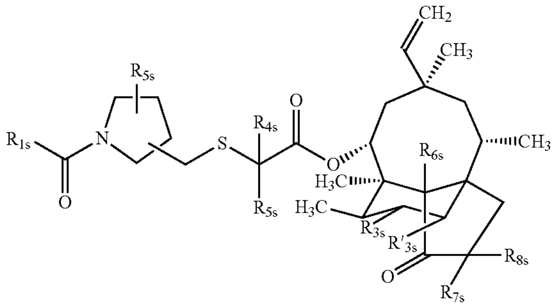

wherein $R_{3s}$, $R'_{3s}$, $R_{4s}$, $R_{6s}$, $R_{7s}$, and $R_{8s}$, respectively, are, index-number correspondingly, as defined for a compound of formula I-WO0222580 for $R_3$, $R'_3$, $R_4$, $R_6$, $R_7$ and $R_8$;

$R_{5s}$ is hydrogen or one or more substituents, preferably hydrogen; and $R_{1s}$ is that part of an amino acid which remains if the carboxylic group is split off; e.g. wherein in a compound of formula $I_s$ the group attached to the piperidine ring via the sulphur atom is either in the (S)-configuration or in the (R)-configuration; e.g. wherein in a group $R_{1s}$ the amine group of the amino acid residue is either in the (S)-configuration or in the (R)-configuration.

Furthermore we have found novel pleuromutilins which show antibacterial activity and activity against *Mycobacterium tuberculosis.*

In another aspect the present invention provides a pleuromutilin, which is selected from the group consisting of compounds of formulae $I_{EX}$

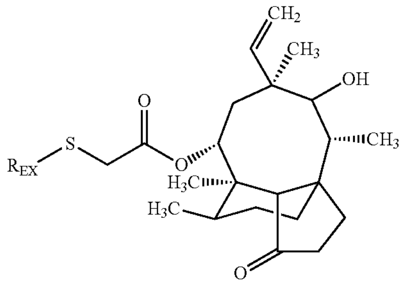

or $I'_{EX}$

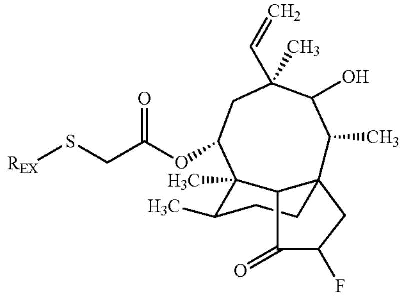

wherein $R_{EX}$ is as set out in TABLE 1. In all Examples of TABLE 1 the compounds are of formula $I_{EX}$, with the exception of Example 12 in which the compound is of formula $I'_{EX}$. $^1$H-NMR-data of the compounds described and obtained according, e.g. analogously, to a method as described in the examples, are also indicated in TABLE 1:

TABLE 1

$R_{EX}$

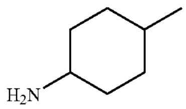

Example 1
14-O-[4-Amino-cyclohexan-1-yl-sulfanyl)-acetyl]-mutilin in the form of a hydrochloride
($d_6$-DMSO): 7.9(b, 3H, $NH_3$), AB-system($\nu_A$ = 3.23, $\nu_B$ = 3.29, 2H, $H_{22}$, J=15.2Hz), 3.03(m, 1H, SCH), 3.10(m, 1H, CHN)

$R_{EX}$

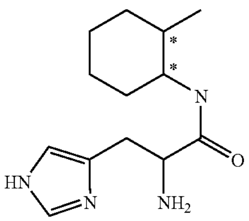

Example 2
14-O-[(2-(R*)-((R)-Histidinyl)-amino-cyclohexan-1-(S*)-yl)-sulfanyl acetyl)]-mutilin in the form of a hydrochloride
($d_6$-DMSO): Diastereoisomers: 8.4, 9.0(2 × m, 2H, NH), 7.5, 8.7 (2 × b, 2H, imidazole), 6.15, 5.1(2 × m, $H_{19}$, $H_{20}$, $H_{21}$), 5.52 (d, 1H, J=5, 2Hz, $H_{14}$), 4.2(m, 1H, a-H-histidine)3.45(m, 1H, $H_{11}$), 3.3(m, 2H, $H_{22}$), 2.7(m, 1H, CHS), 1.18, 1.45 (2 × s, $(CH3)_{15}$, $(CH3)_{18}$), 0.75, 0.88 (2 × d, $(CH_3)_{16}$, $(CH_3)_{17}$, J=5.4Hz)

$R_{EX}$

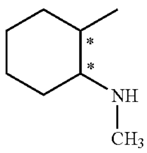

Example 3a
14-O-[2-(R*)-Methylamino-cyclohexan-1-(S*)-yl)-sulfanyl acetyl)]-mutilin
($d_6$-DMSO): Diastereoisomers: 6.15, 5.1(2 × m, $H_{19}$, $H_{20}$, $H_{21}$), 5.52(d, 1H, J=5, 2Hz, $H_{14}$), 4.50(d, 1H, OH, J=5Hz), 3.45(t, 1H, $H_{11}$, J=5Hz), 3.25(m, 2H, $H_{22}$), 3.25(m, 1H, CHN), 2.82(m, 1H, CHS), 2.38(d, 3H, $CH_3NH$, J=5.1Hz), 1.3, 1.34)1.18, 1.45(2 × s, $(CH3)_{15}$, $(CH3)_{18}$), 0.75, 0.88(2 × d, $(CH_3)_{16}$, $(CH_3)_{17}$, J=5.4Hz).

Example 3b
14-O-[(2-(R*)-Methylamino-cyclohexan-1-(R*)-yl)-sulfanyl acetyl)]-mutilin
($d_6$-DMSO): Diastereoisomers: 6.15, 5.1(2 × m, $H_{19}$, $H_{20}$, $H_{21}$), 5.52(d, 1H, J=5, 2Hz, $H_{14}$), 4.50(d, 1H, OH, J=5Hz), 3.45(t, 1H, $H_{11}$, J=5Hz), 3.25(m, 2H, $H_{22}$), 3.25(m, 1H, CHN), 2.65(m, 1H, CHS), 2.43(d, 3H, $CH_3NH$, J=5.1Hz), 1.3, 1.34)1.18, 1.45(2 × s, $(CH3)_{15}$, $(CH3)_{18}$), 0.75, 0.88(2 × d, $(CH_3)_{16}$, $(CH_3)_{17}$, J=5.4Hz)

$R_{EX}$

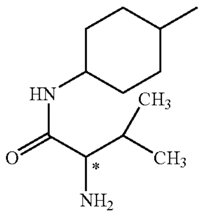

Example 4
(14-O-[4-((R)-Valyl-amino-cyclohexane-1-yl)-sulfanyl)-acetyl]-mutilin in the form of a hydrochloride
($CD_3OD$): 8.3(d, 1H, NH), 8.1(b, 3H, NH3), 6.15(m, 1H, H19), 5.55(d, 1H, H14), 5.05(m, 2H, H20), 3.75(m, 1H, NCHCO), 3.3(m, 1H, NCH), 3.42(d, 1H, H11), 3.25(m, 2H, $SCH_2CO$), 2.98 (m, 1HCHS), 0.9(d, 6H, $(CH_3)_2CH$), 1.08, 1.36(2 × s, 6H, $(CH_3)_{18}$, $(CH_3)_{15}$), 0.65, 0.83(2 × d, 6H, $(CH_3)_{16}$, $(CH_3)_{17}$)

$R_{EX}$

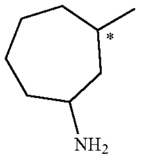

Example 5a
14-O-[((3-(R*)-Amino-cycloheptan-1(R*)-yl)sulfanyl)acetyl]-mutilin and 14-O-[((3-(S*)-amino-cycloheptan-1(S*)-yl)-sulfanyl)-acetyl]mutilin in the form of a hydrochloride (diastereoisomeric mixture)
($d_6$-DMSO): 8.0(b, 3H, $NH_3^+$), 6.15, 5.1(2 × m, $H_{19}$, $H_{20}$, $H_{21}$), 5.52 (d, 1H, J=5, 2Hz, $H_{14}$), 3.1, 3.2(2 × m1H, $CHNH_3^+$), 3.4(m, 1H, $H_{11}$,), 3.3(m, 2H, $H_{22}$), 2.9 (m, 1H, SCH), 1.18, 1.45(2 × s, $(CH3)_{15}$, $(CH3)_{18}$), 0.9 (m, 6H, $CH(CH_3)_2$), 0.75, 0.88(2 × d, $(CH_3)_{16}$, $(CH_3)_{17}$, J=5.4Hz)

Example 5b
14-O-[((3-(R*)-Amino-cycloheptan-1(S*)-yl)sulfanyl)acetyl]-mutilin and 14-O-[((3-(S*)-Amino-cycloheptan-1(R*)-yl)sulfanyl)acetyl]-mutilin in the form of a hydrochloride (diastereoisomeric mixture)
($d_6$-DMSO): 7.8(b, 3H, $NH_3^+$), 6.15, 5.1(2 × m, $H_{19}$, $H_{20}$, $H_{21}$), 5.52(d, 1H, J=5, 2Hz, $H_{14}$), 3.15(2 × m1H, $CHNH_3^+$), 3.4(m, 1H, $H_{11}$,), 3.3(m, 2H, $H_{22}$), 2.95(m, 1H, SCH), 1.18, 1.45(2 × s, $(CH3)_{15}$, $(CH3)_{18}$), 0.9(m, 6H, $CH(CH_3)_2$), 0.75, 0.88 (2 × d, $(CH_3)_{16}$, $(CH_3)_{17}$, J=5.4Hz)

TABLE 1-continued

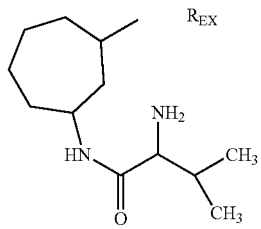

Example 6
14-O-[(3-(R/S)-(R)-Valylamino-1-(R/S)-yl)sulfanyl)acetyl]mutilin in the form of a hydrochloride
($d_6$-DMSO): 8.4(m, 1H, NHC═O), 8.1(b, 3H, $NH_3^+$), 6.15, 5.1 (2 × m, $H_{19}$, $H_{20}$, $H_{21}$), 5.52(d, 1H, J=5, 2Hz, $H_{14}$), 3.5, 3.9(2 × m, 1H, a-H-va-lyl), 3.15(2 × m1H, $CHNH_3^+$), 3.4(m, 1H, $H_{11}$,), 3.3 (m, 2H, $H_{22}$), 2.95(m, 1H, SCH), 1.18, 1.45 (2 × s, $(CH3)_{15}$, $(CH3)_{18}$), 0.9(m, 6H, $CH(CH_3)_2$), 0.75, 0.88 (2 × d, $(CH_3)_{16}$, $(CH_3)_{17}$, J=5.4Hz)

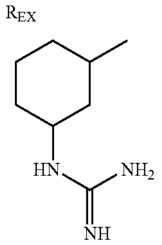

Example 7
14-O-[(3-(R/S)-Guanidino-cyclohexan-1-(R/S)-yl)-acetyl]mutilin-hydrochloride
($d_6$-DMSO): 6.8-7.4(b, 3H, $NH_3^+$), 7.65, 7.7(2 × m, 1H, NH), 6.15, 5.1 (2 × m, $H_{19}$, $H_{20}$, $H_{21}$), 5.52(d, 1H, J=5, 2Hz, $H_{14}$), 4.5(d, 1H, OH, J=6Hz), 3.1(m1H, CHNH), 3.4(t, 1H, $H_{11}$, J=6Hz), 3.3(m, 2H, $H_{22}$), 2.7(m, 1H, SCH), 1.18, 1.45(2 × s,$(CH3)_{15}$, $(CH3)_{18}$), 0.75, 0.88(2 × d, $(CH_3)_{16}$, $(CH_3)_{17}$, J=5.4Hz)

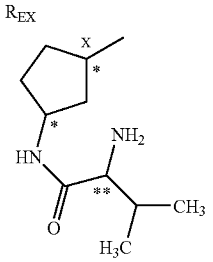

Example 8a
14-O-[3-(R*)-((R)-Valyl-amino-cyclopentan-1-(S*)-yl)-sulfanyl)-acetyl]-mutilin in the form of a hydrochloride
(DMSO-$d_6$): 8.5(d, 1H, NH, J=7.2Hz), 8.1(bs, 3H, $NH_3^+$), 6.15, 5.06, 5.02(3xm, $H_{19}$, $H_{20}$, $H_{21}$), 5.55(d, 1H, $H_{14}$, J=8.2Hz), 4.05 (m, 1H, H-alpha-valyl), 3.15(m, 1H, H-1'), 3.2-3.5(m, H-3', $H_{11}$, $H_{22}$), 1.35, 1.05(2 × s, $(CH_3)_{15}$, $(CH_3)_{18}$), 0.91, 0.88(d, $(CH_3)_2CH$, J=6.8Hz), 0.8, 0.62(2 × d, $(CH_3)_{16}$, $(CH_3)_{17}$, J=6.8Hz)
Example 8b
14-O-[3-(S*)-(R)-Valyl-amino-cyclopentan-1-(R*)-yl)-sulfanyl)-acetyl]-mutilin in the form of a hydrochloride
(DMSO-$d_6$): 8.5(d, 1H, NH, J=7.2Hz), 8.1(bs, 3H, $NH_3^+$), 6.15, 5.06, 5.02(3 × m, $H_{19}$, $H_{20}$, $H_{21}$), 5.55(d, 1H, $H_{14}$, J=8.2Hz), 4.05 (m, 1H, H□-valyl), 3.15(m, 1H, H-1'), 3.2-3.5(m, H3', $H_{11}$, $H_{22}$), 1.35, 1.05(2 × s, $(CH_3)_{15}$, $(CH_3)_{18}$), 0.91, 0.89(d, $(CH_3)_2CH$, J=6.9Hz), 0.8, 0.62(2 × d, $(CH_3)_{16}$, $(CH_3)_{17}$, J=6.8Hz).
Example 8c
14-O-[3-(S*)-((R)-Valyl-amino-cyclopentan-1-(S*)-yl)-sulfanyl)-acetyl]-mutilin and 14-O-[3-(R*)-((R)-valyl-amino-cyclopentan-1-(R*)-yl)-sulfanyl)-acetyl]-mutilin in the form of a hydrochloride (mixture of trans-diastereoisomers)
(DMSO-$d_6$): 8.52, 8.53(2 × d, 1H, NH, J=6.9Hz), 8.1(bs, 3H, $NH_3^+$), 6.15, 6.12, 5.0-5.1(6 × m, $H_{19}$, $H_{20}$, $H_{21}$), 5.54, 5.55(2 × d, 1H, $H_{14}$, J=8.2Hz), 4.15(m, 1H, H□-valyl), 3.1-3.5(m, H-1', H3', $H_{11}$, $H_{22}$), 1.35, 1.05(2 × s, $(CH_3)_{15}$, $(CH_3)_{18}$), 0.91, 0.88(d, $(CH_3)_2CH$, J=6.8Hz), 0.8, 0.62(2 × d, $(CH_3)_{16}$, $(CH_3)_{17}$, J=6.8Hz)

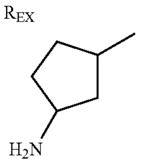

Example 9
14-O-[((3-(R/S)-Amino-cyclopentyl)-sulfanyl)-acetyl]-mutilin-hydrochloride
(DMSO-$d_6$): 8.03(bs, 3H, $NH_3^+$), 6.13, 5.05(2 × m, 3H, $H_{19}$, $H_{20}$, $H_{21}$), 5.55(d, 1H, $H_{14}$, J=8.0Hz), 3.2-3.6(m, H-3', $H_{11}$, $H_{22}$), 3.14(m, 1H, H-1'), 1.35, 1.05(2 × s, $(CH_3)_{15}15$, $(CH_3)_{18}$), 0.8, 0.62 2 × d, $(CH_3)_{16}$, $(CH_3)_{17}$, J=6.8Hz)

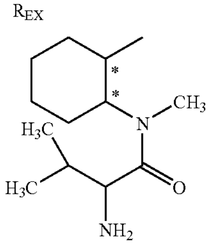

Example 10
14-O-[2-(R*)-((R)-Valyl)-methylamino-cyclohexan-1-(R*)-yl)-sulfanyl acetyl)]-mutilin in the form of a hydrochloride
($d_6$-DMSO): Diastereoisomers: 8.0(m, 3H. $NH_3^+$), 6.15, 5.1 (2 × m, $H_{19}$, $H_{20}$, $H_{21}$), 5.52(d, 1H, J=5, 2Hz, $H_{14}$), 4.50(m, 1H, OH), 4.2 (m, 1H, a-H-valine), 3.45(m, 1H, $H_{11}$), 3.25(m, 2H, $H_{22}$), 3.25, (m, 1H, CHN), 2.82(m, 1H, CHS), 2.88, 2.94 (2 × s, 3H, $CH_3N$), 1.3, 1.34), 1.18, 1.45(2 × s, $(CH3)_{15}$, $(CH3)_{18}$), 0.75, 0.88, (2 × d, $(CH_3)_{16}$, $(CH_3)_{17}$, J=5.4Hz)

TABLE 1-continued

| | |
|---|---|
| $R_{EX}$ 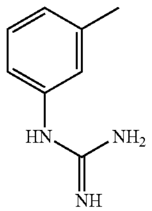 | Example 11 14-O-[(3-Guanidino-phenylsulfanyl)-acetyl]mutilin in the form of a hydrochloride<br>($CDCl_3$): 0.58(d, 3H, $H_{16}$, J=7.2Hz), 0.81 (d, 3H, $H_{17}$, J=7.3Hz),1.02 (s, 3H, $H_{18}$), 1.32 (s, 3H, $H_{15}$), ABX-system($\nu_A$ = 1.2, $\nu_B$ = 1.88, $H_{13a}$, $H_{13b}$, J=16.1Hz, J=9.1Hz), 2.08(d,1H, $H_4$, J=2.1Hz), ABXY-system($\nu_A$ = 2.23, $\nu_B$ = 2.19, $H_{2a}$,$H_{2b}$, J=16.2Hz, J=9.1Hz, J=1.8Hz), 2.3(m,1H,$H_{10}$), 3.4 (d,1H,$H_{11}$, J=5.98Hz), AB-system($\nu_A$ = 3.81, $\nu_B$ = 3.89, 2H, $H_{22}$, J=14.1Hz), 5.18(dd,1H, $H_{20a}$, J=17.5Hz, J=1.6Hz), 5.29(dd,1H, $H_{20b}$, J=11Hz, J=1.6Hz),5.51 (d,1H, $H_{14}$, J=8.3Hz), 6.05 (dd,1H,$H_{19}$,J=11Hz, J=17.5Hz), 7.0 (m, 1H, arom.H), 7.18 (m2H, arom.H), 7.3t,1H, arom.$H_5$, J=8Hz |
| $R_{EX}$ 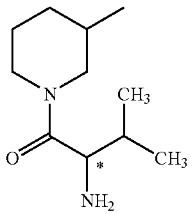 | Example 12 14-O-[(N-(3-Methyl-2(R)-amino-butyryl)-piperidine-3(S)-yl)-sulfanylacetyll-2(S)-fluoro-mutilin in the form of a hydrochloride<br>(DMSO-$d_6$): Rotamers: 7.95 (bs, 3H, $NH_3^+$), 6.12,5.05 (2 × m,$H_{19}$,$H_{20}$,$H_{21}$), 5.56,5.52 (2 × d, 1H,$H_{14}$,J=8.3Hz), 4.92 (ddd, 1H, $H_2$,J=51.3,8.4,8.0Hz), 4.7,4.69 (2 × d,1H,11-OH,J=6.1Hz),4.06 (m,1H,H□-valyl), 4.3,4.25,3.91,3.88,2.6-3,6 (m, 4 × $CH_2N$,SCH,$H_{11}$,$H_{22}$), 1.39,1.06 (2 × s,$(CH_3)_{15}$,$(CH_3)_{18}$), 0.99,0.9,0.84,0.64 (4 × d, $(CH_3)_2CH$,$(CH_3)_{16}$,$(CH_3)_{17}$,J=6.8Hz) |
| $R_{EX}$ 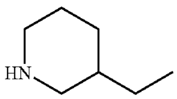 | Example 13 14-O-[((Piperidin-3(S)-yl)methyl-sulfanyl)-acetyl]-mutilin in the form of a hydrochloride<br>($d_6$-DMSO,350K): 6.15, 5.05 (2 × m,$H_{19}$,$H_{20}$,$H_{21}$), 5.55 (d, 1H,5,2Hz, $H_{14}$), 3.4 (d,1H,$H_{11}$,J=5.2Hz), 3.05, 2.95,2.52, 2.31,2.09, (5 × m,4H, $CH_2NCH_2$), 3.2 (m,2H,$SCH_2CO$), 2.48 (m,2H,$CHCH_2S$), 1.18,1.45 (2 × s,$(CH_3)_{15}$,$(CH_3)_{18}$),0.75,0.88,(2 × d,$(CH_3)_{16}$,$(CH_3)_{17}$, J=5.4Hz) |
| $R_{EX}$ 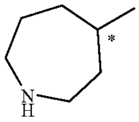 | Example 14 14-O-[((Azepan-4-(R/S)-yl)-sulfanyl acetyl)]-mutilin in the form<br>of a hydrochloride<br>400mg of 14-O-[((N-BOC-azepan-4-(R/S)-yl)-sulfanyl acetyl)-mutilin ($d_6$-DMSO): 8.2-8.5 (b,2H,$NH_2^+$),6.15, 5.1 (2 × m,$H_{19}$,$H_{20}$,$H_{21}$), 5.52(d, 1H,J=5,2Hz,$H_{14}$), 4.52 (d, 1H,OH,J=6.2Hz)3.4(t,1H,$H_{11}$,J=6.2Hz), 3.3 (m,2H,$H_{22}$), 2.9-3.2 (2 × m,3H,SCH, Cl-INCH), 1.18,1.45 (2 × s,$(CH3)_{15}$,$(CH3)_{18}$), 0.75,0.88 (2 × d,$(CH_3)_{16}$,$(CH_3)_{17}$,J=5.4Hz |
| $R_{EX}$ 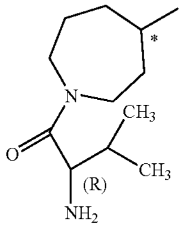 | Example 15 14-O-[((N-(R)-Valyl-azepan-4-(R/S)-yl)-sulfanyl acetyl)]-mutilin-hydrochloride<br>($d_6$-DMSO): 7.7-8.0 (b,3H,$NH_3^+$),6.15, 5.1 (2 × m,$H_{19}$,$H_{20}$,$H_{21}$),5.52(d, 1H,J=5,2Hz,$H_{14}$), 4.52 (d, 1H,OH,J=6.2Hz), 3.4(t, 1H, $H_{11}$,J=6.2Hz), 4.1 (m,a-H-valine), 3.4,2.6(2 × m,4H,$CH_2NCH_2$)3.3 (m,2H,$H_{22}$), 2.9 (m,1H,SCH), 1.18,1.45 (2 × s,$(CH_3)_{15}$,$(CH_3)_{18}$), 0.75,0.88 (2 × d,$(CH_3)_{16}$, $(CH_3)_{17}$,J=5.4Hz) |
| $R_{EX}$ 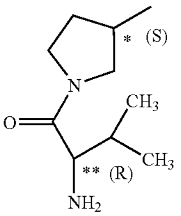 | Example 16 14-O-[(N-(R)-Valyl-pyrrolidin-3(S)-yl)-sulfanyl-acetyl]-mutilin-hydrochloride<br>($CD_3OD$): Rotamer, 8.1(b,3H,$NH_3$), 6.3-6.4(m,1H,H19), 5.75(d,1H, $H_{14}$), 5.15(m,2H,H20), 4.15(m,1H, NCHCO), 3.9(m,1H,NCH),3.6 (m, 1H,NCH),3.42(d,1H,H11), 3.28-3.35(m,2H,$SCH_2CO$), 0.95,0.98 (2 × d, 6H,$(CH_3)_2CH$), 1.08,1.36(2 × s,6H,$(CH_3)_{18}$, $(CH_3)_{15}$), 0.65,0.83 (2 × d,6H, $(CH_3)_{16}$, $(CH_3)_{17}$) |
| $R_{EX}$ 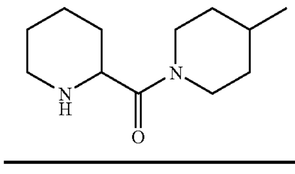 | Example 17 14-O-[((N-(R)-Pipecolyl-piperidin-4-yl)methyl-sulfanyl)-acetyl]-mutilin in the form of a hydrochloride<br>$^1$H-NMR($d_6$-DMSO,350K): 6.15, 5.05 (2 × m,$H_{19}$,$H_{20}$,$H_{21}$), 5.55 (d,1H,5,2Hz,$H_{14}$), 3.35 (d, 1H,$H_{11}$,J=5.2Hz), 4.3 (m,α-H-pipecol), 4.2, 4.05, 3.75 (4 × m,$CH_2NCH_2$), AB-system: 3.12,3.18, J=14.7Hz,$H_{22}$),), 2.8(m,1H,SCH), 1.18,1.45(2 × s,$(CH3)_{15}$, $(CH3)_{18}$), 0.75,0.88 (2 × d,$(CH_3)_{16}$,$(CH_3)_{17}$,J=5.4Hz) |

In another aspect the present invention provides a compound of formula

IA

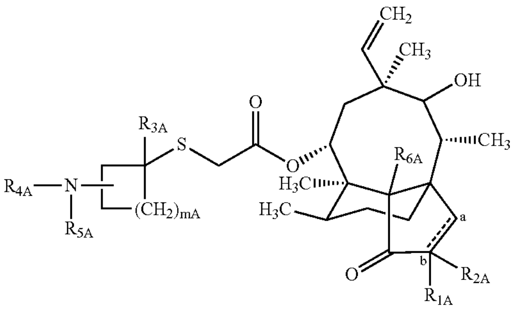

wherein the dotted line is a bond (double bond between positions a=b), $R_{1A}$ is hydrogen and $R_{2A}$ is not present, or the dotted line is no bond (single bond between positions a-b) and $R_{1A}$ and $R_{2A}$ independently of each other are hydrogen, halogen or deuterium, $R_{3A}$ is $(C_{1-6})$alkyl, $R_{4A}$ is hydrogen, $(C_{1-6})$alkyl, a group —C(=NH)—$NH_2$, or the residue of an amino acid, $R_{5A}$ is hydrogen, or $R_{4A}$ and $R_{5A}$ together are a group =CH—$NH_2$, $R_{6A}$ is hydrogen or deuterium, and $m_A$ is 0, 1, 2, 3, 4, or 5.

In a compound of formula IA preferably the dotted line is no bond;

$R_{1A}$ is hydrogen, $R_{2A}$ is hydrogen, $R_{3A}$ is $(C_{1-4})$alkyl, such as methyl, $R_{4A}$ and $R_{5A}$ are as defined above, $R_{6A}$ is hydrogen, and $m_A$ is 2, 3 or 4;

e.g. including pleuromutilins, which are selected from the group consisting of compounds of formula $I_{EX}$

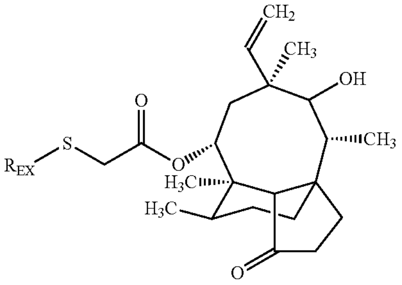

wherein $R_{EX}$ is as set out in TABLE 2. $^1$H-NMR-data of the compounds described and obtained according, e.g. analogously, to a process as described in the examples are also indicated in TABLE 2:

TABLE 2

| | |
|---|---|
| 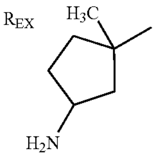 | Example 18 |
| 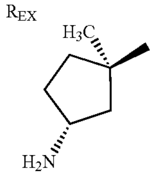 | Example 18a<br>14-O-[(3-(R*)-Amino-1-methyl-cyclopentan-1-(R*)-yl)-sulfanyl)-acetyl]-mutilin and 14-O-[(3-(S*)-amino-1-methyl-cyclopentan-1-(S*)-yl)-sulfanyl)-acetyl]-mutilin in the form of a hydrochloride (mixture of trans-diastereoisomers)<br>(DMSO-$d_6$): 7.98 (bs, 3H, $NH_3^+$), 6.13,5.06,5.03 (3 × m,$H_{19}$,$H_{20}$,$H_{21}$), 5.55 (d, 1H,$H_{14}$,J=8.2Hz), 3.56 (m, 1H,H-3'), 3.3-3.3 (m,$H_{11}$,$H_{22}$), 1.36,1.30,1.29,1.05 (4 × s,9H, $CH_3CS$,$(CH_3)_{15}$,$(CH_3)_{18}$), 0.8,0.62 (2 × d,$(CH_3)_{16}$,$(CH_3)_{17}$,J=6.9Hz) |
| 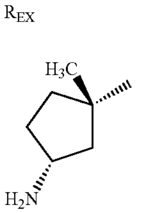 | Example 18b<br>14-O-[(3-(R*)-Amino-1-methyl-cyclopentan-1-(S*)-yl)-sulfanyl)-acetyl]-mutilin and 14-O-[(3-(S*)-Amino-1-methyl-cyclopentan-1-(R*)-yl)-sulfanyl)-acetyl]-mutilin in the form of a hydrochloride (mixture of cis-diastereoisomers)<br>(DMSO-$d_6$): 8.03 (bs, 3H, $NH_3^+$), 6.13,5.06,5.03 (3 × m,$H_{19}$,$H_{20}$,$H_{21}$), 5.53 (d,1H,$H_{14}$,J=8.0Hz), 4.52 (bs,1H-11-OH), 3.51 (m,1H,H-3'), 3.2-3.4 (m,$H_{11}$,$H_{22}$), 1.41,1.40,1.35,1.05 (4 × s,9H,$CH_3CS$ $(CH_3)_{15}$,$(CH_3)_{18}$), 0.8,0.62 (2 × d,$(CH_3)_{16}$,$(CH_3)_{17}$,J=6.9Hz) |
| 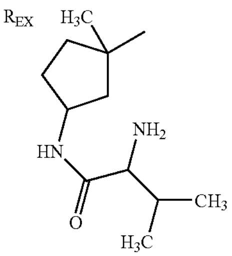 | Example 19 |

TABLE 2-continued

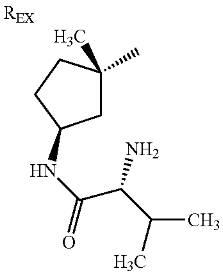

Example 19a
14-O-{[(1S*,3S*)-3-((R)-2-Amino-3-methyl-butyrylamino)-1-methyl-cyclopentylsulfanyl]-acetyl}-mutilin in the form of a hydrochloride
Rotamer 1: (DMSO-$d_6$): 8.48 (d, 1H, NH,J=7.1Hz), 8.1 (bs, 3H, $NH_3^+$), 6.11,5.06,5.03 (3 × m,$H_{19}$,$H_{20}$,$H_{21}$), 5.55 (d,1H,$H_{14}$,J=8.5Hz), 4.15 (m,1H,H□-valyl), 3.1-3.5 (m, H-1',H-3',$H_{11}$,$H_{22}$), 1.35,1.32, 1.05 (3 × s,$CH_3CS$,$(CH_3)_{15}$,$(CH_3)_{18}$), 0.91, 0.88 (d, $(CH_3)_2CH$, J=6.8Hz), 0.8,0.62 (2 × d,$(CH_3)_{16}$,$(CH_3)_{17}$,J=6.8Hz).
Rotamer 2: (DMSO-$d_6$): 8.48 (d, 1H, NH,J=7.1Hz), 8.1 (bs, 3H, $NH_3^+$), 6.11,5.06,5.03 (3 × m,$H_{19}$,$H_{20}$,$H_{21}$), 5.55 (d,1H,$H_{14}$,J=8.5Hz), 4.5 (bs, 1H,1 1-OH), 4.15 (m, 1H,H□-valyl), 3.1-3.5 (m, H-1',H-3',$H_{11}$,$H_{22}$), 1.35,1.32,1.05 (3 × s,$CH_3CS$,$(CH_3)_{15}$,$(CH_3)_{18}$), 0.91, 0.88 (d, $(CH_3)_2CH$,J=6.8Hz), 0.8,0.62 (2 × d,$(CH_3)_{16}$,$(CH_3)_{17}$,J=6.8Hz)

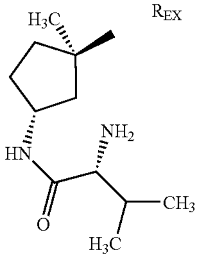

Example 19b
14-O-{[(1R*,3R*)-3-((R)-2-Amino-3-methyl-butrylamino)-1-methyl-cyclopentylsulfanyl]-acetyl}-mutilin-hydrochloride (DMSO-$d_6$): Rotamers: 8.53 (d,1H,NH,J=7.2Hz), 8.1 (bs, 3H, $NH_3^+$), 6.12,5.06,5.03 (3 × m,$H_{19}$,$H_{20}$,$H_{21}$), 5.55 (d, 1H,$H_{14}$,J=8.4Hz), 4.52 (d, 1H,11-OH,J=6.1Hz), 4.25 (m, 1H,H□-valyl), 3.2-3.5 (m, H-1',H-3',$H_{11}$,$H_{22}$), 1.42,1.39,1.35,1.05 (4 × s,9H,$CH_3CS$,$(CH_3)_{15}$, $(CH_3)_{18}$), 0.91, 0.88 (d, $(CH_3)_2CH$,J=6.8Hz), 0.8,0.62 (2 × d,$(CH_3)_{16}$, $(CH_3)_{17}$,J=6.8Hz)

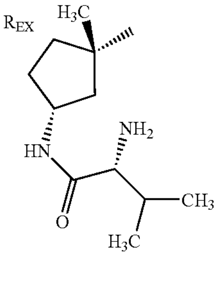

Example 19c
14-O-{[(1R*,3S*)-3-((R)-2-Amino-3-methyl-butyrylamino)-1-methyl-cyclopentylsulfanyl]-acetyl}-mutilin and
14-O-{[(1S*,3R*)-3-((R)-2-Amino-3-methyl-butyrylamino)-1-methyl-cyclopentylsulfanyl]-acetyl}-mutilin in the form of a hydrochloride (mixture of cis-diastereoisomers)
(DMSO-$d_6$): 8.4,8.3 (2 × d, 1H, NH,J=7.2Hz), 8.17 (bs, 3H, $NH_3^+$), 6.12,5.06,5.02 (3 × m,$H_{19}$,$H_{20}$,$H_{21}$), 5.55 (d,1H,$H_{14}$,J=8.3Hz), 4.53 (bs,1H,11-OH), 4.15 (m,1H,H□-valyl), 3.2-3.5 (m, H-1',H-3',$H_{11}$, $H_{22}$), 1.36,1.35,1.32,1.05 (4 × s,9H,$CH_3CS$,$(CH_3)_{15}$,$(CH_3)_{18}$), 0.92, 0.91,0.89,0.88 (2 × d,6H,$(CH_3)_2CH$,J=6.8Hz), 0.8,0.62 (2 × d, $(CH_3)_{16}$,$(CH_3)_{17}$, J=6.8Hz)

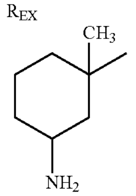

Example 20
14-O-[((3-(R/S)-Amino-cyclohexan-1-(R/S)-methyl-1-yl)sulfanyl) acetyl]mutilin in the form of a hydrochloride
($d_6$-DMSO): Rotamers: 7.90(b,3H,$NH_3^+$), 6.15, 5.1 (2 × m,$H_{19}$,$H_{20}$, $H_{21}$), 5.52(d,1H,J=5,2Hz,$H_{14}$), 4.5 (2 × d, 1H,OH,J=6Hz), 3.4(t, 1H, $H_{11}$,J=6Hz), 3.3 (m,2H,$H_{22}$), 3.1 (m,1H,NCH), 1.2,1.25 (2 × s,3H, $CH_3CS$)-1.18,1.45(2 × s,$(CH3)_{15}$,$(CH3)_{18}$), 0.9 (m,6H,$CH(CH_3)_2$), 0.75,0.88 (2 × d,$(CH_3)_{16}$,$(CH_3)_{17}$,J=5.4Hz)

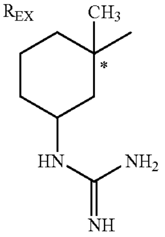

Example 21a
14-O-[(3-(R*)-Guanidino-cyclohexan-1-(R*)-methyl-1-yl)-acetyl]mutilin in the form of a hydrochloride + 14-O-[(3-(S*)-Guanidino-cyclohexan-1-(S*)-methyl-1-yl)-acetyl]mutilin in the form ofa hydrochloride
($d_6$-DMSO): 10.7,8.6,7.65,(3 × m,2H,NH),6.7-7.5(b,2HNH), 6.15, 5.1 (2 × m,$H_{19}$,$H_{20}$,$H_{21}$), 5.52(d,1H,J=5,2Hz,$H_{14}$), 5.5 (d,1H,OH,J=6Hz), 3.9,3.6(2x,m1H, CHNH), 3.4(t,1H,$H_{11}$,J=6Hz), 3.3 (m,2H,$H_{22}$), 1.4,1.45(2 × s,3H,$CH_3CS$), 1.18,1.45(2 × s,$(CH3)_{15}$,$(CH3)_{18}$), 0.75,0.88 (2 × d,$(CH_3)_{16}$,$(CH_3)_{17}$,J=5.4Hz).
Example 21 b
methyl-1-yl)-acetyl]mutilin in the form of a hydrochloride + 14-O-[(3-(S*)-Guanidino-cyclohexan-1-(R*)-methyl-1-yl)-acetyl]mutilin in the form of a hydrochloride
($d_6$-DMSO): 10.7,8.6,7.65,(3 × m,2H,NH),6.7-7.5(b,2HNH), 6.15, 5.1 (2 × m,H1 9,$H_{20}$,$H_{21}$), 5.52(d, 1H,J=5,2Hz,$H_{14}$), 5.5 (d, 1H,OH,J=6Hz), 3.9,3.6(2x,m1H, CHNH), 3.4(t,1H,J=6Hz), 3.3 (m,2H,$H_{22}$), 1.4,1.45(2 × s,3H,$CH_3CS$), 1.18,1.45(2 × s,$(CH_3)_{15}$,$(CH_3)_{18}$), 0.75,0.88 (2 × d,$(CH_3)_{16}$,$(CH_3)_{17}$,J=5.4Hz)

TABLE 2-continued

| | |
|---|---|
| 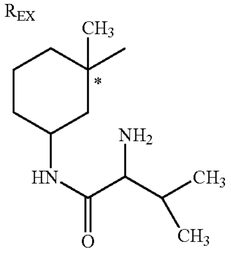 | Example 22a<br>14-O-[(3-(R*)-(R)-Valylamino-1-(R*)-methyl-1-yl)sulfanyl)-acetyl]mutilin and 14-O-[(3-(S*)-(R)-Valylamino-1-(S*)-methyl-1-yl)sulfanyl)-acetyl]mutilin in the form of a hydrochloride (diastereoisomeric mixture)<br>($d_6$-DMSO): 8.3(m,1H,NHC═O),8.1(b,3H,$NH_3^+$), 6.15, 5.1 (2 x m, $H_{19}$,$H_{20}$,$H_{21}$), 5.52(d, 1H,J=5,2Hz,$H_{14}$), 3.9 (m,1H,a-H-valyl), 3.3-3.1 (4 x m,4H,$H_{11}$, $H_{22}$,,CH$NH_3^+$), 4.5 (b,1H,OH), 1.25 (b,3H,$CH_3$CS), 1.18,1.45(2 x s,$(CH3)_{15}$,$(CH3)_{18}$), 0.9 (m,6H,CH$(CH_3)_2$), 0.75,0.88 (2 x d,$(CH_3)_{16}$,$(CH_3)_{17}$,J=5.4Hz)<br>Example 22b<br>14-O-[(3-(R*)-(R)-Valylamino-1-(S*)-methyl-1-yl)sulfanyl)-acetyl]mutilin and 14-O-[(3-(S*)-(R)-Valylamino-1-(R*)-methyl-1-yl)sulfanyl)-acetyl]mutilin in the form of a hydrochloride (diastereoisomeric mixture)<br>($d_6$-DMSO): 8.35( m,1H,NHCO),8.1(b,3H,$NH_3^+$), 6.15, 5.1 (2 x m, $H_{19}$,$H_{20}$,$H_{21}$), 5.52(d, 1H,J=5,2Hz,$H_{14}$), 3.95 (m, 1H, a-H-valyl), 3.75 (m,1H,CHNH), 3.2-3.5(3 x m,3H, $H_{11}$, $H_{22}$,), 4.5 (b, 1H,OH), 1.25 (b,3H,$CH_3$CS), 1.18,1.45(2 x s,$(CH_3)$,5,$(CH_3)_{18}$), 0.9 (m,6H, CH$(CH_3)_2$), 0.75,0.88 (2 x d,$(CH_3)_{16}$,$(CH_3)_{17}$,J=5.4Hz) |
| 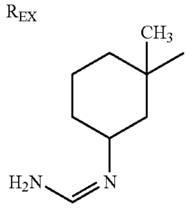 | Example 23<br>14-O-[(3-(R/S)-Dimethylamino-methylenimino-cyclohexan-1-(R/S)-methyl-1-yl)-acetyl]mutilin in the form of a hydrochloride<br>($d_6$-DMSO): 9.2,8.1 (2 x b,2H,NH), 6.15, 5.1 (2 x m,$H_{19}$,$H_{20}$,$H_{21}$), 5.52 (d, 1H,J=5,2Hz,$H_{14}$), 4.5 (d, 1H,OH,J=6Hz), 3.7(,m1H, CHNH), 3.4 (t,1H,$H_{11}$,J=6Hz), 3.3 (m,2H,$H_{22}$),3.1(b,6H,N$(CH_3)_2$), 1.4,1.45 (2 x s, 3H,$CH_3$CS), 1.18,1.45(2 x s,$(CH3)_{15}$,$(CH3)_{18}$), 0.75,0.88 (2 x d, $(CH_3)_{16}$,$(CH_3)_{17}$,J=5.4Hz) |

In another aspect the present invention provides 14-O-(oximino-($C_{3-8}$)cycloalkyl-sulfanylmethylcarbonyl)-pleuromutilins and 14-O-(hydrazono-($C_{3-8}$)cycloalkyl-sulfanylmethylcarbonyl)-pleuromutilins, such as a compound of formula

IB

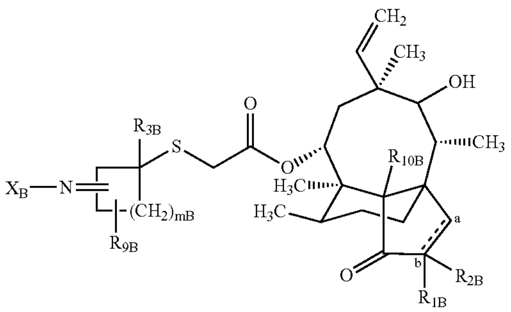

wherein $R_{1B}$ has the meaning of $R_{1A}$ as defined above,
$R_{2B}$ has the meaning of $R_{2A}$ as defined above,
$R_{10B}$ has the meaning of $R_{6A}$ as defined above,
the dotted line has the meaning as defined above,
$m_B$ has the meaning of $m_a$ as defined above,
$R_{3B}$ is hydrogen or $(C_{1-6})$alkyl,
$X_B$ is —O—$R_{4B}$ or —$NR_{5B}R_{6B}$,
$R_{4B}$ is hydrogen or $(C_{1-6})$alkyl, optionally substituted by a group —$NR_{7B}R_{8B}$,
$R_{5B}$ and $R_{6B}$ independently of each other are $(C_{1-4})$alkyl,
$R_{7B}$ and $R_{8B}$ independently of each other are $(C_{1-4})$alkyl, or $R_{7B}$ and $R_{8B}$ together with the nitrogen atom to which they are attached form aliphatic heterocyclyl, having 5 to 8 ring members, and
$R_{9B}$ is hydrogen or $(C_{1-4})$alkyl.

In a compound of formula $I_B$ preferably
$R_{1B}$ has is hydrogen,
$R_{2B}$ has is hydrogen,
the dotted line is not present (single bond),
$m_B$ is 2, 3 or 4,
$R_{3B}$ is hydrogen or $(C_{1-4})$alkyl, such as methyl,
$X_B$ is as defined above,
$R_{4B}$ is hydrogen or $(C_{1-4})$alkyl, such as ethyl, substituted by a group —$NR_{7B}R_{8B}$,
$R_{5B}$ and $R_{6B}$ are as defined above,
$R_{7B}$ and $R_{8B}$ independently of each other are $(C_{1-4})$alkyl, e.g. ethyl, or $R_{7B}$ and $R_{8B}$ together with the nitrogen atom to which they are attached form pyrrolidine or piperidine,
$R_{9B}$ is as defined above, and
$R_{10B}$ is hydrogen;
e.g. including 14-O-(oximino-($C_{3-8}$)cycloalkyl-sulfanylmethylcarbonyl)-pleuromutilins and 14-O-(hydrazono-($C_{3-8}$)cycloalkyl-sulfanylmethylcarbonyl)-pleuromutilins, which are selected from the group consisting of compounds of formula $I_{EX}$

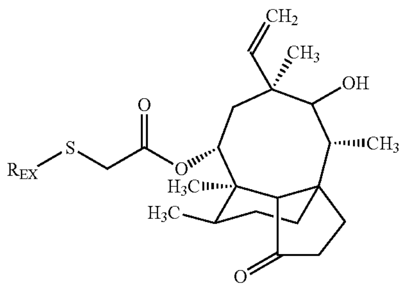

wherein $R_{EX}$ is as set out in TABLE 3. $^1$H-NMR-data of the compounds described and obtained according, e.g. analogously, to a process as described in the examples, are also indicated in TABLE 3:

TABLE 3

| | |
|---|---|
| 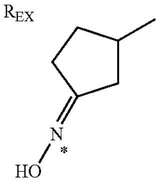 | Example 24<br>14-O-{[(3-Hydroxyimino-cyclopentan-(R/S)-yl)-sulfanyl]-acetyl}-mutilin (syn and anti forms)<br>Syn*-form: (DMSO-$d_6$): 10.33 (s, 1H,═NOH), 6.15,5.07,5.03 (3 × m,$H_{19}$,$H_{20}$,$H_{21}$), 5.55 (d,1H,$H_{14}$,J=8.3Hz), 4.5 (d,1H,11-OH, J=6.1Hz), 3.25-3.45 (m, SCH, $H_{11}$, $H_{22}$), 2.67 (m,1H,H-2a'), 1.35,1.05 (2 × s,$(CH_3)_{15}$,$(CH_3)_{18}$), 0.8,0.62 (2 × d,$(CH_3)_{16}$, $(CH_3)_{17}$,J=7Hz).<br>Anti*-form: (DMSO-$d_6$): 10.36 (s,1H,NOH), 6.15,5.07,5.02 (3 × m,$H_{19}$,$H_{20}$,$H_{21}$), 5.55 (d,1H,$H_{14}$,J=8.3Hz), 4.5 (d,1H, 11-OH,J=6.1Hz), 3.25-3.45 (m, SCH, $H_{11}$, $H_{22}$), 2.74 (m,1H,H-2a') 1.35,1.05 (2 × s,$(CH_3)_{15}$,$(CH_3)_{18}$), 0.8,0.62 (2 × d,$(CH_3)_{16}$, $(CH_3)_{17}$,J=6.8Hz) |
| 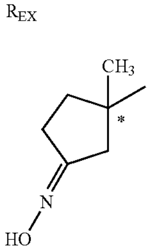 | Example 25a<br>14-O-{[(3-(E/Z)-Hydroxyimino-1-methyl-cyclopentan-(R*)-yl)-sulfanyl]-acetyl}-mutilin<br>$^1$HNMR(DMSO-$d_6$): 10.33, 10.28 (2 × s, 1H,═NOH), 6.15,5.07,5.02 (3 × m,$H_{19}$,$H_{20}$,$H_{21}$),5.55,5.53 (2 × d, 1H,$H_{14}$,J=8.3Hz),4.5,4.48 (2 × d, 1H, 11-OH,J=6.0Hz), 3.20-3.45 (m, SCH, $H_{11}$, $H_{22}$),1.35,1.05 (3 × s, $CH_3CS$, $(CH_3)_{15}$,$(CH_3)_{18}$), 0.8,0.62 (2 × d,$(CH_3)_{16}$,$(CH_3)_{17}$,J=6.9Hz)<br>Example 25b<br>14-O-{[(3-(E/Z)-Hydroxyimino-1-metyhyl-cyclopentan-(S*)-yl)-sulfanyl]-acetyl}-mutilin<br>(DMSO-$d_6$): 10.32, 10.27 (2 × s,1H,NOH), 6.15,5.07,5.02 (3 × m,$H_{19}$,$H_{20}$,$H_{21}$), 5.55 (d, 1H,$H_{14}$,J=8.3Hz), 4.5 (d,1H, 11-OH, J=6.1Hz), 3.20-3.45 (m, SCH, $H_{11}$, $H_{22}$), 1.35,1.05 (3 × s,$CH_3CS$, $(CH_3)_{15}$,$(CH_3)_{18}$), 0.8,0.62 (2 × d,$(CH_3)_{16}$,$(CH_3)_{17}$,J=6.8Hz) |
| 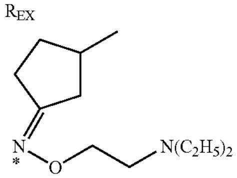 | Example 26<br>14-O-{[(3-(2-Diethylamino-ethoxyimino)-cyclopentan-(R/S)-yl)-sulfanyl]-acetyl}-mutilin in the form of a hydrochloride (syn/anti mixture)<br>(DMSO-$d_6$): 9.9 (bs, 1H,$NH^+$), 6.15,5.07,5.03 (3 × m,$H_{19}$,$H_{20}$,$H_{21}$), 5.55 (d,1H,,$H_{14}$,J=8.1Hz), 4.3 (m,2H,$OCH_2$), 3.1-3.4 (m, $NCH_2$, $H_{11}$, $H_{22}$), 1.35,1.05 (2 × s,$(CH_3)_{15}$,$(CH_3)_{18}$), 0.8,0.62 (2 × d,$(CH_3)_{16}$,$(CH_3)_{17}$,J=6.8Hz) |
| 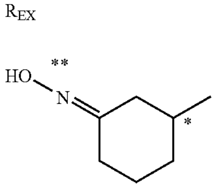 | Example 27a<br>14-O-[((E*-Hydroximino-cyclohexan-3-(R*)-yl)-sulfanyl)-acetyl]mutilin<br>($d_6$-DMSO): 10.31 (s, 1H,HON═C), 6.15, 5.1 (2 × m,$H_{19}$,$H_{20}$,$H_{21}$), 5.52 (d,1H,J=5,2Hz,$H_{14}$), 4.55 (d, 1H,OH,J=5Hz)3.4(t, 1H,$H_{11}$,J=5Hz), 3.3 (m,2H,$H_{22}$), 2.95 (m,1H,SCH), 2.78, 1.95 (2 × m,2H,$CH_2C$═N), 2.57,2.09(2 × m,2H,$CH_2$═C═N), 1.18,1.45 (2 × s,$(CH3)_{15}$,$(CH3)_{18}$), 0.75,0.88 (2 × d,$(CH_3)_{16}$,$(CH_3)_{17}$,J=5.4Hz).<br>$[\alpha]_D$ = 15.87°(c = 1,MeOH)<br>Example 27b<br>14-O-[((E*-Hydroximino-cyclohexan-3-(S*)-yl)-sulfanyl)-acetyl]mutilin<br>($d_6$-DMSO): 10.31 (s, 1H,HON═C), 6.15, 5.1 (2 × m,$H_{19}$,$H_{20}$,$H_{21}$), 5.52 (d,1H,J=5,2Hz,$H_{14}$), 4.50 (d,1H,OH,J=5Hz) 3.4(t, 1H,$H_{11}$, J=5Hz), 3.3 (m,2H,$H_{22}$), 2.95 (m, 1H,SCH),2.78, 1.95(2 × m, 2H, $CH_2$═C═N), 2.57,2.09(2 × m,2H,$CH_2$═C═N), 1.18,1.45 (2 × s,$(CH_3)_{15}$, $(CH_3)_{18}$), 0.75,0.88 (2 × d,$(CH_3)_{16}$,$(CH_3)_{17}$,J=5.4Hz). $[\alpha]_D$ = 38.5°(c = 1,MeOH)<br>Example 27c<br>14-O-[((Z*-Hydroximino-cyclohexan-3-(R*)-yl)-sulfanyl)-acetyl]mutilin<br>($d_6$-DMSO): 10.31(s,1H,HON═C), 6.15, 5.1 (2 × m,$H_{19}$, $H_{20}$, $H_{21}$), 5.52 (d, 1H,J=5,2Hz,$H_{14}$), 4.50 (d,1H,OH,J=5Hz),3.45 (t,1H, $H_{11}$, J=5Hz), 3.3 (m,2H,$H_{22}$), 2.90(m, 1H,SCH), 3.05,2.05 (2 × m, 2H, $CH_2$═C═N), 2.2(m,2H,$CH_2$═C═N), 1.18,1.45(2 × s,$(CH_3)_{15}$, $(CH3)_{18}$), 0.75,0.88 (2 × d,$(CH_3)_{16}$,$(CH_3)_{17}$, J=5.4Hz). $[\alpha]_D$ = 13.62°(c = 1,MeOH)<br>Example 27d<br>14-O-[((Z*-Hydroximino-cyclohexan-3-(S*)-yl)-sulfanyl)acetyl]mutilin<br>($d_6$-DMSO): 10.31 (s, 1H,HON═C), 6.15, 5.1 (2 × m,$H_{19}$,$H_{20}$,$H_{21}$), 5.52 (d,1H,J=5,2Hz,$H_{14}$), 4.50 (d, 1H,OH,J=5Hz),3.45(t, 1H, $H_{11}$,J=5Hz), 3.3 (m,2H,$H_{22}$), 2.90(m, 1H,SCH), 3.05,2.05 (2 × m, 2H,$CH_2C$═N), 2.2(m,2H,$CH_2$═C═N), 1.18,1.45 (2 × s,$(CH_3)_{15}$, $(CH3)_{18}$), 0.75,0.88 (2 × d,$(CH_3)_{16}$,$(CH_3)_{17}$,J=5.4Hz).<br>$[\alpha]_D$ = 42.83°(c = 1,MeOH) |

TABLE 3-continued

| | |
|---|---|
| 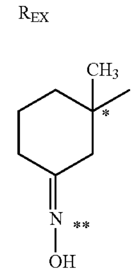 | Example 28a<br>14-O-[((E-Hydroximino-cyclohexan-3-(R/S)-methyl-1-yl)-sulfanyl)acetyl]mutilin<br>($d_6$-DMSO): 10.31(s, 1H,HON=C), 6.15, 5.1 (2 × m,$H_{19}$,$H_{20}$,$H_{21}$), 5.52 (d, 1H,J=5,2Hz,$H_{14}$), 4.50 (d, 1H,OH,J=5Hz),3.45(t, 1H,$H_{11}$, J=5Hz), 3.25(m,2H,$H_{22}$), 1.25 (s,3H,$CH_3$, $CH_3CS$) 1.18,1.45 (2 × s,$(CH_3)$i 5,$(CH_3)_{18}$), 0.75,0.88 (2 × d,$(CH_3)_{16}$,$(CH_3)_{17}$,J=5.4Hz)<br>Example 28b<br>14-O-[((Z-Hydroximino-cyclohexan-3-(R/S)-methyl-1-yl)-sulfanyl)acetyl]mutilin<br>($d_6$-DMSO): 10.31(s, 1H,HON=C), 6.15,5.1 (2 × m,$H_{19}$,$H_{20}$,$H_{21}$), 5.52 (d,1H,J=5,2Hz,$H_{14}$), 4.50 (d,1H,OH,J=5Hz),3.45 (t,1H, $H_{11}$, J=5Hz), 3.25(m,2H,$H_{22}$), 2.7 (d,1H,CHC=N, J=12Hz),1.25 (s,3H, $CH_3$, $CH_3CS$) 1.18,1.45 (2 × s,$(CH_3)_{15}$,$(CH_3)_{18}$), 0.75,0.88 (2 × d, $(CH_3)_{16}$,$(CH_3)_{17}$,J=5.4Hz) |
| 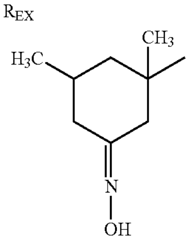 | Example 29<br>14-O-[((Z/E-Hydroximino-cyclohexan-3-(R/S)-methyl-5-(R/S)-methyl-1-yl)-sulfanyl)acetyl]mutilin<br>($d_6$-DMSO): Diastereoisomers: 10.2,10.28(3 × s, 1H,HON=C), 6.15, 5.1 (2 × m,$H_{19}$,$H_{20}$,$H_{21}$), 5.52 (d,1H,J=5,2Hz,$H_{14}$), 4.50 (d, 1H,OH, J=5Hz),3.45(t,1H,$H_{11}$,J=5Hz), 3.25(m,2H,$H_{22}$), 3.25,1.7 (2 × m, 2H,$CH_2C$=N), 1.3,1.34 (2 × s,3H,$CH_3$, $CH_3CS$),1.18,1.45 (2 × s, $(CH3)_{15}$,$(CH3)_{18}$), 0.75,0.88 (2 × d,$(CH_3)_{16}$,$(CH_3)_{17}$,J=5.4Hz).<br>MS-ESI: 534 (M + 1) |
| 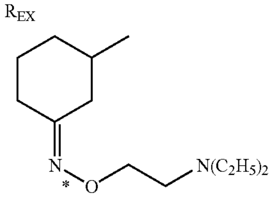 | Example 30<br>14-O-{[(3-(2-Diethylamino-ethoxyimino)-cyclohexan-(R/S)-yl)-sulfanyl]-acetyl}-mutilin hydrochloride (E/Z mixture)<br>(DMSO-$d_6$): 9.7 (bs, 1H,$NH^+$), 6.15,5.07,5.03 (3 × m,$H_{19}$;$H_{20}$,$H_{21}$), 5.55 (d, 1H,,$H_{14}$,J=8.0Hz), 4.5,4.25 (2 × m,2H,$OCH_2$), 3.0-3.45 (m, $NCH_2$, $H_{11}$, $H_{22}$), 1.35,1.05 (2 × s,$(CH_3)_{15}$,$(CH_3)_{18}$), 0.8,0.62 (2 × d,$(CH_3)_{16}$,$(CH_3)_{17}$,J=6.8Hz) |
| 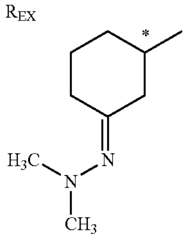 | Example 31<br>14-O-[(((E/Z)-Dimethylaminimino-cyclohexan-3-(R/S)-1-yl)-sulfanyl)acetyl]mutilin<br>($d_6$-DMSO): Diastereoisomers: 6.15, 5.1 (2 × m,$H_{19}$,$H_{20}$,$H_{21}$), 5.52 (d,1H,J=5,2Hz,$H_{14}$), 4.50 (d, 1H,OH,J=5Hz),3.45(t,1H,$H_{11}$,J=5Hz), 3.3(m,2H,$H_{22}$), 3.2, 2.8 (2 × m, 1H,CHS), 2.95,1.85 (2 × m,2H, $CH_2C$=N), 1.18,1.45 (2 × s,$(CH3)_{15}$,$(CH3)_{18}$), 0.75,0.88 (2 × d, $(CH_3)_{16}$,$(CH_3)_{17}$,J=5.4Hz) |
| 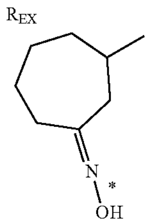 | Example 32a<br>14-O-[((E*-Hydroximinocycloheptan-3-(R/S)-yl)-sulfanyl)-acetyl]mutilin<br>NMR($d_6$-DMSO): 10.35(s,1H, HON=C), 6.15, 5.1 (2 × m,$H_{19}$,$H_{20}$, $H_{21}$), 5.52 (d, 1H,J=5,2Hz,$H_{14}$), 4.5(d,1H,OH,J=6.1Hz), 3.4(t, 1H,$H_{11}$,J=6.1Hz)), 3.3 (m,2H,$H_{22}$), 1.18,1.45(2 × s,$(CH3)_{15}$, $(CH3)_{18}$), 0.75,0.88 (2 × d,$(CH_3)_{16}$, $(CH_3)_{17}$, J=5.4Hz).<br>Example 32b<br>14-O-[((Z*-Hydroximino-cycloheptan-3-(R/S)-yl)-sulfanyl)acetyl]mutilin<br>($d_6$-DMSO): 10.35(s, 1H,HON=C), 6.15, 5.1 (2 × m,$H_{19}$,$H_{20}$,$H_{21}$), 5.52(d, 1H,J=5,2Hz,$H_{14}$), 4.5 (d, 1H,OH,J=5Hz)3.4(t, 1H,$H_{11}$, J=5Hz), 3.3 (m,2H,$H_{22}$), 3.05 (m,1H,SCH), 1.18,1.45(2 × s,$(CH3)_{15}$, $(CH3)_{18}$), 0.75,0.88 (2 × d,$(CH_3)_{16}$,$(CH_3)_{17}$,J=5.4Hz) |
| 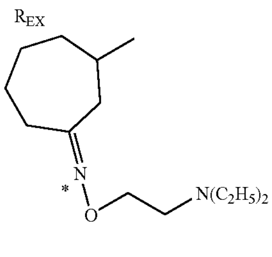 | Example 33<br>14-O-{[(3-(2-Diethylamino-ethoxyimino)-cyclohept-(R/S)-yl)-sulfanyl]-acetyl}-mutilin hydrochloride (E/Z mixture)<br>(DMSO-$d_6$): 9.85 (bs, 1H,$NH^+$), 6.15,5.06,5.03 (3 × m,$H_{19}$,$H_{20}$,$H_{21}$), 5.55 (d,1H,$H_{14}$,J=8.5Hz), 4.52,4.53 (2 × d,1H,11-OH,J=6.2Hz), 4.28 (m,2H,$OCH_2$), 3.0-3.45 (m, $NCH_2$, $H_{11}$, $H_{22}$), 1.35,1.05 (2 × s,$(CH_3)_{15}$,$(CH_3)_{18}$), 0.8,0.62 (2 × d,$(CH_3)_{16}$,$(CH_3)_{17}$,J=6.8Hz) |

TABLE 3-continued

| | |
|---|---|
| 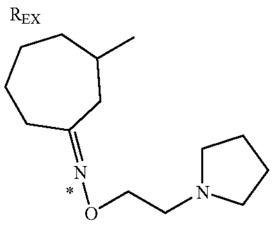 | Example 34<br>14-O-{[(3-(2-Pyrrolinine-1-yl-ethoxyimino)-cyclohept-1-(R/S)-yl)-sulfanyl]-acetyl}-mutilin hydrochloride (E/Z mixture)-<br>(DMSO-$d_6$): 10.2 (bs,1H,$NH^+$), 6.15,5.08,5.05<br>(3 x m,$H_{19}$,$H_{20}$,$H_{21}$), 5.58 (d,1H,$H_{14}$,J=8.3Hz), 4.53,4.57<br>(2 x d,1H,11-OH,J=6.1Hz), 4.26 (m,2H,$OCH_2$), 3.0-3.45 (m, $NCH_2$, $H_{11}$, $H_{22}$), 1.38,1.08 (2 x s,$(CH_3)_{15}$,$(CH_3)_{18}$), 0.83,0.64<br>(2 x d,$(CH_3)_{16}$,$(CH_3)_{17}$,J=6.8Hz). |
| 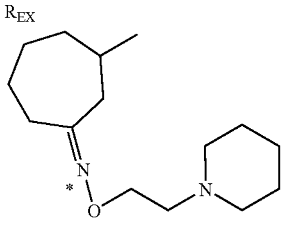 | Example 35<br>14-O-{[(3-(2-Piperidine-1-yl-ethoxyimino)-cyclohept-(R/S)-yl)-sulfanyl]-acetyl}-mutilin in the form of a hydrochloride (E/Z mixture)<br>$^1$HNMR(DMSO-$d_6$): 10.0 (bs,1H,$NH^+$), 6.15,5.06,5.03<br>(3 x m,$H_{19}$,$H_{20}$,$H_{21}$), 5.55 (d,1H,$H_{14}$,J=8.4Hz), 4.5,4.55<br>(2 x d,1H,11-OH,J=6.2Hz), 4.32 (m,2H,$OCH_2$), 2.8-3.5 (m, $NCH_2$, $H_{11}$, $H_{22}$), 1.35,1.05 (2 x s,$(CH_3)_{15}$,$(CH_3)_{18}$), 0.8,0.62<br>(2 x d,$(CH_3)_{16}$,$(CH_3)_{17}$,J=6.8Hz) |

In another aspect the present invention provides a compound of formula

IC

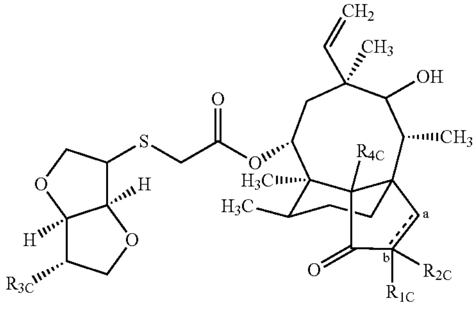

wherein $R_{1C}$ has the meaning of $R_{1A}$ as defined above, $R_{2C}$ has the meaning of $R_{2A}$ as defined above, the dotted line has the meaning as defined above, $R_{4C}$ has the meaning of $R_{6A}$ as defined above, and $R_{3C}$ is amino, $(C_{1-4})$alkylamino, di$(C_{1-4})$alkylamino, the residue of an amino acid, hydroxy, or $(C_{1-4})$alkoxy.

In a compound of formula $I_C$ preferably $R_{1C}$ is hydrogen, $R_{2C}$ is hydrogen, $R_{4C}$ is hydrogen, the dotted line is not present (single bond), and $R_{3C}$ is amino, di$(C_{1-4})$alkylamino, or the residue of an amino acid;

e.g. including pleuromutilins which are selected from the group consisting of compounds of formula $I_{EX}$

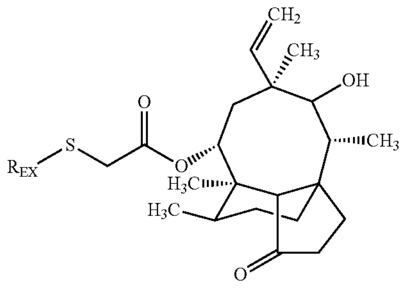

wherein $R_{EX}$ is as set out in TABLE 4. $^1$H-NMR-data of the compounds described and obtained according, e.g. analogously, to a process as described in the examples are also indicated in TABLE 4:

TABLE 4

| | |
|---|---|
| 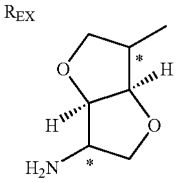 | Example 36a<br>14-O-{[(3S,3aS,6S,6aR)-6-Amino-hexahydro-furo[3,2-b]furan-3-ylsulfanyl]-acetyl}-mutilin in the form of a hydrochloride-<br>(DMSO-$d_6$): 8.3 (bs, 3H, $NH_3^+$), 6.15,5.05,5.02(3 x m,$H_{19}$,$H_{20}$,$H_{21}$), 5.55 (d,1H,8.2Hz,$H_{14}$), 4.65, 4.55(2 x m, $H_{11}$-OH, H-3a',H6a'), 3.6-4.1 (m, 5H, H-2',H-5',H-6'), 3.3-3.5 (m,4H,$H_{11}$,H-3',$H_{22}$), 1.35,1.05<br>(2 x s, $(CH_3)_{15}$,$(CH_3)_{18}$), 0.8,0.62 (2 x d,$(CH_3)_{16}$,$(CH_3)_{17}$,J=6.5Hz)<br>Example 36b<br>14-O-{[(3R,3aS,6S,6aR)-6-Amino-hexahydro-furo[3,2-b]furan-3-ylsulfanyl]-acetyl}-mutilin-hydrochloride<br>(DMSO-$d_6$): 8.3 (bs, 3H, $NH_3^+$), 6.15,5.07,5.03(3 x m,$H_{19}$,$H_{20}$,$H_{21}$), 5.55 (d, 1H,,$H_{14}$,J=8.2Hz), 4.60, 4.7(2 x m,H-3a',H6a'), 3.6-4.1 (m, 5H, H-2',H-5',H-6'), 3.3-3.5 (m,4H,$H_{11}$,H-3',$H_{22}$), 1.35,1.05,<br>(2 x s,$(CH_3)_{15}$, $(CH_3)_{18}$), 0.8,0.62 (2 x d,$(CH_3)_{16}$,$(CH_3)_{17}$,J=6.9Hz)<br>Example 36c<br>14-O-{[(3S,3aS,6R,6aR)-6-Amino-hexahydro-furo[3,2-b]furan-3-ylsulfanyl]-acetyl}-mutilin-hydrochloride |

TABLE 4-continued (DMSO-$d_6$): 8.25 (bs, 3H, $NH_3^+$), 6.15,5.06,5.03(3 × m,$H_{19}$,$H_{20}$,$H_{21}$), 5.55 (d,1H,$H_{14}$,J=8.4Hz), 4.60 (m,2H, H-3a',H6a'), 3.55-4.2 (m, 5H, H-2',H-5',H-6'), 3.35-3.5 (m,4H,$H_{11}$,H-3',$H_{22}$), 1.35,1.05 (2 × s,$(CH_3)_{15}$,$(CH_3)_{18}$), 0.8,0.62 (2 × d,$(CH_3)_{16}$,$(CH_3)_{17}$,J=6.9Hz)

$R_{EX}$

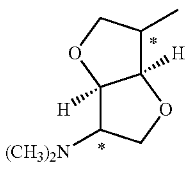

Example 37

14-O-{[(3S,3aS,6S,6aR)-6-Dimethylamino-hexahydro-furo[3,2-b]furan-3-ylsulfanyl]-acetyl}-mutilin in the form of a hydrochloride (DMSO-$d_6$): 11.25 (bs, 1H,$NH^+$), 6.15,5.06,5.03(3 × m,$H_{19}$,$H_{20}$,$H_{21}$), 5.55 (d,1H,,$H_{14}$,J=8.2Hz), 4.60 (m,1H, H3a'), 3.3-4.1 (m, H-2',H-5',H-6',H-6a',$H_{11}$,H-3',$H_{22}$), 2.8,2.7 (2 × d, 6H, $NH^+(CH_3)_2$,J=4.5Hz), 1.35,1.05 (2 × s,$(CH_3)_{15}$,$(CH_3)_{18}$), 0.8,0.62 (2 × d,$(CH_3)_{16}$,$(CH_3)_{17}$,J=6.9Hz)

$R_{EX}$

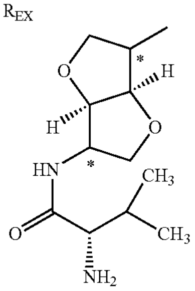

Example 38a

14-O-{[(3S,3aS,6S,6aR)-6-((R)-Amino-3-methyl-butyrylamino)-hexahydro-furo[3,2-b]furan-3-ylsulfanyl]-acetyl}-mutilin in the form of a hydrochloride (DMSO-$d_6$): 8.65 (d, 1H, NH,J=8.2Hz), 7.8 (bs, 3H, $NH_3^+$), 6.15,5.07,5.02(3 × m,$H_{19}$,$H_{20}$,$H_{21}$), 5.55 (d,1H,5,2Hz,$H_{14}$), 4.55, 4.45(2 × m, 3H, $H_{11}$-OH, H-3a',H6a'), 3.6-4.2 (m, 5H, H-2',H-5',H-6'), 3.4-3.5 (m, 4H,$H_{11}$,H-3',$H_{22}$), 1.35,1.05 (2 × s,$(CH_3)$15,$(CH_3)_{18}$), 0.88, 0.92 (2 × d, $(CH_3)_2$CH,J=6.8Hz), 0.8,0.62 (2 × d,$(CH_3)_{16}$,$(CH_3)_{17}$,J=6.8Hz)

Example 38b

14-O-{[(3R,3aS,6S,6aR)-6-((R)-Amino-3-methyl-butyrylamino)-hexahydro-furo[3,2-b]furan-3-ylsulfanyl]-acetyl)-mutilin in the form of a hydrochloride (DMSO-$d_6$): 8.8 (d, 1H, NH,J=7.1Hz), 8.15 (bs, 3H, $NH_3^+$), 6.15, 5.07,5.03 (3 × m,$H_{19}$,$H_{20}$,$H_{21}$), 5.55 (d,1H,7.9Hz,$H_{14}$), 4.6, 4.4 (2 × m, 2H,H-3a',H6a'), 3.6-4.2 (m, 5H, H-2',H-5',H-6'), 3.2-3.5 (m,4H,$H_{11}$,H-3',$H_{22}$), 1.35,1.05 (2 × s,$(CH_3)_{15}$,$(CH_3)_{18}$), 0.89, 0.91 (d, $(CH_3)_2$CH, J=6.8Hz), 0.8,0.62 (2 × d,$(CH_3)_{16}$,$(CH_3)_{17}$,J=6.8Hz)

Example 38c

14-O-{[(3S,3aS,6R,6aR)-6-((R)-Amino-3-methyl-butyrylamino)-hexahydro-furo[3,2-b]furan-3-ylsulfanyl]-acetyl}-mutilin in the form of a hydrochloride (DMSO-$d_6$): 8.4 (d, 1H, NH,J=7.8Hz), 8.1 (bs, 3H, $NH_3^+$), 6.15,5.06, 5.02 (3 × m,$H_{19}$,$H_{20}$,$H_{21}$), 5.55 (d,1H,8.2Hz,$H_{14}$), 4.6, 4.5 (2 × m, 2H,H-3',$H_{22}$), 1.35,1.05 (2 × s,$(CH_3)_{15}$,$(CH_3)_{18}$), 0.94, 0.90 (d, $(CH_3)_2$CH, J=6.8Hz), 0.8,0.62 (2 × d,$(CH_3)_{16}$,$(CH_3)_{17}$,J=6.8Hz)

$R_{EX}$

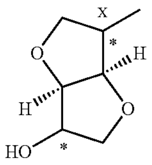

Example 39a

14-O-{[(3S,3aS,6R,6aR)-6-Hydroxy-hexahydro-furo[3,2-b]furan-3-ylsulfanyl]-acetyl}-mutilin (DMSO-$d_6$): 6.15,5.07,5.03(3 × m,$H_{19}$,$H_{20}$,$H_{21}$),5.55(d, 1H,$H_{14}$, J=8.3Hz), 4.85 (d,1H,6'-OH,J=6.4Hz), 4.5 (d,1H,11-OH,J=6.1Hz), 3.65-4.45 (m, H-3a',H-6a',H-2',H-5',H-6'), 3.3-3.45 (m,H-5',$H_{11}$,H-3',$H_{22}$), 1.35,1.05 (2 × s,$(CH_3)_{15}$,$(CH_3)_{18}$), 0.8,0.62 (2 × d,$(CH_3)_{16}$,$(CH_3)_{17}$,J=6.9Hz)

Example 39b

14-O-{[(3R,3aS,6R,6aR)-6-Hydroxy-hexahydro-furo[3,2-b]furan-3-ylsulfanyl]-acetyl}-mutilin (DMSO-$d_6$):6.15,5.06,5.03(3 × m,$H_{19}$,$H_{20}$,$H_{21}$),5.55(d,1H, $H_{14}$, J=8.3Hz), 4.8 (d,1H,6'-OH,J=5.7Hz), 4.5 (d,1H,11-OH,J=6.1Hz), 3.7-4.45 (m, H-3a',H-6a',H-2',H-5',H-6'), 3.2-3.5 (m,H-5',$H_{11}$,H-3',$H_{22}$), 1.35,1.05 (2 × s,$(CH_3)_{15}$,$(CH_3)_{18}$), 0.8,0.62,(2 × d,$(CH_3)_{16}$,$(CH_3)_{17}$,J=6.8Hz)

Example 39c

14-O-{[(3S,3aS,6S,6aR)-6-Hydroxy-hexahydro-furo[3,2-b]furan-3-ylsulfanyl]-acetyl}-mutilin (DMSO-$d_6$): 6.1,5.07,5.02(3 × m,$H_{19}$,$H_{20}$,$H_{21}$),5.55 (d, 1H,, $H_{14}$,J=8.3Hz), 5.2 (d,1H,6'-OH), 3.55-4.55 (m,11-OH,H-3a',H-6a',H-2',H-5',H-6'), 3.3-3.45 (m,$H_{11}$,H-3',$H_{22}$), 1.35,1.05 (2 × s,$(CH_3)_{15}$,$(CH_3)_{18}$), 0.8,0.62 (2 × d,$(CH_3)_{16}$,$(CH_3)_{17}$,J=6.8Hz)

In another aspect the present invention provides 14-O-(hydroxy- or oxo)-(heterocyclyl-sulfanylmethylcarbonyl)-pleuromutilins, wherein heterocyclyl is an aliphatic ring of 4 to 8 ring members, preferably 5 to 7, comprising one nitrogen as the heteroatom, e.g. a compound of formula

ID

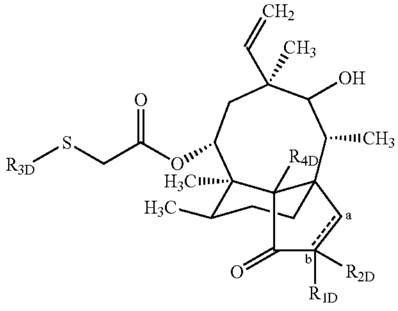

wherein $R_{1D}$ has the meaning of $R_{1A}$ as defined above, $R_{2D}$ has the meaning of $R_{2A}$ as defined above, $R_{4D}$ has the meaning of $R_{6A}$ as defined above, the dotted line has the meaning as defined above, and $R_{3D}$ is aliphatic heterocyclyl of 4 to 8 ring members, and comprising one nitrogen atom as the heteroatom, or $(C_{4-8})$ cycloalkyl, which heterocyclyl or cycloalkyl is substituted by hydroxy or oxo.

In a compound of formula $I_D$ preferably $R_{1D}$ is hydrogen or deuterium, $R_{2D}$ is hydrogen or deuterium, the dotted line is not present (single bond), $R_{3D}$ is as defined above, e.g. heterocyclyl has preferably 5 to 7 ring members, e.g. heterocyclyl is attached to the sulphur in a compound of formula ID via a carbon bond; such as hydroxypyrrolidino, hydroxypiperidino, oxo-perhydroazepinyl; and cycloalkyl is preferably $(C_{5-6})$cycloalkyl, e.g. cyclopentanonyl, $R_{4D}$ is hydrogen or deuterium, e.g. including 14-O-(hydroxy- or oxo-heterocyclyl-sulfanyl-methylcarbonyl)-pleuromutilins, wherein heterocyclyl is an aliphatic ring of 4 to 8 ring members, preferably 5 to 7, comprising one nitrogen as the heteroatom, which are selected from the group consisting of e.g. including pleuromutilins which are selected from the group consisting of compounds of formulae $I_{EX}$

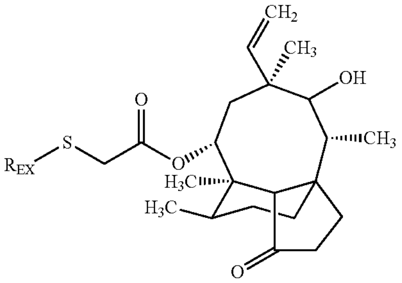

or $I''_{EX}$

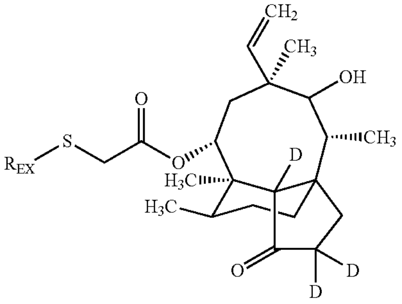

wherein $R_{EX}$ is as set out in TABLE 5. The compounds of TABLE 5 are compounds of formula $I_{EX}$, with the exception of the compound of Example 41 which is a compound of formula $I''_{EX}$. $^1$H-NMR-data of the compounds described and obtained according, e.g. analogously, to a process as described in the examples are also indicated in TABLE 5:

TABLE 5

| | |
|---|---|
| $R_{EX}$ 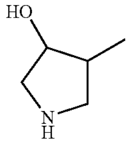 | Example 40<br>14-O-[(3-R*-Hydroxypyrrolidine-4-(R*)yl)-sulfanyl-acetyl]-mutilin and 14-O-[(3-S*-Hydroxypyrrolidine-4-(S*)yl)-sulfanyl-acetyl]-mutilin in the form of a hydrochloride (diastereoisomeric mixture)<br>(d-6-DMSO): 9.4,9.65 (2 x b,2H,$NH_2^+$), 3.6,3.2(2 x m ,4H,$CH_2NCH_2$), 4.45(m, 1H,CHO), 3.45-3.32(m,3H,$H_{11}H_{22}$), 3.95 (m, 1H,CHS), 1.18,1.45 (2 x s,$(CH3)_{15}$,$(CH3)_{18}$), 0.75,0.88 (2 x d,$(CH_3)_{16}$,$(CH_3)_{17}$,J=5.4Hz 0.98) |
| $R_{EX}$ 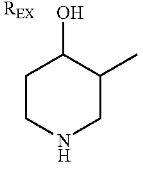 | Example 41<br>2,2,4-Trideutero-14-O-[((3-(S*)-hydroxy-piperidine-4-(S*)-yl) sulfanyl)-acetyl]mutilin in the form of a deuterochloride<br>(d-6-DMSO,350K): 8.05 (b,3H,$NH_3^+$), 4.25-4.1(m,3H,$CH_2N$, NHCHC═O), 3.75(m, 1H,CHO), 3.45-3.32(m,3H,$H_{11}H_{22}$), 2.89 (m,1H,CHS), 1.18,1.45(2 x s,$(CH_3)_{16}$,$(CH_3)_{17}$), 0.9 (m,6H,$CH(CH_3)_2$), 0.75,0.88 (2 x d,$(CH_3)_{16}$,$(CH_3)_{17}$,J=5.4Hz 0.98). The signals of the 2,2'- and 4-protons of the tricyclic moiety are missing in thast spectrum.<br>Mass Spectroscopy (MS): m/e: 496 |

TABLE 5-continued

| | |
|---|---|
| 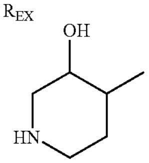 | Example 42<br>14-O-[(3R*-Hydroxypiperidin-4-(R*)yl)-sulfanyl-acetyl]mutilin in the form of a hydrochloride + 14-O-[(3S*-Hydroxypiperidin-4-(S*)yl)-sulfanyl-acetyl]mutilin in the form of a hydrochloride<br>(d-6-DMSO,350K): 8.05 (b,3H,$NH_3^+$), 4.25-4.1(m,3H,$CH_2N$, NHCHC═O), 3.75(m,1H, CHO), 3.45-3.32(m,3H,$H_{11}H_{22}$), 2.89 (m,1H,<br>CHS), 1.18,1.45(2 × s,$(CH_3)_{15}$,$(CH_3)_{18}$), 0.9 (m,6H,CH$(CH_3)_2$),<br>0.75,0.88(2 × d,$(CH_3)_{16}$, $(CH_3)_{17}$,J=5.4Hz 0.98) |
| 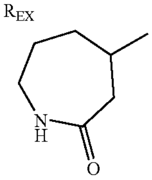 | Example 43<br>14-O-[((Azepan-2-one-4-(R/S)-yl)-sulfanyl acetyl)]-mutilin<br>($d_6$-DMSO): 6.15, 5.1 (2 × m,$H_{19}$,$H_{20}$,$H_{21}$), 5.52(d, 1H,J=5,2Hz,$H_{14}$),<br>3.4(m, 1H,$H_{11}$,), 3.3 (m,2H,$H_{22}$), 3.1 (m,2H,SCH,CHN),<br>1.18,1.45(2 × s,$(CH3)_{15}$,$(CH3)_{18}$), 0.75,0.88<br>(2 × d,$(CH_3)_{16}$,$(CH_3)_{17}$,J=5.4Hz) |
| 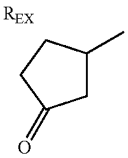 | Example 44<br>14-O-{[(3-Oxo-cyclopentan-(R/S)-yl)-sulfanyl]-acetyl}-mutilin<br>($CDCl_3$): 6.45,5.35,5.2(3 × m,$H_{19}$,$H_{20}$,$H_{21}$), 5.8 (d,1H, ,$H_{14}$,J=8.4Hz),<br>3.6<br>(m, 1H, SCH), 3.35 (m,1H,11-OH), AB-system($\nu_A$ = 3.25, $\nu_B$ = 3.17,<br>2H, $H_{22}$, J=14.8Hz), 2.65 (m,1/2H,H-2a'), 2.6 (m,1/2H,H-2a'),<br>1.45,1.18(2 × s,$(CH_3)_{15}$,$(CH_3)_{18}$), 0.9,0.75<br>(2 × d,$(CH_3)_{16}$,$(CH_3)_{17}$,J=6.8Hz) |

Novel compounds provided by the present invention, including compounds, the formulae of which are as set out in TABLE 1 to TABLE 5, and compounds of formulae $I_A$, $I_B$, $I_C$, $I_D$, $I_{EX}$, $I'_{EX}$ and $I''_{EX}$ are herein designated as "novel compound(s) of (according to) the present invention". "The residue of an amino acid", whenever defined in any one of the novel compounds of the present invention includes that part of an amino acid, e.g. including natural and synthetic amino acids, e.g. valine and other amino acids as defined herein, most preferably valine; which remains if the hydroxy group from the carboxylic acid group is split off, e.g. in case of valine [HO—CO—CH($NH_2$)—CH$(CH_3)_2$] the residue —CO—CH($NH_2$)—CH$(CH_3)_2$.

In a novel compound of the present invention each single defined substitutent may be a preferred substituent, e.g. independently of each other substitutent defined.

A novel compound of the present invention includes a compound in any form, e.g. in free form, in the form of a salt, in the form of a solvate and in the form of a salt and a solvate.

In another aspect the present invention provides a novel compound of the present invention in the form of a salt.

A salt of a novel compound of the present invention includes a pharmaceutically acceptable salt, e.g. including a metal salt or an acid addition salt. Metal salts include for example alkali or earth alkali salts; acid addition salts include salts of a compound of formula I with an acid, e.g. hydrogen fumaric acid, fumaric acid, naphthalin-1,5-sulphonic acid, phosphoric acid, tartaric acid, citric acid, hydrochloric acid, deuterochloric acid; preferably hydrochloric acid. A novel compound of the present invention in free form may be converted into a corresponding compound in the form of a salt; and vice versa. A novel compound of the present invention in free form or in the form of a salt and in the form of a solvate may be converted into a corresponding compound in free form or in the form of a salt in unsolvated form; and vice versa.

A novel compound of the present invention may exist in the form of isomers and mixtures thereof; e.g. optical isomers, diastereoisomers, cis-, trans-conformers. A compound of the present invention may e.g. contain asymmetric carbon atoms and may thus exist in the form of diastereoisomeres and mixtures thereof, e.g. racemates. For example a novel compound of the present invention may comprise the residue of an amino acid. In such amino acid residue the carbon atom to which the amino group is attached may be an asymmetric carbon atom and the amino group attached may thus be in the R- or S-configuration. A novel compound of the present invention may comprise a cycloalkyl, e.g. attached to the sulfanyl group, which cycloalkyl may be further substituted, and said substitutents may exist in the cis or in the trans conformation. E.g., the carbon atom of a cycloalkyl group to which the sulfanyl group is attached may be asymmetric, e.g. if said cycloalkyl is further substituted, and substitutents attached to said cycloalkyl group may be in the R- or in the S-configuration. E.g., a novel compound of the present invention also may comprise an oxime group. The hydrox group attached to the imino group may be in syn- or in anti-configuration.

Isomeric mixtures may be separated as appropriate, e.g. according, e.g. analogously, to a method as conventional, to obtain pure isomers. The present invention includes a novel compound of the present invention in any isomeric form and in any isomeric mixture.

The present invention also includes tautomers of a novel compound of the present invention where such tautomers can exist.

Any compound described herein, e.g. a novel compound of the present invention, may be prepared as appropriate, e.g. according to a method as conventional, e.g. analogously, e.g. or as specified herein.

In another aspect the present invention provides a process for the production of a compound of formula $I_P$

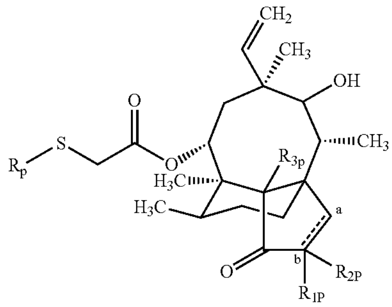

wherein $R_{1P}$ has the meaning of $R_{1A}$ as defined above, $R_{2P}$ has the meaning of $R_{2A}$ as defined above, $R_{3P}$ has the meaning of $R_{6A}$ as defined above, the dotted line has the meaning as defined above, and $R_P$ is aliphatic heterocyclyl of 4 to 8 ring members and comprising the one nitrogen atom as the heteroatom, or $(C_{4-8})$cycloalkyl, which heterocyclyl or cycloalkyl is substituted by hydroxy or oxo, comprising the steps a. reacting a compound of formula $II_P$

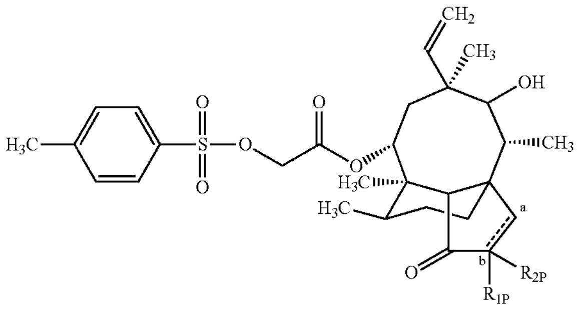

wherein $R_{1P}$ and $R_{2P}$ are as defined above, and the dotted line has the meaning as defined above, with thiourea and subsequent reduction to obtain a compound of formula $II_P$

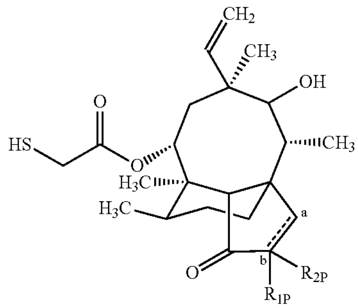

wherein $R_{1P}$ and $R_{2P}$ are as defined above, b. reacting a compound of formula $II_P$ obtained in step a, with a compound of formula $R_P$—H wherein $R_P$ is as defined above, in a reactive form, e.g. a mesylate or a tosylate, optionally in a protected form, to obtain a compound of formula $I_P$ (i.e. novel compound of the present invention), or to obtain a pre-form of a compound of formula $I_P$, c. optionally further reacting a pre-form obtained in step b. to obtain a compound of formula $I_P$, e.g. introducing deuterium to obtain a compound of formula $I_P$ wherein the substitutents are as defined above, and d. isolating a compound of formula $I_P$ obtained in step b. or in step c. from the reaction mixture.

$R_P$ is substituted $(C_{4-8})$cycloalkyl, substituted phenyl, substituted aliphatic heterocyclyl, having 4 to 8 ring members and comprising as a heteroatom 1 or 2 nitrogen atoms, alkyl, substituted by (substituted) amino, alkyl substituted by heterocyclyl, or substituted, bicyclic aliphatic heterocyclyl, comprising in each ring 5 ring members and one oxygen heteroatom, e.g. including the meanings of $R_P$ in the novel pleuromutilins of the present invention, $R_p$ is aliphatic heterocyclyl of 4 to 8 ring members and comprising one nitrogen atom as the heteroatom, or $(C_{4-8})$cycloalkyl, which heterocyclyl or cycloalkyl is substituted by hydroxy or oxo.

A process provided by the present invention may e.g. be carried out analogously to processes as set out in any of the patent references cited herein, e.g. analogously to a process for the production of compounds as described in patent literature cited herein, such as in WO0109095, WO0204414 and WO0222580, or as described herein.

All patent references cited herein are introduced by reference, especially with respect to the claim scopes and meanings of the substituents, e.g. including the preferred meanings of the substitutents, and with respect to production processes.

A pleuromutilin of the present invention includes the novel compounds of the present invention of formula $I_P$. A pleuromutilin of the present invention includes one or more, preferably one, pleuromutilins of the present invention, e.g. one pleuromutilin or a combination of different pleuromutilins of the present invention.

We have found that novel compounds of the present invention, including compounds of formula $I_P$, exhibit pharmacological activity similar to pleuromutilins in similar indications as described in WO0109095, WO0204414 and WO0222580, e.g. in test systems similar as described in WO0109095, WO0204414 and WO0222580, and additionally in test systems described herein. Compounds of formula $I_P$ are therefore useful as pharmaceuticals.

In another aspect the present invention provides a compound of formula $I_P$ for use as a pharmaceutical, preferably as an antimicrobial, such as an antibiotic, e.g. and as an anti-anaerobic, including the use as a pharmaceutical in the treatment of diseases mediated by *Mycobacterium*, such as *Mycobacterium tuberculosis*

In another aspect the present invention provides a compound of formula $I_P$ for use in the preparation of a medicament for the treatment of microbial diseases, for example of diseases mediated by bacteria, e.g. selected from Staphylococci, Streptococci, Enterococci, *Mycobacterium*, e.g. *Mycobacterium tuberculosis*; e.g. and of diseases mediated by Mycoplasms, *Chlamydia* and obligatory anaerobes.

In another aspect the present invention provides a method of treatment of microbial diseases, for example of diseases mediated by bacteria, e.g. selected from Staphylococci, Streptococci, Enterococci, *Mycobacterium*, e.g. *Mycobacte-*

*rium tuberculosis*; e.g. and of diseases mediated by Mycoplasms, *Chlamydia* and obligatory anaerobes, which method comprises administering to a subject in need of such treatment an effective amount of a novel compound of the present invention, e.g. including a compound of formula $I_P$; e.g. in the form of a pharmaceutical composition.

Treatment includes treatment and prophylaxis.

For such treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.05 g to about 5.0 g, of a novel compound of the present invention; conveniently administered, for example, in divided doses up to four times a day.

For treatment of diseases mediated by *Mycobacterium* with a pleuromutilin of the present invention similar considerations apply.

A novel compound of the present invention may be administered by any conventional route, for example enterally, e.g. including nasal, buccal, rectal, oral administration; parenterally, e.g. including intravenous, intramuscular, subcutaneous administration; or topically; e.g. including epicutaneous, intranasal, intratracheal administration; e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories.

For administration of a pleuromutilin of the present invention in diseases mediated by *Mycobacterium*, similar considerations apply, with the exception of topical administration.

The novel compounds of the present invention may be administered in the form of a pharmaceutically acceptable salt, e.g. an acid addition salt or metal salt; or in free form; optionally in the form of a solvate. The novel compounds of the present invention in the form of a salt exhibit the same order of activity as the novel compounds of the present invention in free form; optionally in the form of a solvate.

For administration of a pleuromutilin of the present invention in diseases mediated by *Mycobacterium* similar considerations apply.

A novel compound of the present invention may be used for pharmaceutical treatment according to the present invention alone, or in combination with one or more other pharmaceutically active agents. Such other pharmaceutically active agents e.g. include other antimicrobials, e.g. including antibiotics, e.g. cephalosporins, penicillins, erythromycins, tetracyclines.

Similar considerations apply for a pleuromutilin of to the present invention in diseases mediated by *Mycobacterium*, but appropriate other pharmaceutically active agents includes agents known to be active in the treatment of diseases mediated by *Mycobacterium*, such as Rifampicin (Rifampicin®), Streptomycin (Streptomycin®), Ethambutol (Ethambutol®), Pyrizinamid (Pyrizinamid®).

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a novel compound of the present invention, e.g. a compound of formula $I_P$, in association with at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers; e.g. further comprising another pharmaceutically active agent.

Pharmaceutical composition comprising pleuromutilins of the present invention for administration in diseases mediated by *Mycobacterium* may comprise similar excipient as described above.

In another aspect the present invention provides a pharmaceutical composition comprising a pleuromutilin of the present invention in association with at least one pharmaceutical excipient, and further comprising another pharmaceutically active agent useful in the treatment of *Mycobacterium*, e.g. *M. tuberculosis*, infections, such as Rifampicin (Rifampicin®), Streptomycin (Streptomycin®), Ethambutol (Ethambutol®), Pyrizinamid (Pyrizinamid®).

Such compositions may be manufactured according, e.g. analogously to a method as conventional, e.g. by mixing, granulating, coating, dissolving or lyophilizing processes. Unit dosage forms may contain, for example, from about 0.5 mg to about 1500 mg, such as 1 mg to about 500 mg.

Pleuromutilins of the present invention for administration in diseases mediated by *Mycobacterium tuberculosis* may be administered in a similar mode and in similar dosages as Rifampicin or Streptomycin.

A pleuromutilin of the present invention is preferably selected from the group consisting of a compound of formula I-U.S. Pat. No. 4,278,674, a compound of formula I-EP0153277, a compound of formula I-WO0109095, a compound of formula I-WO0204414, a compound of formula I-WO0222580, a compound of TABLE 1, a compound of formula $I_B$, or a of formula $I_D$; e.g. including a compound of formula I-Tiamulin, a compound of formula I-Valnemulin; e.g. in the form of a hydrochloride;

a compound of formula

I-PREF1

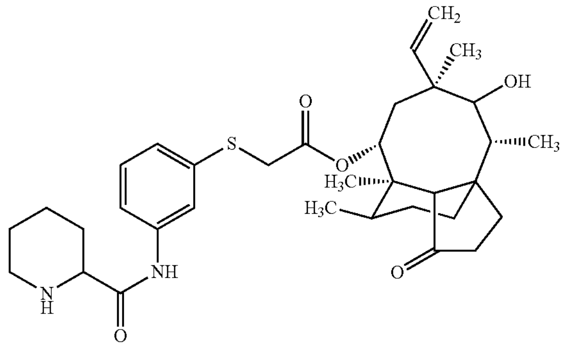

e.g. in the form of a hydrochloride;

a compound of formula

I-PREF2

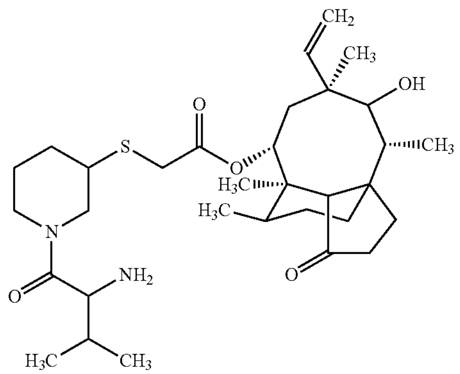

e.g. in the form of a hydrochloride, a compound of formula

I-PREF3

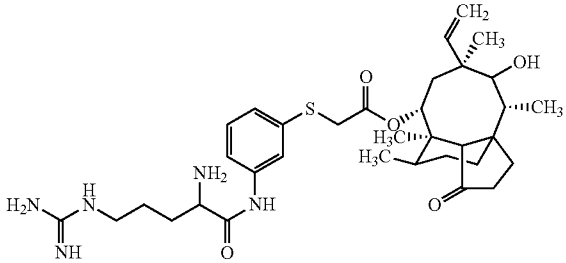

e.g. in the form of a hydrochloride, a compound of formula

I-PREF4

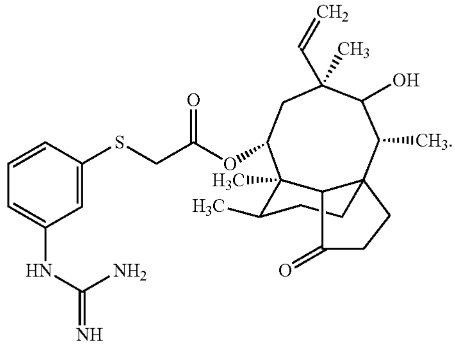

e.g. in the form of a hydrochloride, a compound of formula

I-PREF5

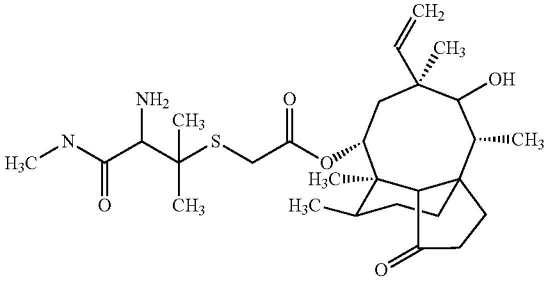

e.g. in the form of a hydrochloride, a compound of formula

I-PREF6

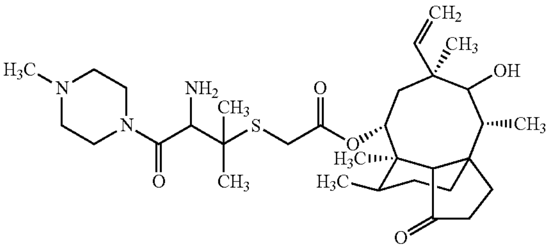

e.g. in the form of a hydrochloride, a compound of formula

I-PREF7

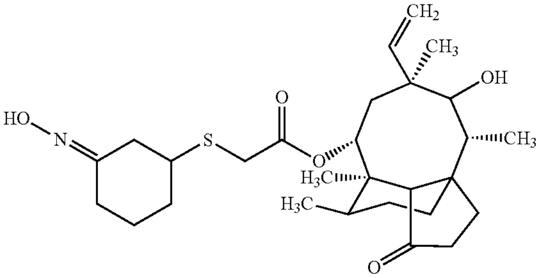

and a compound of

I-PREF8

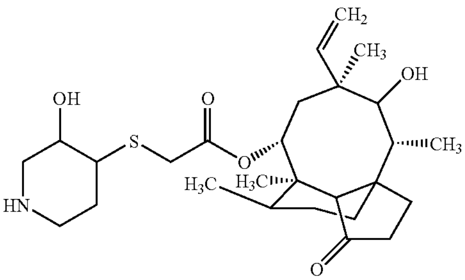

e.g. in the form of a hydrochloride.

Activity against strains of *Mycobacterium*, e.g. *M. tuberculosis* may be determined according to the following General Test Procedure:

General Test Procedure

Is carried out according to the known and appropriate Agar Dilution Test.

Agar is used as a substrate. Shortly before solidification of the Agar TEST COMPOUNDS in different concentrations are added and mixed into the still liquid agar mass (according to the Agar dilution test). Controls without TEST COMPOUNDS are also prepared for determination of strain growth ability. The thus prepared agars are inoculated after solidification with *Mycobacterium tuberculosis* strains. Incubation is carried out in normal incubators at 37° C. As a nutrition medium Middlebrook 7H10+OADC (Oleic, Albumin, Dextrose, Catalase) Enrichment (pH 6.71-6.73) is used.

The minimum inhibition concentration (MIC) which is the compound concentration in the agar which inhibits 99% of strain growth, is determined after 3 weeks, 4 weeks and 5 weeks after inoculation.

Pleuromutilins of the present invention show activity against strains of *Mycobacterium*, e.g. *M. tuberculosis* and are thus useful in the treatment of infections caused by *Mycobacterium*. Pleuromutilins of the present invention surprisingly are even active against resistant and multiresistant *M. tuberculosis* strains, e.g. strains which are resistant against treatment with known pharmaceuticals useful in the treatment of tuberculosis, e.g. Isoniacid, Rifampicin, Streptomycin.

In the following Examples all temperatures are in degree Centigrade and are uncorrected.

The following abbreviations are used:

| | |
|---|---|
| BOC: | tert.butoxyxcarbonyl |
| DMF: | N,N-dimethylformamide |
| EDC: | N-(3-dimethylaminopropyl)-N'-ethylcarbodiimide hydrochloride |
| EtAc: | ethyl acetate |
| HOBT: | 1-hydroxybenzotriazole |
| MS: | mass spectroscopy |
| TBAF: | tetra-n-butylammonium fluoride |
| THF: | tetrahydrofurane |
| DCC: | dicyclohexylcarbodiimide |
| DMSO: | dimethylsulfoxide |
| EtOH: | ethanol |
| MeOH: | methanol |
| RT: | room temperature |
| TFA: | trifluoroacetic acid |

Chromatography is carried out on silica gel.

PREPARATION EXAMPLES

Preparation of (Novel) Pleuromutilins of the Present Invention

Example I-A

14-O—[(N-(3-Methyl-2(R)-amino-butyryl)-piperidine-3-yl)-sulfanylacetyl]-mutilin in the form of a hydrochloride I-AA) 14-O—[(N—BOC-Piperidin-3(S)-yl)-sulfanylacetyl]-mutilin Method 1:

532 mg of 22-O-tosyl-pleuromutilin are added to a solution of 217 mg of N—BOC-piperidine-3(S)-thiol and 112 mg potassium tert. butylate in 10 ml of THF, the mixture obtained is stirred for 3 hours, the mixture obtained is distributed between EtAc and brine, the organic phase obtained is dried, solvent is evaporated and the evaporation residue obtained is subjected to chromatography. 14-O—[(N—BOC-Piperidin-3(S)-yl)-sulfanylacetyl]-mutilin is obtained.

Method 2:

A solution of 1.97 g of 22-mercapto-pleuromutilin, 1.39 g of N—BOC-3(R)-methylsulfonyloxy-piperidine and 0.12 g of sodium in 50 ml of EtOH is heated to 90° for 12 hours, from the mixture obtained solvent is evaporated and the evaporation residue is subjected to chromatography. 14-O—[(N—BOC-piperidin-3-yl)-sulfanylacetyl]-mutilin is obtained.

$^1$H-MR($CDCl_3$):6.45,5.35,5,2(3×m,$H_{19}$,$H_{20}$,$H_{21}$),5.74(d, 1H,5,2 Hz,$H_{14}$),3.35(d,1H,$H_{11}$,J=5.2 Hz), AB-system: 3.12, 3.18, J=14.7 Hz,$H_{22}$), 3.2,2.95,2.65,2.6(4×m,$CH_2NCH_2$), 2.85 (m,1H, SCH),1.18,1.45 (2×s,$(CH3)_{15}$,$(CH3)_{18}$), 0.75, 0.88(2×d,$(CH_3)_{16}$, $(CH_3)_{17}$,J=5.4 Hz)

I-AB) 14-O—[(N-(3-Methyl-2(R)-amino-butyryl)-piperidine-3-yl)-sulfanylacetyl]-mutilin in the form of a hydrochloride A solution of 280 mg of 14-O—[(N—BOC-piperidin-3-yl)-sulfanylacetyl]-mutilin in 20 ml of $CH_2Cl_2$ and 1 ml of TFA is stirred at RT for 30 minutes and from the mixture obtained solvent is evaporated. The evaporation residue obtained is treated with 40 ml of $CH_2Cl_2$, 55 mg of N-methyl-morpholine, 110 mg of N—BOC—(R)-valine and 105 mg of DCC are added and the mixture obtained is stirred for 3 hours. From the mixture obtained precipitated dicyclohexylurea is filtered off and the filtrate obtained is subjected to chromatography. Purified 14-O—[(N-(3-Methyl-2(R)-amino-butyryl)-piperidine-3-yl)-sulfanylacetyl]-mutilin obtained is treated with TFA in $CH_2Cl_2$, solvent is evaporated and the evaporation residue obtained is treated with etheric HCl. 14-O—[(N-(3-Methyl-2(R)-amino-butyryl)-piperidine-3-yl)-sulfanylacetyl]-mutilin in the form of a hydrochloride is obtained.

$^1$H-NMR(d-6-DMSO,330K): 6.45,5.35,5,2(3×m,$H_{19}$,$H_{20}$, $H_{21}$), 5.74 (d,1H,5,2 Hz,$H_{14}$), 5.45 (d,1H,NH,J=7.8 Hz), 4.1 (m,1H,NHCHCO), 3.35 (d,1H,$H_{11}$,J=5.2 Hz), AB-system: 3.12,3.18, J=14.7 Hz,$H_{22}$), 3.2, 2.95, 2.65 ,2.6 (4×m, $CH_2NCH_2$), 2.8 (m,1H,SCH), 1.18,1.45 (2×s,$(CH3)_{15}$, $(CH3)_{18}$), 0.75, 0.88 (2×d,$(CH_3)_{16}$,$(CH_3)_{17}$,J=5.4 Hz), 0.78.0.84 (2×d, $(CH_3)_2$CHJ=6.8 Hz)

Example I-B

14-O—[(N-(3-Methyl-2(R)-amino-butyryl)-piperidine-3(S)-yl)-sulfanylacetyl]-2(S)-fluoro-mutilin in the form of a hydrochloride IBA) 14-O-(Tosyloxyacetyl)-2(S)-fluoro-mutilin To a solution of 500 mg of 14-O-(hydroxyacetyl)-2(S)-fluoro-mutilin (see e.g. Vyplel H., et al *J Fluorine Chem;* 23, 482 (1983)), in 5 ml of $CH_2Cl_2$ 450 mg of toluene sulfonic acid anhydride and 0.21 ml of pyridine are added and the mixture obtained is stirred for 4 hours at RT. The mixture obtained is diluted with $CH_2Cl_2$ and extracted with 1N HCl, aqueous $NaHCO_3$ and $H_2O$. The organic phase obtained is dried, solvent is evaporated and the evaporation residue is subjected to chromatography. 14-O-[tosyloxyacetyl]-2(S)-fluoro-mutilin is obtained.

IBB) 14-O—[(N-(3-Methyl-2(R)-amino-butyryl)-piperidine-3(S)-yl)-sulfanylacetyl]-2(S)-fluoro-mutilin in the form of a hydrochloride is obtained starting from 14-O-[tosyloxyacetyl]-2(S)-fluoro-mutilin analogously to the method of Example IAB). Characterisation data see TABLE 1, Example 12.

Example I-C

14-O-[(3-Guanidino-phenylsulfanyl)-acetyl]mutilin in the form of a hydrochloride ICA) 14-O-[(3-Amino-phenylsulfanyl)-acetyl]-mutilin A solution of 0.92 g of sodium and 5 g of 3-amino-thiophenol in 100 ml of dry EtOH is added to a solution of 21.3 g of 22-O-tosyl-pleuromutilin (see e.g. H. Egger et al., J. Antibiotics 29, 923 (1976)) in 250 ml of ethylmethylketone at 25° under careful temperature control. The mixture obtained is kept for 15 hours at 25°, filtered and the filtrate obtained is concentrated under reduced pressure and subjected to chromatography. 14-O-[(3-Amino-phenylsulfanyl)-acetyl]-mutilin is obtained. $^1$H-NMR($CDCl_3$): 0.58(d, 3H, $H_{16}$, J=7.2 Hz), 0.81 (d, 3H, $H_{17}$, J=7.3 Hz),1.02 (s, 3H, $H_{18}$), 1.32 (s, 3H, $H_{15}$), ABX-system($\nu_A$=1.2, $\nu_B$=1.88, $H_{13a}$,$H_{13b}$, J=16.1 Hz, J=9.1 Hz), 2.08(d,1H, $H_4$, J=2.1 Hz), ABXY-system ($\nu_A$=2.23, $\nu_B$=2.19, $H_{2a}$,$H_{2b}$, J=16.2 Hz, J=9.1 Hz, J=1.8 Hz), 2.3(m,1H,$H_{10}$), 3.4 (d,1H,$H_{11}$, J=5.98 Hz), AB-system ($\nu_A$=3.81, $\nu_B$=3.89, 2H, $H_{22}$, J=14.1 Hz), 5.18(dd,1H, $H_{20a}$, J=17.5 Hz, J=1.6 Hz), 5.29(dd,1H,$H_{20b}$, J=11 Hz, J=1.6 Hz), 5.51 (d,1H, $H_{14}$, J=8.3 Hz), 6.05 (dd,1H,$H_{19}$, J=11 Hz, J=17.5 Hz), 7.0 (m,1H, arom.H), 7.18 (m2H, arom.H), 7.3t,1H, arom.$H_5$, J=8 Hz).

ICB) 14-O-[(3-Guanidino-phenylsulfanyl)-acetyl]mutilin in the form of a hydrochloride A solution of 2.4 g of 14-O-[(3-amino-phenylsulfanyl)-acetyl]mutilin, 1.5 g of cyanamide and 0.44 ml of HCl conc. in 20 ml of dioxane is stirred at room temperature for 28 hours.

14-O-[(3-Guanidino-phenylsulfanyl)-acetyl]mutilin in the form of a hydrochloride in crystalline form is obtained. Characterisation data see in TABLES above.

Example I-D

14-O-[(3R*-Hydroxypiperidin-4-(R*)yl)-sulfanyl-acetyl]mutilin and 14-O-[(3S*-Hydroxypiperidin-4-(S*)yl)-sulfanyl-acetyl]mutilin in the form of a hydrochloride (diastereoisomeric mixture)

1.06 g of pleuromutilin-22-O-tosylate dissolved in 1 ml of 2-butanone are slowly added to a solution of 466 mg of N—BOC-3-hydroxy-piperidin-4-thiol and 224 mg of potassium-tert. butylate in 20 ml of THF, the mixture obtained is stirred for 2 hours, the mixture obtained is distributed between brine and EtAc, extracted with 0.1N HCl, and the phases obtained are separated. The organic phase obtained is dried, and the evaporation residue obtained is subjected to chromatography. A mixture of 14-O-[(3R*-Hydroxypiperidin-4-(R*)yl)-sulfanyl-acetyl]mutilin and 14-O-[(3S*-Hydroxypiperidin-4-(S*)yl)-sulfanyl-acetyl]mutilin is obtained which is treated with etheric HCl to obtain the corresponding hydrochloride. Characterisation data see in TABLE 5, Example 42.

Example I-E 2,2,4-Trideutero-14-O-[((3-(S*)-hydroxy-piperidine-4-(S*)-yl)sulfanyl)-acetyl]mutilin in the form of a deuterochloride A solution of 300 mg of the compound obtained in Example ID in 30 ml dioxane with 5 ml of DCl (20% in $D_2O$) is kept for 6 days at 25°. From the mixture obtained solvent is evaporated and the concentration residue is subjected to lyophilization. 2,2,4-Trideutero-14-O-[((3-(S*)-hydroxy-piperidine-4-(S*)-yl)sulfanyl)-acetyl]mutilin in the form of a deuterochloride is obtained. Characterisation data see TABLE 5, Example 41.

Example I-F

14-O-[3-(R*)-((N—BOC—(R)-Valyl-amino-cyclohexan-1-(R*)-yl)sulfanyl)-acetyl]mutilin (a)

14-O-[3-(S*)-((N—BOC—(R)-Valyl-amino-cyclohexan-1-(S*)-yl)sulfanyl)-acetyl]mutilin (b)

14-O-[3-(S*)-((N—BOC—(R)-Valyl-amino-cyclohexan-1-(R*)-yl)sulfanyl)-acetyl]mutilin (c)

14-O-[3-(R*)-((N—BOC—(R)-Valyl-amino-cyclohexan-1-(S*)-yl)sulfanyl)-acetyl]mutilin (d)

2.66 g of pleuromutilin-22-O-tosylate dissolved in 10 ml THF are slowly added to a solution of 1.65 g of 3-(N—BOC—(R)-valyl-amino)-cyclohexane-(R/S)-thiol and 560 mg of potassium-tert. butylate in 25 ml of THF, the mixture obtained is stirred for 2 hours and distributed between brine and EtAc. The mixture obtained is extracted with 0.1N HCl, the organic phase obtained is dried, solvent is evaporated and the evaporation residue obtained is subjected to chromatography. Pure (a) 14-O-[3-(R*)-((N—BOC—(R)-Valyl-amino-cyclohexan-1-(R*)-yl)sulfanyl)-acetyl]mutilin (b) 14-O-[3-(S*)-((N—BOC—(R)-Valyl-amino-cyclohexan-1-(S*)-yl)sulfanyl)-acetyl]mutilin (c) 14-O-[3-(S*)-((N—BOC—(R)-Valyl-amino-cyclohexan-1-(R*)-yl)sulfanyl)-acetyl]mutilin, and (d) 14-O-[3-(R*)-((N—BOC—(R)-Valyl-amino-cyclohexan-1-(S*)-yl)sulfanyl)-acetyl]mutilin is obtained.

$^1$H-NMR ($d_6$-DMSO):

(a): 6.5(d,1H,NH,J=8.1 Hz), 6.15, 5.1 (2×m,$H_{19}$,$H_{20}$,$H_{21}$), 5.52(d,1H,J=5,2 Hz,$H_{14}$), 3.4(m,1H, $H_{11}$), 3.55 (m,1H, CHN), 3.7 (m,α-valyl), 3.2 (m,2H,$H_{22}$), 2.7 (m,1H,SCH), 1.4 (s,9H, tert.butyl), 1.18,1.45(2×s,$(CH3)_{15}$,$(CH3)_{18}$), 0.75,0.88 (2×d,$(CH_3)_{16}$,$(CH_3)_{17}$,J=5.4 Hz).

(b): 6.15, 5.1 (2×m,$H_{19}$,$H_{20}$,$H_{21}$), 5.52(d,1H,J=5,2 Hz,$H_{14}$), 3.4(m,1H,$H_{11}$), 3.55 (m,1H,CHN), 3.70 (m,α-valyl), 3.2 (m,2H,$H_{22}$), 2.7 (m,1H,SCH), 1.4 (s,9H,tert.butyl), 1.18, 1.45(2×s, $(CH3)_{15}$,$(CH3)_{18}$), 0.75,0.88 (2×d,$(CH_3)_{16}$, $(CH_3)_{17}$,J=5.4 Hz).

(c): 6.15, 5.1 (2×m,$H_{19}$,$H_{20}$,$H_{21}$), 5.52(d,1H,J=5,2 Hz,$H_{14}$), 3.4(m, 1H,$H_{11}$), 3.9 (m,1H,CHN), 3.75 (m,α-valyl), 3.2 (m,2H,$H_{22}$), 3.15 (m,1H,SCH), 1.4 (s,9H,tert.butyl), 1.18, 1.45(2×s, $(CH3)_{15}$, $(CH3)_{18}$), 0.75,0.88 (2×d,$(CH_3)_{16}$, $(CH_3)_{17}$,J=5.4 Hz).

(d): 6.15, 5.1 (2×m,$H_{19}$,$H_{20}$,$H_{21}$), 5.52(d,1H,J=5,2 Hz,$H_{14}$), 3.4(m,1H,$H_{11}$),3.9 (m,1H,CHN), 3.70 (m,α-valyl), 3.2 (m,2H,$H_{22}$), 3.15 (m,1H,SCH), 1.4 (s,9H,tert.butyl), 1.18, 1.45(2×s, $(CH3)_{15}$,$(CH3)_{18}$), 0.75,0.88 (2×d,$(CH_3)_{16}$, $(CH_3)_{17}$, J=5.4 Hz).

Example I-G

14-O-[3-(R*)-((R)-Valyl-amino-cyclohexan-1-(R*)-yl)-sulfanyl)-acetyl]-mutilin and 14-O-[3-(S*)-((R)-Valyl-amino-cyclohexan-1-(S*)-yl)-sulfanyl)-acetyl]-mutilin in the form of a hydrochloride (mixture of trans-diastereoisomers)

620 mg of a 1:1 mixture of 14-O-[3-(R*)-((N—BOC—(R)-valyl-amino-cyclohexan-1-(R*)-yl)sulfanyl)-acetyl]

mutilin and 14-O-[3-(S*)-((N—BOC—(R)-valyl-amino-cyclohexan-1-(S*)-yl sulfanyl)-acetyl]mutilin are dissolved in a mixture of 10 ml of dry etheric HCl and 10 ml of $CH_2Cl_2$. The mixture is stirred for 5 hours and a mixture of trans-diastereoisomers of 14-O-[3-(R*)-((R)-valyl-amino-cyclohexan-1-(R*)-yl)-sulfanyl)-acetyl]-mutilin of 14-O-[3-(S*)-((R)-valyl-amino-cyclohexan-1-(S*)-yl)-sulfanyl)-acetyl]-mutilin in the form of a hydrochloride is obtained and isolated. $^1$H-NMR($d_6$-DMSO): Rotamer. 8.4 (m,1H, C═ONH), 8.15 (b,3H,$NH_3^+$), 6.15, 5.1 (2×m,$H_{19}$,$H_{20}$,$H_{21}$), 5.52(d,1H,J=5,2 Hz,$H_{14}$), 3.95 (m1H, $CHNH_3^+$, 3.4(m,1H, $H_{11}$), 3.55 (m,α-valyl), 3.2-3.3 (m,2H,$H_{22}$), 3.18 (m,1H, SCH), 1.18,1.45(2×s,$(CH3)_{15}$,$(CH3)_{18}$), 0.9 (m,6H,CH$(CH_3)_2$), 0.75,0.88 (2×d,$(CH_3)_{16}$,$(CH_3)_{17}$,J=5.4 Hz)

Example I-H

14-O-[3-(R*)-((R)-Valyl-amino-cyclohexan-1-(S*)-yl)-sulfanyl)-acetyl]-mutilin and 14-O-[3-(S*)-((R)-Valyl-amino-cyclohexan-1-(R*)-yl)-sulfanyl)-acetyl]-mutilin in the form of a hydrochloride (mixture of cis-diastereoisomers)

is obtained analogously to the method of Example I-G, but using a 1:1 mixture of 14-O-[3-(R*)((N—BOC—(R)-valyl-amino-cyclohexan-1-(S*)-yl)sulfanyl)-acetyl]mutilin and 14-O-[3-(S*)-((N—BOC—(R)-valyl-amino-cyclohexan-1-(R*)-yl sulfanyl)-acetyl]mutilin as a starting material. $^1$H-NMR($d_6$-DMSO): Rotamers. 8.52 (m,1H,C═ONH), 8.2 (b,3H,$NH_3^+$), 6.15, 5.1 (2×m,$H_{19}$, $H_{20}$,$H_{21}$), 5.52(d,1H,J=5,2 Hz,$H_{14}$), 3.58 (m1H, $CHNH_3^+$, 3.4 (m,1H,$H_{11}$), 3.48 (m,α-valyl), 3.2-3.3 (m,2H,$H_{22}$), 2.75 (m,1H,SCH), 1.18,1.45(2× s,$(CH3)_{15}$,$(CH3)_{18}$), 0.9 (m,6H,CH$(CH_3)_2$), 0.75,0.88 (2×d, $(CH_3)_{16}$,$(CH_3)_{17}$,J=5.4 Hz)

Example I-I

14-O—[((N—(R)-Valyl-azepan-4-(R/S)-yl)-sulfanyl acetyl)]-mutilin in the form of a hydrochloride I-IA) 4-(R/S)-(2,4,6-Trimethyl-benzyl-sulfanyl)-azepan-2-one A solution of 828 mg of 3-(R/S)-(2,4,6-trimethyl-benzyl-sulfanyl)-cyclohexanone-oxime and 570 mg of toluenesulfonylchloride in 5 ml of pyridine is stirred at RT for 4 hours and additional 2 hours at 60°. The mixture obtained is distributed between diluted sulfuric acid (2 ml $H_2SO_4$ conc. in 15 ml $H_2O$) and $CH_2Cl_2$, the organic phase obtained is dried, solvent is evaporated and the evaporation residue is subjected to chromatography. 4-(R/S)-(2,4,6-Trimethyl-benzyl-sulfanyl)-azepan-2-one is obtained. $^1$H-NMR(d-6-DMSO): 7.5 (m,1H,NHCO), 6.8 (s,2H,arom.H), 3.75 (s,2H, $C_6H_5CH_2S$—),3.2 (m, 1H,CHN), 3.1(m,3H, $CH_2$NH,CHS) AB-system: $\nu_A$=2.72,$\nu_B$=2.65( 2H,CH2C═O, J=13.4 Hz, J=4.5 Hz) 2.13 2.15,2.3(9H, 3×$CH_3$)

I-IB) 4-(R/S)-(2,4,6-Trimethyl-benzyl-sulfanyl)-azepane 3.3 g of 4-(R/S)-(2,4,6-trimethyl-benzyl-sulfanyl)-azepan-2-one are added to a mixture of 15 ml of a 1M-solution of $LiAlH_3$ and 50 ml THF are added. The mixture obtained is heated for 1 hour at 80°, poured into 200 ml of a 20% aqueous $NH_4$Cl-solution and the mixture obtained is extracted with EtAc. The organic phase obtained is dried and solvent is evaporated. 4-(R/S)-(2,4,6-Trimethyl-benzyl-sulfanyl)-azepane is obtained.

I-IC) N—BOC-(4-(R/S)-(2,4,6-Trimethyl-benzyl-sulfanyl))-azepane

A solution of 2.63 g of 4-(R/S)-(2,4,6-trimethyl-benzyl-sulfanyl)-azepane, 2.18 g of BOC-anhydride and 1 g of triethylamine in 100 ml of THF is stirred at 25° for 12 hours and from the mixture obtained solvent is evaporated. The evaporation residue obtained is distributed between $CH_2Cl_2$ and 1M HCl. Solvent from the organic phase obtained is evaporated and the evaporation residue is subjected to chromatography. N—BOC-(4-(R/S)-(2,4,6-trimethyl-benzyl-sulfanyl))-azepane is obtained. $^1$H-NMR ($d_6$-DMSO): 6.8 (s,2H, arom.H), 3.75 (s,2H,$C_6H_5CH_2S$—),3.2-3.5(m,4H, $CH_2NHCH_2$), 2.9(m,1H,CHS), 2.13 2.15,2.3(9H, 3×$CH_3$)

I-IC) N—BOC-4-(R/S)-Azepan-thiol is obtained analogously to the method of Example II-D, but using appropriate starting materials.

I-ID) 14-O—[((N—BOC-Azepan-4-(R/S)-yl)-sulfanyl acetyl)]-mutilin

A solution of 1.06 g of pleuromutilin-22-O-tosylate dissolved in 10 ml THF is slowly added to a solution of 420 mg of N—BOC-(4-(R/S)-azepane-thiol and 220 mg of potassium-tert.butylate in 25 ml of THF and the mixture obtained is stirred for 2 hours. The mixture obtained is distributed between brine and EtAc, the mixture obtained is extracted with 0.1N HCl, the organic phase obtained is dried, solvent is evaporated and the evaporation residue obtained is subjected to chromatography. 14-O—[((N—BOC-azepan-4-(R/S)-yl)-sulfanyl acetyl)-mutilin is obtained. $^1$H-NMR ($d_6$-DMSO): 6.15, 5.1 (2×m,$H_{19}$,$H_{20}$,$H_{21}$), 5.52 (d,1H,J=5,2 Hz,$H_{14}$), 4.52 (d,1H,OH,J=6.2 Hz)3.4(t,1H,$H_{11}$,J=6.2 Hz), 3.1-3.4 (m,6H, $H_{22}$,$CH_2NCH_2$), 2.9 (m,1H,SCH), 1.4 (s,9H,tert.butyl),1.18, 1.45(2×s,$(CH3)_{15}$, $(CH3)_{18}$), 0.75,0.88 (2×d,$(CH_3)_{16}$, $(CH_3)_{17}$,J=5.4 Hz)

I-IE) 14-O—[((Azepan-4-(R/S)-yl)-sulfanyl acetyl)]-mutilin in the form of a hydrochloride 400 mg of 14-O—[((N—BOC-azepan-4-(R/S)-yl)-sulfanyl-acetyl)-mutilin are dissolved in a mixture of 10 ml of dry etheric HCl and 10 ml of $CH_2Cl_2$. The mixture obtained is stirred for 5 hours and 14-O-[((azepan-4-(R/S)-yl)-sulfanyl acetyl)]-mutilin in the form of a hydrochloride is isolated. Characterisation data see TABLE 1, Example 14.

I-IF) 14-O—[((N—(R)-Valyl-azepan-4-(R/S)-yl)-sulfanyl acetyl)]-mutilin in the form of a hydrochloride A mixture of 245 mg 14-O-[((azepan-4-(R/S)-yl)-sulfanyl acetyl)]-mutilin in the form of a hydrochloride, 110 mg of BOC—R-valin, 95 mg of EDC and 100 mg of triethylamine in 10 ml THF is stirred at RT for 2 hours. The mixture obtained is distributed between brine and EtAc, the organic phase obtained is dried, solvent is evaporated and the evaporation residue obtained is subjected to chromatography. 14-O—[((N—BOC—(R)-Valyl-azepan-4-(R/S)-yl)-sulfanyl acetyl)]-mutilin-hydrochloride is obtained. The BOC-protecting group is cleaved by treatment with 5 ml of etheric HCl and 14-O—[((N—(R)-Valyl-azepan-4-(R/S)-yl)-sulfanyl acetyl)]-mutilin in the form of a hydrochloride is obtained. Characterisation data see TABLE 1, Example 15.

Example I-J

14-O—[((Azepan-2-one-4-(R/S)-yl)-sulfanyl acetyl)]-mutilin is obtained analogously to the method of Example IAB), starting from 4-(R/S)-mercapto-azepan-2-one. Characterisation data see TABLE 5, Example 43.

Example I-K

14-O-{[(3-Oxo-cyclopentan-(R/S)-yl)-sulfanyl]-acetyl}-mutilin

A solution of 3.95 g of 14-mercapto-acetyl-mutilin in 5 ml of pyridine is treated with 0.81 g of cyclopent-2-enone and a catalytical amount of triethylamine. The mixture obtained is stirred for 3 hours at room temperature, diluted with EtAc and extracted with 1N HCl and $H_2O$. The organic phase obtained is dried, solvent is evaporated and the evaporation residue obtained is subjected to chromatography. 14-O-{[(3-oxo-cyclopentan-(R/S)-yl)-sulfanyl]-acetyl}-mutilin is obtained. Characterisation data see in TABLE 5, Example 44.

Example I-L

14-O-{[(3-Hydroxyimino-cyclopentan-(R/S)-yl)-sulfanyl]-acetyl}-mutilin (syn and anti forms)

3.88 g of 14-O-{[(3-oxo-cyclopentan-(R/S)-yl)-sulfanyl]-acetyl}-mutilin are stirred overnight with 566 mg of hydroxylamine hydrochloride and 1.13 ml of triethylamine in 40 ml of DMF. From the mixture obtained solvent is distilled off, the distillation residue obtained is taken up in EtAc and the mixture obtained is extracted with 0.1N HCl and brine. The organic phase obtained is dried and solvent is evaporated. A mixture of 14-O-{[(3-hydroxyimino-cyclo-pentan-(R/S)-yl)-sulfanyl]-acetyl}-mutilin in the syn*- and in the anti*-form is obtained which mixture is either separated by chromatography to obtain the pure syn- and the pure anti-forms, or is used in the form of the mixture obtained in further reaction steps. Characterisation data see TABLE 3, Example 24.

Example I-M

14-O-{[(3-(2-Diethylamino-ethoxyimino)-cyclopentan-(R/S)-yl)-sulfanyl]-acetyl}-mutilin in the form of a hydrochloride 200 mg of 14-O-{[(3-hydroxyimino-cyclopentan-(R/S)-yl)-sulfanyl]-acetyl}-mutilin and 70 mg of diethylaminoethylchloride hydrochloride are stirred in 5 ml of $CH_2Cl_2$, 90 mg of potassium tert butoxide are added and stirring is continued for 2 days at RT. From the mixture obtained solvent is evaporated, the evaporation residue is subjected to chromatography, the relevant chromatographic fractions obtained are distributed between $Et_2O$ and 0.1N HCl and the aqueous layer is lyophilized. 14-O-{[(3-(2-diethylamino-ethoxyimino)-cyclopent-(R/S)-yl)-sulfanyl]-acetyl}-mutilin hydrochloride (syn/anti mixture) is obtained. Characterisation data see TABLE 3, Example 26.

Example I-N

14-O-[(2-(R*)-((R)-Valyl)-amino-cyclohexan-1-(R*)-yl)-sulfanyl acetyl)]-mutilin-hydrochloride I-NA) 14-O-[((2-(R*)-Aminocyclohexan-1-(R*)-yl)-sulfanyl acetyl)]-mutilin 1.06 g of pleuromutilin-22-O-tosylate dissolved in 5 ml of THF are slowly added to a solution of 334 mg of 2-(R*)-aminocyclohexan-(R*)-thiol in the form of a hydrochloride (see e.g. G. Kavadias and R. Droghini, Can. J. Chem. 1978, 56, 2743) and 92 mg sodium in 50 ml of EtOH, the mixture obtained is stirred for 2 hours, distributed between brine and EtAc, extracted with 0.1N HCl and dried. From the mixture obtained solvent is evaporated and the evaporation residue is subjected to chromatography. 14-O-[((2-(R*)-aminocyclohexan-1-(R*)-yl)-sulfanyl acetyl)]-mutilin is obtained. $^1$H-NMR($d_6$-DMSO): 6.15, 5.1 (2×m,$H_{19}$,$H_{20}$,$H_{21}$), 5.52(d, 1H,J=5,2 Hz,$H_{14}$), 2.45(m,1H,CHNH), 3.21 (s,2H,$H_{22}$), 3.4 (d,1H, $H_{11}$,J=5 Hz), 2.55(m,1H,CHS), 1.18,1.45 (2×s, $(CH3)_{15}$,$(CH3)_{18}$), 0.9 (m,6H,$CH(CH_3)_2$), 0.75,0.88 (2×d, $(CH_3)_{16}$,$(CH_3)_{17}$,J=5.4 Hz).

I-NB) 14-O-[(2-(R*)-((R)-Valyl)-amino-cyclohexan-1-(R*)-yl)-sulfanyl acetyl)]-mutilin in the form of a hydrochloride A mixture of 245 mg of 14-O-[((2-(R*)-aminocyclohexan-1-(R*)-yl)-sulfanyl acetyl)]-mutilin, 110 mg of BOC—(R)-valin, 95 mg of EDC and 68 mg of HOBT in 10 ml of THF is stirred at RT for 2 hours. The mixture obtained is distributed between brine and EtAc, the organic phase obtained is dried, solvent is evaporated and the evaporation residue is subjected to chromatography. 14-O-[((2-(R*)—(N—BOC—(R)-Valyl)-amino-cyclohexan-1-(R*)-yl)-sulfanyl acetyl)]-mutilin is obtained. The BOC-protecting group is cleaved by treatment with 5 ml of etheric HCl and 14-O-[(2-(R*)-((R)-valyl)-amino-cyclohexan-1-(R*)-yl)-sulfanyl acetyl)]-mutilin in the form of a hydrochloride is obtained. $^1$H-NMR($d_6$-DMSO): Diastereoisomers):8.45(m, 1H, NHC═O),8.1(b, 3H,$NH_3^+$), 6.15, 5.1 (2×m,$H_{19}$,$H_{20}$,$H_{21}$), 5.52(d,1H,J=5,2 Hz,$H_{14}$), 3.55 (m,1H, a-H-valyl),3.60(m,1H,CHNH), 3.26-3.35 (m, 2H,$H_{22}$),3.4(m,1H, $H_{11}$), 4.5 (d,1H,OH, J=6.2 Hz), 2.6,2.75(2×m,1H,CHS), 1.25 (b,3H,$CH_3$CS), 1.18,1.45(2×s, $(CH3)_{15}$,$(CH3)_{18}$), 0.9 (m,6H,$CH(CH_3)_2$), 0.75,0.88 (2×d, $(CH_3)_{16}$,$(CH_3)_{17}$, J=5.4 Hz)

Example I-O

14-O-{([(3S,3aS,6S,6aR)-6-Amino-hexahydro-furo[3,2-b]furan-3-ylsulfanyl]-acetyl}-mutilin hydrochloride I-OA) Toluene-4-sulfonic acid (3R,3aS,6R,6aR)-6-hydroxy-hexahydro-furo[3,2-b]furan-3-yl ester A solution of 5 g of (3R,3aS,6R,6aR)-hexahydro-furo[3,2-b]furan-3,6-diol in 50 ml of pyridine is stirred for 16 h with 7.8 g of toluenesulfonylchloride. From the mixture obtained solvent is distilled off and the distillation residue obtained is dissolved in EtAc and extracted with 1N HCl, saturated aqueous $NaHCO_3$-solution and $H_2O$. The organic layer obtained is dried, solvent is evaporated and the evaporation residue is subjected to chromatography. Toluene-4-sulfonic acid (3R,3aS,6R,6aR)-6-hydroxy-hexahydro-furo[3,2-b]furan-3-yl ester is obtained.

$^1$H-NMR(DMSO-$d_6$): 7.8 (d,2H,Ar—H,J=8.6 Hz),7.5 (d,2H,Ar—H,J=8.6 Hz), 4.8-4.9 (m,2H,H-3, 6-OH), 4.4 (dd, 1H,H-3a,J=4.7 and 5.0 Hz), 4.2 (dd,1H,H-6a, J=4.7 and 4.8 Hz), 3.9-4.0 (m,1H,H-6), 3.7-3.8 (m,2H,H-2 and H-5), 3.6 (d,1H,H-2,J=9.3 and 7.1 Hz), 3.2-3.4 (m,1H,H-5), 2.4 (s, 3H, Ar—$CH_3$).

I-OB) (3R,3aR,6S,6aR)-6-Azido-hexahydro-furo[3,2-b]furan-3-ol

A solution of 2.5 g of toluene-4-sulfonic acid (3R,3aS,6R,6aR)-6-hydroxy-hexahydro-furo[3,2-b]furan-3-yl ester in 30 ml of DMF is heated with 0.8 g of sodium azide under reflux for 2 hours, solvent is distilled off and the distillation residue obtained is dissolved in EtAc and extracted with $H_2O$. The organic phase obtained is dried and solvent is evaporated. (3R,3aR,6S,6aR)-6-azido-hexahydro-furo[3,2-b]furan-3-ol is obtained.

I-OC) {(3S,3aR,6R,6aR)-6-Hydroxy-hexahydro-furo[3,2-b]furan-3-yl}-carbamic acid tert-butyl ester To a solution of 1.5 g of (3R,3aR,6S,6aR)-6-azido-hexahydro-furo[3,2-b]furan-3-ol in 25 ml of dioxane 75 mg of palladium on charcoal (10%) are added and the mixture obtained is subjected to hydrogenation. The mixture obtained is filtered and stirred overnight with 3.2 ml of ethyldiisopropylamine and 4.1 g of $(BOC)_2O$. From the mixture obtained solvent is evaporated. The evaporation residue obtained is dissolved in EtAc and extracted with saturated aqueous sodium $NaHCO_3$-solution, 1N HCl and brine. The organic phase obtained is dried, solvent is evaporated and the evaporation residue obtained is subjected to chromatography. {(3S,3aR,6R,6aR)-6-hydroxy-hexahydro-furo[3,2-b]furan-3-yl}-carbamic acid tert-butyl ester is obtained.

$^1$H-NMR(DMSO-$d_6$): 7.1 (bs,1H,NH), 4.8 (d,1H,6-OH, J=10 Hz), 4.3 (dd,1H,H-6a,J=4.6 and 4.3 Hz), 4.27 (d,1H,H-3a,J=4.3 Hz), 4.0-4.1 (m,1H,H-6), 3.2-3.85 (m,5H,2×H-2, H-3, 2×H-5), 1.4 (s,9H,tert.butyl).

I-OD) Toluene-4-sulfonic acid (3R,3aS,6S,6aR)-6-tert-butoxycarbonylamino-hexahydro-furo[3,2-b]furan-3-yl ester A solution of 700 mg of {(3S,3aR,6R,6aR)-6-hydroxy-hexahydro-furo[3,2-b]furan-3-yl}-carbamic acid tert-butyl ester in 10 ml of pyridine is stirred for 16 hours with 785 mg of toluolsulfonylchloride, solvent is distilled off and the distillation residue is dissolved in EtAc and extracted with 1N HCl, saturated aqueous $NaHCO_3$-solution and $H_2O$. The organic layer obtained is dried and solvent is evaporated. Toluene-4-sulfonic acid (3R,3aS,6S,6aR)-6-tert-butoxycarbonylamino-hexahydro-furo[3,2-b]furan-3-yl ester is obtained.

I-OE) 14-O-{[(3S,3aS,6S,6aR)-6-tert-Butoxycarbonylamino-hexahydro-furo[3,2-b]furan-3-ylsulfanyl]-acetyl}-mutilin 267 mg of potassium tert.butoxide are added to a solution of 950 mg of toluene-4-sulfonic acid (3R,3aS,6S,6aR)-6-tert-butoxycarbonylamino-hexahydro-furo[3,2-b]furan-3-yl ester and 1032 mg of 14-mercapto-acetyl-mutilin in 20 ml of DMSO. The mixture obtained is stirred at 70° for 1 hour and distributed between EtAc and brine. The organic phase obtained is washed with $H_2O$, dried and solvent is evaporated. The evaporation residue obtained is subjected to chromatography. 14-O-{[(3S,3aS,6S,6aR)-6-tert-butoxycarbonylamino-hexahydro-furo[3,2-b]furan-3-ylsulfanyl]-acetyl}-mutilin is obtained. $^1$H-NMR(DMSO-$d_6$): 7.1 (bs,1H,NH), 6.1, 5.05, 5.0 (3×m,$H_{19}$,$H_{20}$,$H_{21}$), 5.55 (d,1H,$H_{14}$, J=8.2 Hz), 4.5 (m,2H,$H_{11}$—OH,H-3a'), 4.4 (d, 1H, H-6a', J=4 Hz), 3.3-4.0 (m,9H,H-2',H-3',H-5',H-6',$H_{11}$,$H_{22}$), 1.36 (s,9H,tert-butyl), 1.34, 1.05 (2×s, $(CH_3)_{15}$, $(CH_3)_{18}$), 0.8, 0.62 (2×d $(CH_3)_{16}$, $(CH_3)_{17}$,J=6.8 Hz).

I-OF) 14-O-{[(3S,3aS,6S,6aR)-6-Amino-hexahydro-furo[3,2-b]furan-3-ylsulfanyl]-acetyl}-mutilin 950 mg of 14-O-{[(3S,3aS,6S,6aR)-6-tert-butoxycarbonylamino-hexahydro-furo[3,2-b]furan-3-ylsulfanyl]-acetyl}-mutilin are dissolved in 20 ml of $CH_2Cl_2$ and the mixture obtained is stirred for 2 hours with 3 ml of TFA. The mixture obtained is diluted with EtAc and extracted with saturated aqueous $NaHCO_3$-solution. The organic phase obtained is dried and solvent is evaporated. 14-O-{[(3S,3aS,6S,6aR)-6-amino-hexahydro-furo[3,2-b]furan-3-ylsulfanyl]-acetyl}-mutilin is obtained.

I-OG) 14-O-{[(3S,3aS,6S,6aR)-6-Amino-hexahydro-furo[3,2-b]furan-3-ylsulfanyl]-acetyl}-mutilin in the form of a hydrochloride 180 mg of 14-O-{[(3S,3aS,6S,6aR)-6-amino-hexahydro-furo[3,2-b]furan-3-ylsulfanyl]-acetyl}-mutilin are distributed between diethylether and 0.1N HCl. The aqueous layer obtained is lyophilized. 14-O-{[(3S,3aS,6S,6aR)-6-Amino-hexahydro-furo[3,2-b]furan-3-ylsulfanyl]-acetyl}-mutilin in the form of a hydrochloride is obtained. Characterisation data see in TABLE 4, Example 36a above.

Example I-P

14-O-{[(3S,3aS,6S,6aR)-6-((R)-Amino-3-methyl-butyrylamino)-hexahydro-furo[3,2-b]furan-3-ylsulfanyl]-acetyl}-mutilin in the form of a hydrochloride A solution of 400 mg of 14-O-{[(3S,3aS,6S,6aR)-6-amino-hexahydro-furo[3,2-b]furan-3-ylsulfanyl]-acetyl}-mutilin in 20 ml of $CH_2Cl_2$ is treated with 128 mg of N-Boc-(R)-valine, 147 mg of EDC, 104 mg of HOBT and the mixture obtained is stirred overnight at RT. The mixture obtained is diluted with $CH_2Cl_2$, extracted with $H_2O$, dried and solvent is evaporated. The evaporation residue obtained is subjected to chromatography on silica gel, relevant chromatographic fractions obtained are treated again with TFA in $CH_2Cl_2$, solvent is evaporated, the evaporation residue obtained is distributed between $Et_2O$ and 0.1N HCl and the aqueous layer obtained is lyophilized. 14-O-{[(3S,3aS,6S,6aR)-6-((R)-2-amino-3-methyl-butyrylamino)-hexahydro-furo[3,2-b]furan-3-ylsulfanyl]-acetyl}-mutilin in the form of a hydrochloride is obtained. Characterisation data see in TABLE 5, Example 38a.

Example I-Q

14-O-[((3-(R/S)-Amino-cyclohexan-1-(R/S)-yl)-sulfanyl acetyl)]-mutilin in the form of a hydrochloride 10.6 g of pleuromutilin-22-O-tosylate dissolved in 10 ml of THF are slowly added to a solution of 5.2 g of N—BOC-3-(R/S)-mercapto-cyclohexylamin and 2.74 g of potassium-tert.butylate in 250 ml of THF. The mixture obtained is stirred for 2 hours, distributed between brine and EtAc, and extracted with 0.1N HCl. The organic phase obtained is dried, solvent is evaporated and the evaporation residue obtained is subjected to chromatography. 14-O—[((N—BOC-3(R/S)-amino-cyclohexan-1-(R/S)-yl)-sulfanyl acetyl)]-mutilin is obtained and is converted into 14-O-[((3-(R/S)-Amino-cyclohexan-1-(R/S)-yl)-sulfanyl acetyl)]-mutilin in the form of a hydrochloride by treatment with etheric HCl.

$^1$H-NMR($d_6$-DMSO): 8.0 (b,3H,$NH_3^+$), 6.15, 5.1 (2×m, $H_{19}$,$H_{20}$,$H_{21}$), 5.52(d,1H,J=5,2 Hz,$H_{14}$), 3.4(m,1H,$H_{11}$),3.3 (m,2H,$H_{22}$), 2.9 (m,1H,NCH), 2.7(m,1H,CHS), 1.18,1.45 (2×s,$(CH3)_{15}$, $(CH3)_{18}$), 0.75, 0.88 (2×d,$(CH_3)_{16}$,$(CH_3)_{17}$, J=5.4 Hz)

II. Preparation of Intermediates (Starting Materials) for the Preparation of a (Novel) Pleuromutilin of the Present Invention

Example II-A

14-Mercapto-acetyl-mutilin

I-AA) 14-O-[(Carbamimidoylsulfanyl)acetyl]mutilin-tosylate

A solution of 15.2 g of thiourea and 106.4 g of pleuromutilin-22-O-tosylate in 250 ml of acetone is heated under reflux for 1.5 hours, solvent is removed and 100 ml of hexane are added. A precipitate forms, is filtrated off and dried. 14-O-[(carbamimidoylsulfanyl)acetyl]mutilin-tosylate is obtained.

II-AB) 14-Mercapto-acetyl-mutilin

A solution of 4.7 g of $Na_2S_2O_5$ in 25 ml of $H_2O$ is added to a solution of 12.2 g of 14-O-[(carbamimidoylsulfanyl)acetyl] mutilin-tosylate in a mixture of 20 ml of EtOH and 35 ml of $H_2O$ (warmed to ca. 90°). 100 ml of $CCl_4$ are added to the reaction mixture obtained and the mixture obtained is heated under reflux for ca. 2 hours. The two-phase system obtained is separated, the organic phase is dried and solvent is evaporated. 14-mercapto-acetyl-mutilin is obtained.

Example II-B

N—BOC-3(R)-methylsulfonyloxy-piperidine

II-BA) N—BOC-3(R)-Hydroxy-piperidine

A suspension of 3.48 g of 3-(R)-hydroxypiperidine, 8.72 g of di-tert.butyl-dicarbonate and 4 g of N-methyl-morpholine in 70 ml of dioxane is stirred for 18 hours at RT. From the mixture obtained solvent is evaporated and the evaporation residue obtained is dissolved in $CH_2Cl_2$ and extracted with 1N HCl. The organic phase obtained is dried and solvent is evaporated. N—BOC-3(R)-hydroxy-piperidine is obtained.

II-BB) N—BOC-3(R)-methylsulfonyloxy-piperidine

A solution of 5.08 g of N—BOC-3(R)-hydroxy-piperidine and 8.7 g of methanesulfonic acid anhydride in 100 ml pyridine is stirred at RT for 22 hours, pyridine is distilled off, the distillation residue is dissolved in $CH_2Cl_2$, the mixture obtained is extracted with 1N HCl, the organic phase obtained is dried, solvent is evaporated and the evaporation residue obtained is subjected to chromatography. N—BOC-3(R)-methylsulfonyloxy-piperidine is obtained.

$^1$H-NMR ($CDCl_3$): 4.7(m,1H,$CHOSO_2CH_3$), 3.2-3.6(m, 4H,CHN), 3.0(s,3H,$CH_3SO_2$),1.4(m, 9H,tert.butyl).

Example II-C

N—BOC-Piperidine-3(S)-thiol

II-CA) N—BOC-3-(S)-Thioacetoxy-piperidine

A solution of 2.2 g of N—BOC-3-(R)-hydroxy-piperidine in 10 ml of THF is added under argon and 1 ml of thiolacetic acid to a solution of 3.4 g of triphenylphosphine and 2.65 ml of azadicarbonic acid-isopropylate in 10 ml of THF. The mixture obtained is kept for 18 hours at 70°, solvent is evaporated and the evaporation residue obtained is subjected to chromatography. N—BOC-3-(S)-thioacetoxy-piperidine is obtained. $^1$H-NMR ($CDCl_3$): 3.78 (dd,1H,$NCH_2CHS$, J=3.1 Hz, J=13.3 Hz), 3.5-3.6 (m,2H, CHSC═O, $NCH_2CH_2$), 2.32 (s,3H,SC═$OCH_3$),1.46(s,9H, tert.butyl)

II-CB) N—BOC-Piperidine-3(S)-thiol

To a solution of 259 mg of N—BOC-3-(S)-thioacetoxy-piperidine in 10 ml of MeOH a solution of 262 mg of $NaSCH_3$ in 5 ml of MeOH is added and the mixture obtained is stirred for 2 hours, solvent is evaporated and the evaporation residue obtained is distributed between EtAc and aqueous HCl. Solvent from the organic phase obtained is evaporated.

N—BOC-piperidine-3(S)-thiol is obtained. $^1$H-NMR($d_6$-DMSO): 2.6 (d,1H,SH, J=7.2 Hz),2.9-2.7 (m,3H, $NCH_2$, CHS), 1.35 (b,9H,tert.butyl). MS (ESI) 457 (2M+Na).

Example II-D 3-(N—BOC—(R)-Valyl-amino)-cyclohexane-(R/S)-thiol

II-DA) 3-(R/S)-(2,4,6-Trimethyl-benzyl-sulfanyl)-cyclohexanone

A solution of 3.32 g of 2,4,6-trimethyl-benzylmercaptane and 3.84 g of cyclohexen-3-one in 30 ml of pyridine is heated at 40° for 3 hours. The mixture obtained is poured into 200 ml of 1M HCl and the mixture obtained is extracted with $CH_2Cl_2$. The organic phase obtained is dried, solvent is evaporated and the evaporation residue is subjected to chromatography on silica gel. 3-(R/S)-(2,4,6-trimethyl-benzyl-sulfanyl)-cyclohexanone is obtained.

$^1$H-NMR($d_6$-DMSO): 6.8 (s,2H,arom.H), 3.8 (s,2H, $C_6H_5CH_2S$—), 3.3 (m,1H,CHS), 3.18 (dd,1H, CHC═NOH, J=4 Hz,13.9 Hz), 2.65-2.8, 2.44-2.49(2×m,4H, $CH_2C$═$OCH_2$),2.15,2.3(9H,3×$CH_3$).

II-DB) 3-(R/S)-(2,4,6-Trimethyl-benzyl-sulfanyl)-cyclohexanone-oxime (syn and anti-forms)

A solution of 5.24 g of 3-(R/S)-(2,4,6-trimethyl-benzyl-sulfanyl)-cyclohexanone, 1.38 g of hydroxylamine in the form of a hydrochloride and 2 g of triethylamine in 50 ml of MeOH is stirred at 25° for 12 hours, the mixture obtained is poured into 200 ml of brine and the mixture obtained is extracted with $CH_2Cl_2$. The organic phase obtained is dried and solvent is evaporated. A mixture of the syn- and anti forms of 3-(R/S)-(2,4,6-trimethyl-benzyl-sulfanyl)-cyclohexanone-oxime is obtained which is subjected to chromatography. Pure syn- and pure anti-3-(R/S)-(2,4,6-trimethyl-benzyl-sulfanyl)-cyclohexanone-oxime is obtained.

$^1$H-NMR($d_6$-DMSO) of the syn-form: 10.3 (s,1H,OH), 6.8 (s,2H,arom.H), 3.75 (s,2H, $C_6H_5CH_2S$—), 2.88 (m,1H, CHS), 3.18 (dd,1H,CHC═NOH, J=4 Hz,13.9 Hz), 2.13 (dd, 1H, CHC═NOH, J=5.2 Hz,13.9 Hz), 2.15,2.3(9H, 3×$CH_3$).

$^1$H-NMR($d_6$-DMSO) of the anti-form: 10.3 (s,1H,OH), 6.8 (s,2H,arom.H), 3.75 (s,2H, $C_6H_5CH_2S$—), 2.92(m,1H, CHS), 2.58 (dd,1H,CHC═NOH, J=4 Hz,13.9 Hz), 2.15 (dd, 1H, CHC═NOH, J=4.2 Hz,13.6 Hz),2.15,2.3(9H, 3×$CH_3$).

II-DC) 3-(R/S)-(2,4,6-trimethyl-benzyl-sulfanyl)-cyclohexyl-(R/S)-amine 2.7 g of 3-(R/S)-(2,4,6-Trimethyl-benzyl-sulfanyl)-cyclohexanone-oxime are added to a mixture of 20 ml of a 1M-solution of $LiAlH_3$ and 15 ml of dioxane, the mixture obtained is heated for 1 hour at 80° and the mixture obtained is poured into 200 ml of a 20% aqueous $NH_4Cl$-solution. The mixture obtained is extracted with EtAc, the organic phase obtained is dried and solvent is evaporated. 3-(R/S)-(2,4,6-trimethyl-benzyl-sulfanyl)-cyclohexyl-(R/S)-amine is obtained.

II-DC) 3-(N—BOC—(R)-Valyl-amino)-cyclohexan-1-(R/S)-yl-sulfanylmethyl-(2,4,6-trimethyl-benzol)

A mixture of 1.05 g of 3-(R/S)-(2,4,6-trimethyl-benzyl-sulfanyl)-cyclohexyl-(R/S)-amine, 870 mg of BOC—R-valine, 760 mg of EDC and 404 mg of triethylamine in 20 ml THF is stirred at RT for 2 hours. The mixture obtained is distributed between brine and EtAc, the organic phase obtained is dried, solvent is evaporated and the evaporation residue is subjected to chromatography. 3-(N—BOC—(R)-valyl-amino)-cyclohexan-1-(R/S)-yl-sulfanylmethyl-(2,4,6-trimethyl-benzol) is obtained. $^1$H-NMR($d_6$-DMSO): Rotamers, 7.78, 7.3, 6.52 (3×d,2H,NH), J=7.9 Hz), 6.8, 6.82 (2×s, 2H, arom.H), 6.55 (m,1H,NHC═O),3.7 (m,1H,a-H-valyl), 3.6 (m,1H,NHCH), 2.75, 3.0 (2×m,1H, CHS), 1.39(s,9H, tert.butyl)

II-DD) 3-(N—BOC—(R)-Valyl-amino)-cyclohexane-(R/S)-thiol 10 ml ammonia are condensed at −70° within a solution of 600 mg of 3-(N—BOC—(R)-valyl-amino)-cyclohexan-1-(R/S)-yl-sulfanylmethyl-2,4,6-trimethyl-benzol in 15 ml of THF and sodium is added in portions until the solution remains deep blue. Solid $NH_4Cl$ is added to the mixture obtained and the mixture obtained is allowed to warm up to RT, is flushed with nitrogen, the solid residue obtained is filtered off, the filtrate obtained is concentrated and subjected to chromatography on silica gel. 3-(N—BOC—(R)-Valyl-amino)-cyclohexane-(R/S)-thiol is obtained. $^1$H-NMR($d_6$-DMSO): Rotamer, 7.75 (m,1H,NHCHC═O), 6.55 (m,1H, NHC═O),2.75 (m,1H,CHS), 2.58(d,1H,SH,J=6.6 Hz), 1.39 (s,9H, tert.butyl)

Analogously to the method as set out in Example II-D but using appropriate starting materials the following compounds are obtained:

Example II-D-1

N—BOC-3-(R/S)-mercapto-cyclohexylamin

Example II-D-2 4-(R/S)-Mercapto-azepan-2-one from 4-R/S)-(2,4,6-trimethyl-benzyl-sulfanyl)-azepan-2-one. $^1$H-NMR($d_6$-DMSO): 6.15, 5.1 (2×m, $H_{19}$,$H_{20}$,$H_{21}$), 5.52(d,1H,J=5,2 Hz,$H_{14}$), 3.4(m,1H, $H_{11}$), 3.3 (m,2H,$H_{22}$), 2.99-3.12(b,2H,$CH_2N$), 3.18 (m,1H,SCH), 2.7 (m,1H,C═OCH), 2.67(d,1H,SH, J=5.5 Hz), 2.58(d,1H,C═OCH,J=13.5 Hz), 1.18, 1.45 (2×s,$(CH3)_{15}$, $(CH3)_{18}$), 0.75,0.88 (2×d,$(CH_3)_{16}$,$(CH_3)_{17}$,J=5.4 Hz).

Example II-E

N—BOC-3-(R/S)-(2,4,6-trimethyl-benzyl-sulfanyl)-cyclohexyl-(R/S)-amine

A solution of 11 g of 3-(R/S)-(2,4,6-trimethyl-benzyl-sulfanyl)-cyclohexylamine, 9.15 g of BOC-anhydride and 4.2 g of triehylamine in 100 ml of THF is stirred at 25° for 12 hours, solvent is evaporated and the concentrated residue is distributed between $CH_2Cl_2$ and 1M HCl. From the organic phase obtained solvent is evaporated and the evaporation residue is subjected to chromatography. N—BOC-3-(R/S)-(2,4,6-trimethyl-benzyl-sulfanyl)-cyclohexyl-(R/S)-amine is obtained. $^1$H-NMR($d_6$-DMSO): 6.81,(s,1H,NHCO), 6.8 (s,2H, arom.H), 3.75 (s,2H,$C_6H_5CH_2S$—),3.2 (m,1H,CHN), 2.70 (m,1H,CHS), 2.13 2.15,2.3(9H, 3×$CH_3$),1.4(s,9H, tert.butyl)

Example II-F

Toluene-4-sulfonic acid (3S,3aS,6R,6aR)-6-hydroxy-hexahydro-furo[3,2-b]furan-3-yl ester and Toluene-4-sulfonic acid (3R, 3aS,6S,6aR)-6-hydroxy-hexahydro-furo[3,2-b]furan-3-yl ester A solution of 8.76 g of (3S,3aS,6R,6aR)-hexahydro-furo [3,2-b]furan-3,6-diol in 80 ml of pyridine is stirred for 16 hours with 13.7 g of toluenesulfonylchloride, solvent is distilled off and the distillation residue is dissolved in EtAc and extracted with 1N HCl, saturated aqueous $NaHCO_3$-solution and $H_2O$. The organic layer obtained is dried, solvent is evaporated and the evaporation residue is subjected to chromatography. Toluene-4-sulfonic acid (3S,3aS,6R,6aR)-6-hydroxy-hexahydro-furo[3,2-b]furan-3-yl ester (a) and toluene-4-sulfonic acid (3R,3aS,6S,6aR)-6-hydroxy-hexahydro-furo [3,2-b]furan-3-yl ester (b) are obtained. $^1$H-NMR(DMSO-$d_6$) of form (a): 7.8 (d,2H,Ar—H,J=8.2 Hz), 7.5 (d,2H,Ar—H,J=8.6 Hz), 4.95 (d,1H,6-OH), 4.8 (m, 1H, H-3), 4.42 (dd, 1H,H-6a,J=4.6 and 4.8 Hz), 4.38 (d,1H,H-3a,J=4.6), 4.08 (m,1H,H-6), 3.8 (m,2H,2×H-2), 3.7, 3.25 (2×dd, 2H, 2×H-5), 2.4 (s, 3H, Ar—$CH_3$).

$^1$H-NMR(DMSO-$d_6$) of form (b): 7.8 (d,2H,Ar—H,J=8.6 Hz), 7.5 (d,2H,Ar—H,J=8.6 Hz), 5.15 (d, 6-OH, J=3.5), 4.9 (m,1H,H-3), 4.45 (dd,1H,H-3a,J=4.3 and 4.8 Hz), 4.2 (d,1H, H-6a,J=4.3), 4.0 (m,1H,H-6), 3.7 (m,3H,H-2 and 2×H-5), 3.5 (dd,1H,H-2,J=9.5 and 6.3 Hz), 2.4 (s, 3H, Ar—$CH_3$).

Example II-G

N—BOC-4-Hydroxy-piperidin-3-thiol, N—BOC-3-Hydroxy-piperidin-4-thiol

A solution of 1 g of N—BOC-3,4-epoxy-piperidin, 1.9 g of triphenylsilylmercaptane and 0.7 ml of triethylamine in 12.5 ml of THF is stirred for 24 hours at 70°, and 1.7 g of TBAF and 0.9 ml acetic acid are added. The mixture obtained is stirred for 1 hour and distributed between brine and EtAc. The organic phase is dried, solvent is evaporated and the evaporation residue obtained is subjected to chromatography on silica gel. (a): N—BOC-4-Hydroxy-piperidin-3-thiol, and (b): N—BOC-3-hydroxy-piperidin-4-thiol are obtained.

$^1$H-NMR ($CDCl_3$) of (a): 4.45, 4.12, 2.8 (3×m,3H, $CH_2NCH$), 3.31 (dt, 1H, CHO, J=4.3 Hz,J=10 Hz), 2.65,2.6 (2×m,2H,CHN,CHS), 1.5(s,9H,tert.butyl).

$^1$H-NMR ($CDCl_3$) of (b): 4.25, 3.45 2.7, (3×m,3H, $CH_2NCH$), 3.2 (m,1H,CHO), 2.55(m,2H, NCH,CHS), 1.5 (s,9H,tert.butyl).

TEST EXAMPLES

Example A

Determination of *Mycobacterium tuberculosis* Strain Resistance

Activity of the known compounds Isoniacid, Rifampicin and Streptomycin against *M. tuberculosis* strains 1 to 14 as set out in TABLE A is determined in the Agar Dilution Test according to the method as described in the General Procedure. The MIC is determined after 3, 4 and 5 weeks. The strains 1 to 7 tested were found to be either sensible (S) or resistant (R) against Isoniacid, Rifampicin and/or Streptomycin. Results are as set out in TABLE A below:

TABLE A

| M.tuberculosis | Isoniacid | Rifampicin | Streptomycin |
|---|---|---|---|
| Strain 1 | S | S | S |
| Strain 2 | S | S | S |
| Strain 3 | R | R | S |
| Strain 4 | R | R | R |
| Strain 5 | R | R | S |
| Strain 6 | S | S | S |
| Strain 7 | R | S | R |
| Strain 8 | S | R | S |
| Strain 9 | R | S | R |
| Strain 10 | S | S | S |
| Strain 11 | S | S | S |
| Strain 12 | S | S | S |
| Strain 13 | S | S | S |
| Strain 14 | S | S | S |
| Strain 15 | S | S | S |

Strain 15 is the labor strain 137 kV. Resistant and sensible strains are isolated from patients with known sensibilities/resistance. A strain is designated as resistant if its MIC in testing according to the General Test Procedure after 3 to 5 weeks is higher than 20 μg/ml.

Example B

Activity of TEST COMPOUNDS (TCs) against *M. tuberculosis* strains 1 to 5 and 7 as set out in TABLE A is determined in the Agar Dilution Test under conditions as in Example A in different agar concentrations of the TEST COMPOUNDS.

The MIC is determined after 3, 4 and 5 weeks.

Activity of the following TEST COMPOUNDS (TC) is tested:

| | |
|---|---|
| A compound of formula I-Tiamulin: | TC-1 |
| A compound of formula I-Valnemulin: | TC-2 |
| A compound of formula I-PREF1: | TC-3 |
| A compound of formula I-PREF2: | TC-4 |
| A compound of formula I-PREF3: | TC-5 |
| A compound of formula I-PREF4: | TC-6 |
| A compound of formula I-PREF5: | TC-7 |
| A compound of formula I-PREF6: | TC-8 |
| A compound of formula I-PREF7: | TC-9 |
| A compound of formula I-PREF8: | TC-10 |

Test results are as set out in TABLE B below are obtained:

TABLE B

| | MIC (µg/ml) against Mycobacterium tuberculosis of strain number | | | | | |
|---|---|---|---|---|---|---|
| TC/week | 1 | 2 | 3 | 4 | 6 | 7 |
| TC-1/3 | 5 | 5 | 5 | 5 | 10 | 10 |
| TC-1/4 | 5 | 5 | 5 | 10 | 10 | 20 |
| TC-1/5 | 5 | 5 | 5 | 10 | 10 | 20 |
| TC-2/3 | 0.5 | 1 | 1 | 5 | 5 | 5 |
| TC-2/4 | 0.5 | 5 | 1 | 5 | 5 | 5 |
| TC-2/5 | 0.5 | 5 | 5 | 5 | 5 | 10 |
| TC-3/3 | 1 | 5 | 5 | 1 | 5 | 20 |
| TC-3/4 | 1 | 5 | 5 | 5 | 10 | 20 |
| TC-3/5 | 1 | 5 | 5 | 10 | 10 | 20 |
| TC-4/3 | 0.5 | 5 | 1 | 1 | 5 | 5 |
| TC-4/4 | 1 | 5 | 1 | 5 | 5 | 5 |
| TC-4/5 | 1 | 5 | 5 | 5 | 5 | 5 |
| TC-5/3 | 1 | 5 | 5 | 5 | 5 | 5 |
| TC-5/4 | 5 | 5 | 5 | 5 | 10 | 10 |
| TC-5/5 | 5 | 5 | 5 | 10 | 10 | 10 |

Example C

Is carried out according to the method of Example B. Test results obtained are as set out in TABLE C and in TABLE D and in TABLE E:

TABLE C

| | MIC (µg/ml) against Mycobacterium tuberculosis of strain number | | | | | | | |
|---|---|---|---|---|---|---|---|---|
| TC/week | 1 | 2 | 3 | 4 | 5 | 6 | 7 | 8 |
| TC-2/3 | 0.5 | 4 | 2 | 8 | 2 | 4 | 4 | 4 |
| TC-2/4* | 0.5 | 4 | 2 | 8 | 4 | 4 | 8 | 8 |
| TC-4/3 | 1 | 4 | 1 | 4 | 2 | 4 | 2 | 2 |
| TC-4/4 | 2 | 4 | 1 | 4 | 2 | 4 | 4 | 2 |
| TC-4/5 | 2 | 4 | 1 | 4 | 2 | 4 | 4 | 4 |

TABLE C-continued

*Tested after 31 days and thus no further testing after 5 weeks.

TABLE D

| | MIC (µg/ml) against Mycobacterium tuberculosis of strain number | | | | | |
|---|---|---|---|---|---|---|
| TC/week | 10 | 11 | 12 | 13 | 14 | 15 |
| TC-2/3 | 4 | 2 | 4 | 4 | 4 | 2 |
| TC-2/4* | 4 | 4 | 4 | 8 | 4 | 4 |
| TC-4/3 | 2 | 2 | 2 | 2 | 4 | 2 |
| TC-4/4 | 2 | 2 | 2 | 2 | 4 | 2 |
| TC-4/5 | 4 | 2 | 4 | 4 | 4 | 4 |

*Tested after 31 days and thus no further testing after 5 weeks.

TABLE E

| | MIC (µg/ml) against Mycobacterium tuberculosis of strain number | | |
|---|---|---|---|
| TC/week | 1 | 12 | 15 |
| TC-6/2 | 1 | 1 | 0.5 |
| TC-7/1 | 2 | 32 | 32 |
| TC-8/1 | 2 | 32 | 32 |
| TC-9/1 | 8 | 32 | 32 |
| TC-10/2 | 2 | 16 | 4 |

In TABLES B to E in the column "TC/week" the term "TC-number" indicates the TEST COMPOUND as defined above, e.g. TC-1 indicates a compound of formula I-Tiamulin; and "/week" indicates the MIC-determination point (in weeks from inoculation) in the testing of such TEST COMPOUND. "TC-1/3" for example indicates that the MIC of a compound of formula I-Tiamulin was determined after 3 weeks from inoculation.

MIC is the minimum inhibition concentration as defined above. The strain numbers 1 to 4 and 6 to 7 indicated in TABLE B, the strain numbers 1 to 9 indicated in TABLE C and the strain numbers 10 to 15 indicated in TABLE D, and the strain numbers 1, 12 and 15 indicated in TABLE E refer to the corresponding *Mycobacterium tuberculosis* strains of Example A.

Furthermore compounds of formula $I_{EX}$ and compounds of formula $I'_{EX}$ wherein $R_{EX}$ is as defined in TABLE 6 below have also proved to show activity against strains 1, 12 and 15 (all compounds tested in the form of hydrochlorides):

TABLE 6

| | $R_{EX}$ | $R_{EX}$ | $R_{EX}$ |
|---|---|---|---|
| Compound $I_{EX}$ | 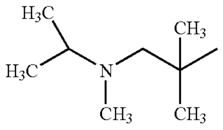 | 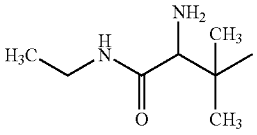 | 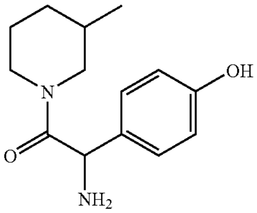 |
| Compound $I_{EX}$ | 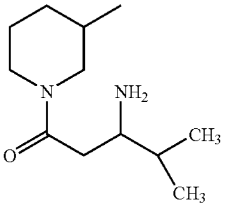 | 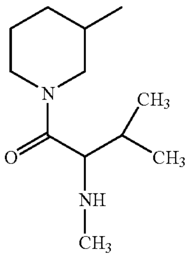 | 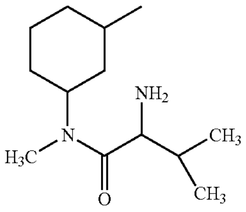 |
| Compound $I_{EX}$ | 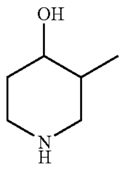 | 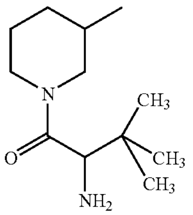 | 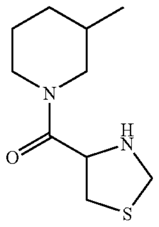 |
| Compound $I_{EX}$ | 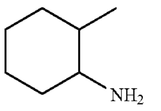 | 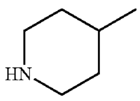 | |
| Compound $I'_{EX}$ | 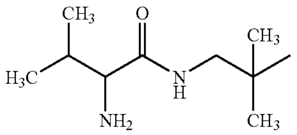 | | |

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A 14-O-(oximino-($C_{3-8}$)cycloalkyl-sulfanylmethylcarbonyl)-pleuromutilin and a 14-O-(hydrazono-($C_{3-8}$)cycloalkyl-sulfanylmethylcarbonyl)-pleuromutilin.

2. A compound of formula

IB

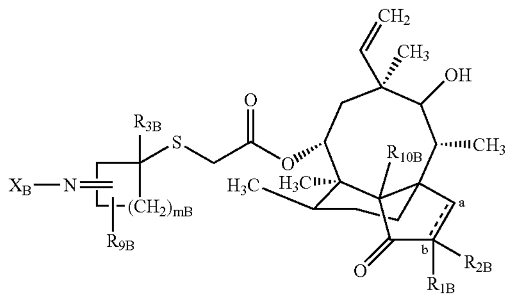

wherein the dotted line is a bond, $R_{1B}$ is hydrogen and $R_{2B}$ is not present, or the dotted line is no bond and $R_{1B}$ and $R_{2B}$ independently of each other are hydrogen, halogen or deuterium, $m_B$ is 0, 1, 2, 3, 4, or 5, $R_{3B}$ is hydrogen or $(C_{1-6})$alkyl, $X_B$ is —O—$R_{4B}$ or —$NR_{5B}R_{6B}$, $R_{4B}$ is hydrogen or $(C_{1-6})$alkyl, optionally substituted by a group —$NR_{7B}R_{8B}$, $R_{5B}$ and $R_{6B}$ independently of each other are $(C_{1-4})$alkyl, $R_{7B}$ and $R_{8B}$ independently of each other are $(C_{1-4})$alkyl, or $R_{7B}$ and $R_{8B}$ together with the nitrogen atom to which they are attached form aliphatic heterocyclyl, having 5 to 8 ring members, and $R_{9B}$ is hydrogen or $(C_{1-4})$alkyl.

* * * * *